US011566292B2

(12) United States Patent
Bayani et al.

(10) Patent No.: US 11,566,292 B2
(45) Date of Patent: Jan. 31, 2023

(54) GENE SIGNATURE OF RESIDUAL RISK FOLLOWING ENDOCRINE TREATMENT IN EARLY BREAST CANCER

(71) Applicant: ONTARIO INSTITUTE FOR CANCER RESEARCH (OICR), Toronto (CA)

(72) Inventors: Jane Bayani, Richmond Hill (CA); John M. S. Bartlett, Toronto (CA); Cindy Q. Yao, North York (CA); Paul C. Boutros, Toronto (CA)

(73) Assignee: ONTARIO INSTITUTE FOR CANCER RESEARCH (OICR), Toronto (CA)

(*) Notice: Subject to any disclaimer, the term of this patent is extended or adjusted under 35 U.S.C. 154(b) by 149 days.

(21) Appl. No.: 15/781,939

(22) PCT Filed: Dec. 7, 2016

(86) PCT No.: PCT/CA2016/000304
§ 371 (c)(1),
(2) Date: Jun. 6, 2018

(87) PCT Pub. No.: WO2017/096457
PCT Pub. Date: Jun. 15, 2017

(65) Prior Publication Data
US 2019/0010553 A1 Jan. 10, 2019

Related U.S. Application Data

(60) Provisional application No. 62/263,805, filed on Dec. 7, 2015.

(51) Int. Cl.
*C12Q 1/6886* (2018.01)
*G01N 33/574* (2006.01)
*G16H 50/30* (2018.01)

(52) U.S. Cl.
CPC ..... *C12Q 1/6886* (2013.01); *G01N 33/57415* (2013.01); *G16H 50/30* (2018.01); *C12Q 2600/106* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| 2011/0294681 | A1* | 12/2011 | Hinds | C12Q 1/6886 506/9 |
| 2014/0302042 | A1* | 10/2014 | Chin | C12Q 1/6886 424/139.1 |
| 2014/0363816 | A1* | 12/2014 | Theodorescu | C12Q 1/6886 435/6.11 |

FOREIGN PATENT DOCUMENTS

| JP | 2007505630 | 3/2007 |
| WO | WO 2009/158143 | 12/2009 |
| WO | WO 2012/112645 | 8/2012 |
| WO | WO 2013/188600 | 12/2013 |

OTHER PUBLICATIONS

Symmans et al. (Journal of clinical oncology 2010 vol. 28 p. 4111) (Year: 2010).*
Affymetrix U133 (affymetrix.com probe set downloaded Mar. 10, 2020) (Year: 2020).*
Enard et al. (Science 2002 vol. 296 p. 340) (Year: 2002).*
Chanrion, et al., "A Gene Expression Signature That Can Predict the Recurrence of Tamoxifen-Treated Primary Breast Cancer," Clinical Cancer Research, 14(6), 2008.
Extended European Search Report Issued in Corresponding European Application No. 16871846.8, dated Jun. 24, 2019.
Lyng, et al., "Gene Expression Signatures That Predict Outcome of Tamoxifen-Treated Estrogen Receptor-Positive, High-Risk, Primary Breast Cancer Patients: A DBCG Study," PLOS One, 8(1); e54078, 2013.
Abe, et al., "Effects of Chemotherapy and Hormonal Therapy for Early Breast Cancer on Recurrence and 15-Year Survival: An Overview of the Randomised Trials," *Lancet*, 365; 1687-1717, 2005.
Afentakis, et al., "Immunohistochemical BAG1 Expression Improves the Estimation of Residual Risk by IHC4 in Postmenopausal Patients Treated with Anastrazole or Tamoxifen: A TransATAC Study," *Breast Cancer Research and Treatment*, 140; 253-262, 2013.
Bartlett, et al., "Comparing Breast Cancer Multiparameter Tests in the OPTIMA Prelim Trial: No Test Is More Equal Than the Others," Journal of the National Cancer Institute 108(9); 1-9, 2016.
Bartlett, et al., "Do type 1 Receptor Tyrosine Kinases Inform Treatment Choice? A Prospectively Planned Analysis of the TEAM Trial," British Journal of Cancer, 109; 2453-2461, 2013.
Bartlett, et al., "Estrogen Receptor and Progesterone Receptor as Predictive Biomarkers of Response to Endocrine Therapy: A Prospectively Powered Pathology Study in the Tamoxifen and Exemestane Adjuvant Multinational Trial," Journal of Clinical Oncology, 29(12); 1531-1538, 2011.
Bartlett, et al., "Selecting Breast Cancer Patients for Chemotherapy: The Opening of the UK OPTIMA Trial," *Clinical Oncology*, 25(2); 109-116, 2013.

(Continued)

*Primary Examiner* — Katherine D Salmon
(74) *Attorney, Agent, or Firm* — Norton Rose Fulbright US LLP

(57) ABSTRACT

There is described herein a method of prognosing endocrine-only treatment in a subject with breast cancer, the method comprising: a) providing a tumor sample of the breast cancer; b) determining the expression level of at least 40 of the genes listed in Table 4 in the tumor sample; c) comparing said expression levels to a reference expression level of the group of genes from control samples from a cohort of subjects; and d) determining the residual risk associated with the breast cancer; wherein a statistically significant difference or similarity in the expression of the group of genes compared to the reference expression level corresponds to a residual risk associated with breast cancer.

9 Claims, 28 Drawing Sheets

(56) References Cited

OTHER PUBLICATIONS

Barton, et al., Assessment of the Contribution of the IHC4+C Score to Decision Making in Clinical Practice in Early Breast Cancer, *British Journal Cancer*, 106; 1760-1765, 2012.

Breitling, et al., "Rank Products: A Simple, Yet Powerful, New Method to Detect Differentially Regulated Genes in Replicated Microarray Experiments," FEBS Letters, 573; 83-92, 2004.

Cardoso, et al., "Clinical Application of the 70-Gene Profile: The MINDACT Trial," *Journal of Clinical Oncology*, 26; 729-735, 2008.

Chia, et al., "A 50-Gene Intrinsic Subtype Classifier for Prognosis and Prediction of Benefit from Adjuvant Tamoxifen," *Clinical Cancer Research*, 18; 4465-4472, 2012.

Clemens, et al., "Phase II, Multicenter, Open-Label, Randomized Study of YM155 Plus Docetaxel as Firstline Treatment in Patients with HER2-Negative Metastatic Breast Cancer," *Breast Cancer Research and Treatment*, 149; 171-179, 2015.

Colleoni,. et al., "Annual Hazard Rates of Recurrence for Breast Cancer During 24 Years of Follow-Up: Results From the International Breast Cancer Study Group Trials I to V,". *Journal Clinical Oncology*, 34; 927-935, 2016.

Cuzick, et al., "Prognostic Value of a Combined Estrogen Receptor, Progesterone Receptor, Ki-67, and Human Epidermal Growth Factor Receptor 2 Immunohistochemical Score and Comparison with the Genomic Health Recurrence Score in Early Breast Cancer," *Journal of Clinical Oncology*, 29; 4273-4278, 2011.

Dowsett, et al., "Meta-Analysis of Breast Cancer Outcomes in Adjuvant Trials of Aromatase Inhibitors Versus Tamoxifen," *Journal of Clinical Oncology*, 28; 509-518, 2010.

Finn, et al., "PD 0332991, A Selective Cyclin D Kinase 4/6 Inhibitor, Preferentially Inhibits Proliferation of Luminal Estrogen Receptor-Positive Human Breast Cancer Cell Lines in Vitro," *Breast Cancer Research*, 11; R77, 2009.

Finn,. et al., "The Cyclindependent Kinase 4/6 Inhibitor Palbociclib in Combination with Letrozole Versus Letrozole Alone as First-Line Treatment of Oestrogen Receptor-Positive, HER2 Negative, Advanced Breast Cancer (PALOMA-1fTRIO-18): A Randomised Phase 2 Study," *Lancet Oncology*, 16; 25-35, 2015.

Hammond, et al.,. "Clinical Notice for American Society of Clinical Oncology-College of American Pathologists Guideline Recommendations on ER/PgR and HER2 Testing in Breast Cancer," Journal of Clinical Oncology, 29; e458, 2011.

Hosford & Miller, "Clinical Potential of Novel Therapeutic Targets in Breast Cancer: CDK4/6, Src, JAK/STAT, PARP, HDAC, and P13K/AKT/mTOR Pathways," Pharmgenomics and Personalized Medicine 7; 203-215, 2014.

International Search Report and Written Opinion Issued in Corresponding PCT Application No. PCT/CA2016/000304, dated Feb. 28, 2017.

Ma, et al., "A Five-Gene Molecular Grade Index and HOXB13:1L 17BR are Complementary Prognostic Factors in Early Stage Breast Cancer," *Clinical Cancer Research*, 14; 2601-2608, 2008.

Muller, et al. The EndoPredict Gene-Expression Assay in Clinical Practice—Performance and Impact on Clinical Decisions, *PLoS One*. 8; e68252, 2013.

Nielsen, et al., "A Comparison of PAM50 Intrinsic Subtyping with Immunohistochemistry and Clinical Prognostic Factors in Tamoxifen-Treated Estrogen Receptor-Positive Breast Cancer," *Clinical Cancer Research*, 16; 5222-5232, 2010.

Paik, et al., "A Multigene Assay to Predict Recurrence of Tamoxifen-Treated, Node-Negative Breast Cancer," *New England Journal of Medicine*, 351; 2817-2826, 2004.

Paik, et al., "Gene Expression and Benefit of Chemotherapy in Women with Node-Negative, Estrogen Receptor-Positive Breast Cancer," Journal Clinical Oncology, 24; 3726-3734, 2006.

Parker, et al., "Supervised Risk Predictor of Breast Cancer Based on Intrinsic Subtypes," Journal of Clinical Oncology, 27; 1160-1167, 2009.

Perou,. et al., "Molecular Portraits of Human Breast Tumours," Nature 406; 747-752, 2000.

Piccart, et al., "Everolimus Plus Exemestane for Hormone-Receptor-Positive, Human Epidermal Growth Factor Receptor-2-Negative Advanced Breast Cancer: Overall Survival Results from BOLERO-2 †," *Annals of Oncology*, 25; 2357-2362, 2014.

Prat, et al., "Concordance Among Gene Expression-Based Predictors for ER-Positive Breast Cancer Treated with Adjuvant Tamoxifen," Annals of Oncology, 23(11); 2866-2873, 2012.

Schemper & Smith, A Note on Quantifying Follow-Up in Studies of Failure Time, *Controlled Clinical Trials*, 17; 343-346, 1996.

Schoffski, et al., Multicentric Parallel Phase II Trial of the Polo-Like Kinase 1 Inhibitor B1 2536 in Patients with Advanced Head and Neck Cancer, Breast Cancer, Ovarian Cancer, Soft Tissue Sarcoma and Melanoma. The First Protocol of the European Organization for Research and Treatment of Cancer (EORTC) Network of Core Institutes (NOCI), *European Journal of Cancer*, 46; 2206-2215, 2010.

Schoffski, et al., "Polo-Like Kinase (PLK) Inhibitors in Preclinical and Early Clinical Development in Oncology," *Oncologist*, 14; 559-570, 2009.

Sparano, "TAILORx: Trial Assigning Individualized Options for Treatment (Rx)," *Clinical Breast Cancer*; 347-350, 2006.

Sparano, et al., "Prospective Validation of a 21-Gene Expression Assay in Breast Cancer," New England Journal Medicine, 373; 2005-2014, 2015.

Starmans, et al., "Exploiting the Noise: Improving Biomarkers with Ensembles of Data Analysis Methodologies," Genome Medicine, 4(84); 1-12, 2012.

Symmans, et al., "Genomic Index of Sensitivity to Endocrine Therapy for Breast Cancer," *Journal of Clinical Oncology*, 28(27); 4111-4119, 2010.

Toussaint, et al., "Improvement of the Clinical Applicability of the Genomic Grade Index Through a qRT-PCR Test Performed on Frozen and Formalin-Fixed Paraffin-Embedded Tissues," BMC Genomics 10(424); 1-13, 2009.

van de Velde, et al., "Adjuvant Tamoxifen and Exemestane in Early Breast Cancer (TEAM}: A Randomized Phase 3 Trial," *Lancet*, 311, 321-331 (2011).

Van de Vijver, et al., "A Gene-Expression Signature as a Predictor of Survival in Breast Cancer," *New England Journal of Medicine*, 347; 1999-2009, 2002.

Waggott, et al., "NanoStringNorm: An Extensible R Package for the Pre-Processing of NanoString mRNA and miRNA Data," *Bioinformatics*, 28; 1546-1548, 2012.

Whitfield, et al., "Identification of Genes Periodically Expressed in the Human Cell Cycle and Their Expression in Tumors," *Molecular Biology of the Cell*, 113; 1977-2000, 2002.

Wolff, et al., "American Society of Clinical Oncology/College of American Pathologists Guideline Recommendations for Human Epidermal Growth Factor Receptor 2 Testing in Breast Cancer," *Journal of Clinical Oncology*, 25; 118-145, 2007.

Wolff, et al., "Recommendations for Human Epidermal Growth Factor Receptor 2 Testing in Breast Cancer: American Society of Clinical Oncology/College of American Pathologists Clinical Practice Guideline Update," *Journal of Clinical Oncology*, 31; 3997-4013, 2013.

Yardley, et al., "Everolimus Plus Exemestane in Postmenopausal Patients with HR(+) Breast Cancer: BOLER0-2 Final Progression-Free Survival Analysis," *Advances in Therapy*, 30; 870-884, 2013.

Chanrion et al., "A Gene Expression Signature that Can Predict the Recurrence of Tamoxifen-Treated Primary Breast Cancer" *Clin. Cancer Res*. 2008, 14, 1744-1752.

Office Action issued in Corresponding Japanese Application No. 2018-530774, dated Sep. 4, 2020.

Symmans et al., "Genomic Index of Sensitivity to Endocrine Therapy for Breast Cancer" *Journal of Clinical Oncology* 2010, 28(27), 4111-4119.

\* cited by examiner

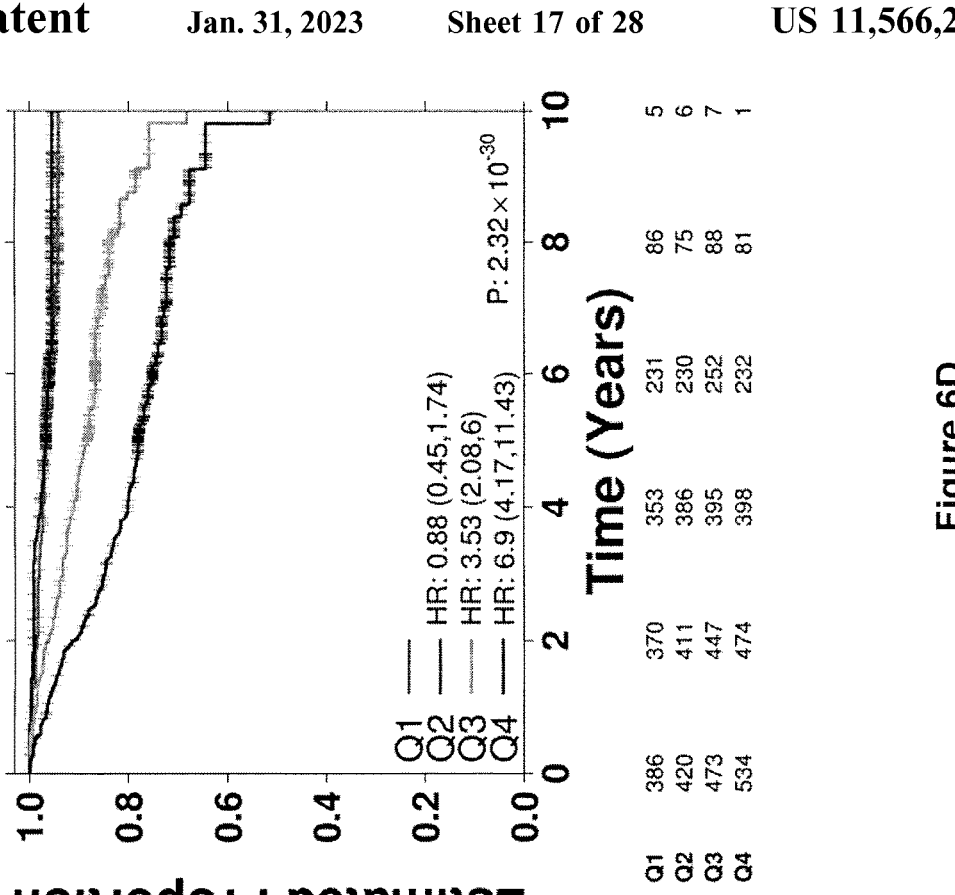
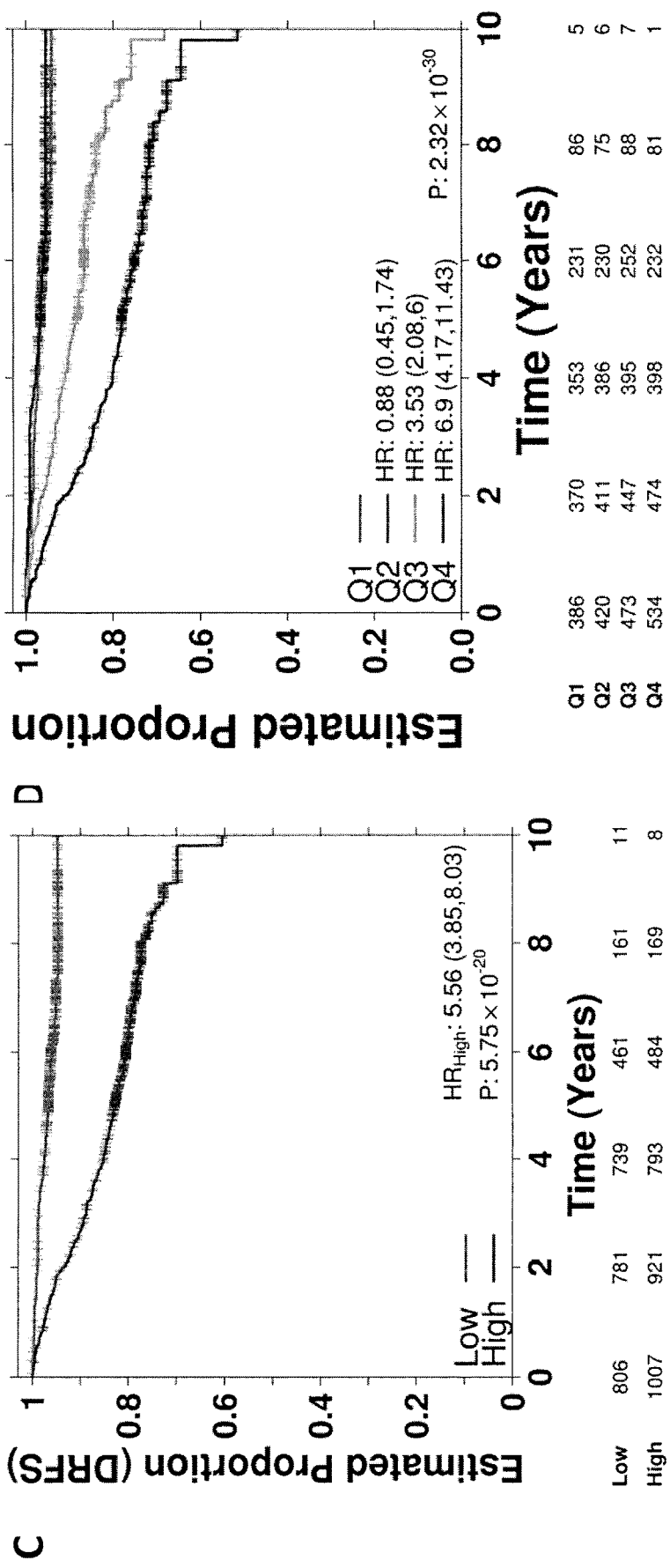
Figure 6C
Figure 6D

GENE SIGNATURE OF RESIDUAL RISK FOLLOWING ENDOCRINE TREATMENT IN EARLY BREAST CANCER

CROSS REFERENCE TO RELATED APPLICATIONS

[0001] This application is a national phase application under 35 U.S.C. § 371 of International Application No. PCT/CA2016/000304 filed Dec. 7, 2016, which claims the benefit of priority of U.S. Provisional Patent Application No. 62/263,805 filed Dec. 7, 2015, both of which are incorporated herein by reference in their entirety.

FIELD OF THE INVENTION

The present disclosure relates generally to prognosing or classifying a subject with breast cancer. More particularly, the present disclosure relates to methods and devices directed to prognosing or classifying a subject with breast cancer following endocrine treatment using biomarkers.

BACKGROUND

Despite significant improvements in the treatment of early estrogen receptor positive (ER+) breast cancer, there are ongoing clinical challenges. Targeted anti-endocrine therapies have reduced mortality over the last 30-40 years [1, 2], but ER+ disease, which comprises 80% of breast cancers, still leads to the majority of deaths from early breast cancer [3]. Multiparametric gene assays are used increasingly to guide clinical treatment decisions [4]. Most prognostic tests provide an estimate of relapse risk following the treatment for ER+ breast cancer, but still lack predictive value for novel targeted treatment options [2, 4]. These multiparametric tests, which include OncotypeDx® (Genomic Health Inc.) [5,6], Prosigna™ (NanoString Technologies, Inc.) [7-9], Mammaprint® (Agendia Inc.) [10, 11], Breast Cancer Index (BioTheranostics Inc.) [12, 13], and EndoPredict (Sividon Diagnostics GmbH) [14], all provide broadly similar clinical utility [15, 16]. Although each is derived from RNA abundance studies, there are surprisingly few overlapping genes between different RNA signatures [17]. Prat et al., demonstrated in silico that combined signatures may more accurately predict outcome; leading to greater clinical significance [18]. Nonetheless, despite a decade of development of multiple residual risk signatures, progress towards stratified or targeted medicine has not been markedly accelerated by these tests. None of the existing tests have identified actionable targets which might form the basis for the next generation of stratified medicine approaches.

SUMMARY OF INVENTION

In an aspect, there is provided a method of prognosing endocrine-only treatment in a subject with breast cancer, the method comprising: a) providing a tumor sample of the breast cancer; b) determining the expression level of at least 40 of the genes listed in Table 4 in the tumor sample; c) comparing said expression levels to a reference expression level of the group of genes from control samples from a cohort of subjects; and d) determining the residual risk associated with the breast cancer; wherein a statistically significant difference or similarity in the expression of the group of genes compared to the reference expression level corresponds to a residual risk associated with breast cancer.

In an aspect, there is provided a computer-implemented method of prognosing endocrine-only treatment in a subject with breast cancer, the method comprising: a) receiving, at at least one processor, data reflecting the expression level of at least 40 of the genes listed in Table 4 in the tumor sample; b) constructing, at the at least one processor, an expression profile corresponding to the expression levels; c) comparing, at the at least one processor, said expression levels to a reference expression level of the group of genes from control samples from a cohort of subjects; d) determining, at the at least one processor, the residual risk associated with the breast cancer; wherein a statistically significant difference or similarity in the expression of the group of genes compared to the reference expression level corresponds to a residual risk associated with breast cancer.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided computer readable medium having stored thereon a data structure for storing the computer program product described herein.

In an aspect, there is provided a device for prognosing or classifying a subject with breast cancer and treated with endocrine therapy, the device comprising: at least one processor; and electronic memory in communication with the at one processor, the electronic memory storing processor-executable code that, when executed at the at least one processor, causes the at least one processor to: a) receive data reflecting the expression level of at least 40 of the genes listed in Table 4 in the tumor sample; b) construct an expression profile corresponding to the expression levels; c) compare said expression levels to a reference expression level of the group of genes from control samples from a cohort of subjects; and d) determining, at the at least one processor, the residual risk associated with the breast cancer wherein a statistically significant difference or similarity in the expression of the group of genes compared to the reference expression level corresponds to a residual risk associated with breast cancer.

In an aspect, there is provided a method of treating a subject with breast cancer, comprising: a) determining the residual risk of a subject according to the method described herein; and b) selecting a treatment based on said residual risk, and preferably treating the subject according to the treatment. In some embodiments, a combination endocrine therapy and chemotherapy is selected as treatment if said patient has a relatively high residual risk in relation to the population median of a reference cohort.

In an aspect, there is provided a composition comprising a plurality of isolated nucleic acid sequences, wherein each isolated nucleic acid sequence hybridizes to: (a) the mRNA of a group of genes corresponding to at least 40 of the genes listed in Table 4; and/or (b) a nucleic acid complementary to a), wherein the composition is used to measure the level of expression of the group of genes.

In an aspect, there is provided an array comprising one or more polynucleotide probes complementary and hybridizable to an expression product of at least 40 of the genes listed in Table 4.

In an aspect, there is provided a kit comprising reagents for detecting mRNA from a sample of a breast cancer tumour of at least one at least 40 of the genes listed in Table 4.

Other aspects and features of the present disclosure will become apparent to those ordinarily skilled in the art upon review of the following description of specific embodiments in conjunction with the accompanying figures.

BRIEF DESCRIPTION OF FIGURES

Embodiments of the present disclosure will now be described, by way of example only, with reference to the attached Figures.

FIG. 1A) Survival curves based on the prognostic model including nodal status applied to the validation cohort of patients receiving only endocrine therapy. FIG. 1B) Risk score estimates shown in A grouped as quartiles with each group compared against Q1. Hazard ratios were estimated using Cox proportional hazards model and significance of survival difference was estimated using the log-rank test. FIG. 1C) Distribution of patient risk scores in the TEAM Validation cohort showing the predicted 5 year recurrence probabilities (solid line) and 95% Cl (dashed lines bounding shaded area) as a function of patient risk score. Vertical dashed black line indicates training set median risk score. FIG. 1D) Distribution of patient risk scores in the TEAM Validation cohort showing the predicted 10 year recurrence probabilities (solid line) and 95% Cl (dashed lines bounding shaded area) as a function of patient risk score. Vertical dashed black line indicates training set median risk score.

FIG. 3A) Summary of REACTOME interactions amongst the genes of the 95-Gene Residual Risk Signature. Six major interaction modules comprising 52 genes were identified from the 95-Gene Residual Risk Signature. Relationships between genes, between and within modules, are shown by connecting lines. Solid lines with arrows indicate known and direct positive relationships. Solid lines ending in a perpendicular line indicate a known negative regulatory relationship. Dotted lines indicate relationships linked by other genes. Genes with red circles indicate gene targets for which there are known targeted therapies or at phase II/III development based on the Integrity compound search tool (Thompson Reuters) and ClinicalTrials.gov (https://clinicaltrials.gov/). FIG. 3B-3G) Kaplan Meier curves survival curves (left) for each module are shown, and representing the validation cohort. To the right of each Kaplan Meier curve are risk score estimates grouped as quartiles with each group compared against Q1. Hazard ratios were estimated using Cox proportional hazards model and significance of survival difference was estimated using the log-rank test. All patients represented are those who only received endocrine treatment.

FIG. 6A-6D illustrates Kaplan Meier Curves for model comparison in the validation cohort. A) Kaplan Meier survival curves based on the prognostic modeling for the 95-gene residual risk signature modeled without clinical covariates and representing patients receiving only endocrine therapy. B) Risk score estimates shown in A grouped as quartiles with each group compared against Q1. Hazard ratios were estimated using Cox proportional hazards model and significance of survival difference was estimated using the log-rank test. C) Kaplan Meier survival curves based on the prognostic modeling for the 95-gene residual risk signature modeled with clinical covariates including age, grade, pathological tumor size and nodal status; and representing patients receiving only endocrine therapy. D) Risk score estimates shown in C grouped as quartiles with each group compared against Q1. Hazard ratios were estimated using Cox proportional hazards model and significance of survival difference was estimated using the log-rank test.

DETAILED DESCRIPTION

Figure 1A:
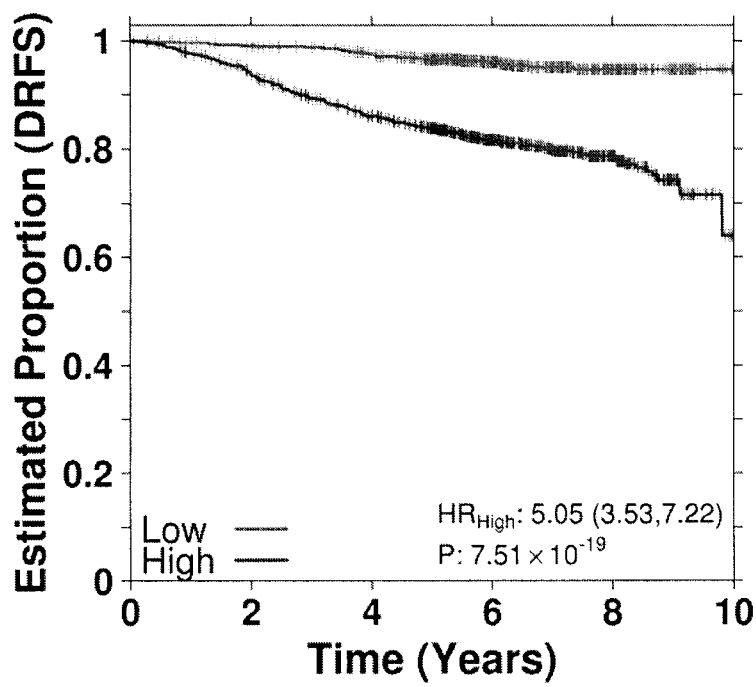
FIG. 1A-1D is a set of Kaplan Meier Survival Plots of the 95-Gene Residual Risk Signature in the TEAM Pathology Cohort.

Some women with hormone receptor positive early breast cancer can be managed effectively with endocrine therapies alone, whereas for others additional systemic chemotherapy treatment is necessary. The clinical challenges in managing high-risk women are to identify existing and novel drug targets, and to identify those who would benefit from these therapies.

Using the Tamoxifen and Exemestane Adjuvant Multinational Trial (TEAM) pathology cohort[19], comprised of 3,825 hormone-receptor positive (ER+ and/or PgR+) cases and including 477 (13%) HER2-positive cases, mRNA abundance analysis was performed to identify a gene signature, for example a 95-gene signature, of residual risk was identified and validated. The 95-gene signature is useful in improving risk stratification in the context of endocrine-treated patients. Moreover, this gene signature can be used to reveal potential drug targets, improving stratification in order to develop targeted therapies for such high-risk patients.

95 Gene Signature and Treatment

A panel of genes compiled from academic and commercial multiparametric tests as well as genes of importance to breast cancer pathogenesis, was used to profile 3,825 patients. A signature of 95 genes, including nodal status, was validated to stratify endocrine-treated patients into high- and low-risk groups based on distant relapse-free survival (DRFS; HR=5.05, 95% CI 3.53-7.22, $p=7.51 \times 10^{-22}$). This risk signature was also found to perform better than current multiparametric tests. When the 95-gene prognostic signature was applied to all patients in the validation cohort, including patients who received adjuvant chemotherapy, the signature remained prognostic (HR=4.76, 95% CI 3.56-6.2, $p=8.87 \times 10^{-28}$). Functional gene interaction analyses identified 6 significant modules representing pathways involved in cell cycle control, mitosis and receptor tyrosine signaling; containing a number of genes with existing targeted therapies for use in breast or other malignancies. Thus the identification of high-risk patients using this prognostic signature has the potential to also prioritize patients for treatment with these targeted therapies.

As will become apparent, preferred features and characteristics of one aspect of the invention are applicable to any other aspect of the invention. It should be noted that, as used herein, the singular form "a", "an" and "the" include plural references unless the context clearly dictates otherwise.

In an aspect, there is provided a method of prognosing endocrine-only treatment in a subject with breast cancer, the method comprising: a) providing a tumor sample of the breast cancer; b) determining the expression level of at least 40 of the genes listed in Table 4 in the tumor sample; c) comparing said expression levels to a reference expression level of the group of genes from control samples from a cohort of subjects; and d) determining a residual risk associated with the breast cancer; wherein a statistically significant difference or similarity in the expression of the group of genes compared to the reference expression level corresponds to the residual risk associated with breast cancer.

The term "subject" as used herein refers to any member of the animal kingdom, preferably a human being and most preferably a human being that has breast cancer or that is suspected of having breast cancer.

The term "sample" as used herein refers to any fluid, cell or tissue sample from a subject which can be assayed for biomarker expression products and/or a reference expression profile, e.g. peptides differentially present in a liquid biopsy.

The term "prognosis" as used herein refers to a clinical outcome group such as a worse survival group or a better survival group associated with a disease subtype which is reflected by a reference profile such as a biomarker reference expression profile or reflected by an expression level of the fifteen biomarkers disclosed herein. The prognosis provides an indication of disease progression and includes an indication of likelihood of death due to cancer. In one embodiment the clinical outcome class includes a better survival group and a worse survival group.

The term "prognosing or classifying" as used herein means predicting or identifying the clinical outcome group that a subject belongs to according to the subject's similarity to a reference profile or biomarker expression level associated with the prognosis. For example, prognosing or classifying comprises a method or process of determining whether an individual with breast cancer has a better or worse survival outcome, or grouping an individual with breast cancer into a better survival group or a worse survival group, or predicting whether or not an individual with breast cancer will respond to therapy.

The term "gene" as used herein means a polynucleotide which may include coding sequences, intervening sequences and regulatory elements controlling transcription and/or translation. Genes include normal alleles of the gene encoding polymorphisms, including silent alleles having no effect on the amino acid sequence of the gene's encoded polypeptide as well as alleles leading to amino acid sequence variants of the encoded polypeptide that do not substantially affect its function. These terms also may optionally include alleles having one or more mutations which affect the function of the encoded polypeptide's function.

The phrase "determining the expression of biomarkers" as used herein refers to determining or quantifying RNA or proteins or protein activities or protein-related metabolites expressed by the biomarkers. The term "RNA" includes mRNA transcripts, and/or specific spliced or other alternative variants of mRNA, including anti-sense products. The term "RNA product of the biomarker" as used herein refers to RNA transcripts transcribed from the biomarkers and/or specific spliced or alternative variants. In the case of "protein", it refers to proteins translated from the RNA transcripts transcribed from the biomarkers. The term "protein product of the biomarker" refers to proteins translated from RNA products of the biomarkers.

The term "level of expression" or "expression level" as used herein refers to a measurable level of expression of the products of biomarkers, such as, without limitation, the level of micro-RNA, messenger RNA transcript expressed or of a specific exon or other portion of a transcript, the level of proteins or portions thereof expressed of the biomarkers, the number or presence of DNA polymorphisms of the biomarkers, the enzymatic or other activities of the biomarkers, and the level of specific metabolites.

The term "differentially expressed" or "differential expression" as used herein refers to a difference in the level of expression of the biomarkers that can be assayed by measuring the level of expression of the products of the biomarkers, such as the difference in level of mRNA or a portion thereof expressed. In a preferred embodiment, the difference is statistically significant. The term "difference in the level of expression" refers to an increase or decrease in the measurable expression level of a given biomarker, for example as measured by the amount of mRNA as compared with the measurable expression level of a given biomarker in a control.

In certain embodiments, the group of genes is at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 of the genes listed in Table 4.

In some embodiments, the method further comprises building a subject gene expression profile from the determined expression levels of the group of genes.

In some embodiments, determining the residual risk comprises determining a module dysregulation score (MDS) comprising the sum of weights of the group of genes multiplied to a scaled mRNA abundance. In some embodiments, a high MDS score is associated with higher residual risk and/or worse survival and wherein a low MDS score is associated lower residual risk and/or better survival.

As used herein, "overall survival" refers to the percentage of or length of time that people in a study or treatment group are still alive following from either the date of diagnosis or the start of treatment for a disease, such as cancer. In a clinical trial, measuring the overall survival is one way to see how well a new treatment works.

As used herein, "relapse-free survival" refers to, in the case of cancer, the percentage of or length of time that people in a study or treatment group survive without any signs or symptoms of that cancer after primary treatment for that cancer. In a clinical trial, measuring the relapse-free survival is one way to see how well a new treatment works. It is defined as any disease recurrence (local, regional, or distant).

The term "good survival" or "better survival" as used herein refers to an increased chance of survival as compared to patients in the "poor survival" group. For example, the biomarkers of the application can prognose or classify patients into a "good survival group". These patients are at a lower risk of death after surgery.

The term "poor survival" or "worse survival" as used herein refers to an increased risk of death as compared to patients in the "good survival" group. For example, biomarkers or genes of the application can prognose or classify patients into a "poor survival group". These patients are at greater risk of death or adverse reaction from disease or surgery, treatment for the disease or other causes.

In some embodiments, the method further comprises normalizing said mRNA abundance using at least one control, preferably a plurality of controls.

In some embodiments, at least one of the plurality of controls comprises mRNA abundance of reference genes of a reference subject or the subject.

A "control population" refers to a defined group of individuals or a group of individuals with or without cancer, and may optionally be further identified by, but not limited to geographic, ethnic, race, gender, one or more other conditions or diseases, and/or cultural indices. In most cases a control population may encompass at least 10, 50, 100, 1000, or more individuals.

"Positive control data" encompasses data representing levels of RNA encoded by a target gene of the invention in each of one or more subjects having cancer of the invention, and encompasses a single data point representing an average level of RNA encoded by a target gene of the invention in a plurality of subjects having cancer of the invention.

"Negative control data" encompasses data representing levels of RNA encoded by a target gene of the invention in each of one or more subjects not having cancer of the invention, and encompasses a single data point representing an average level of RNA encoded by a target gene of the invention in a plurality of subjects having cancer of the invention.

The probability that test data "corresponds" to positive control data or negative control data refers to the probability that the test data is more likely to be characteristic of data obtained in subjects having breast cancer than in subjects not breast cancer, or is more likely to be characteristic of data obtained in subjects not having breast cancer or response to treatment than in subjects having breast cancer response to treatment, respectively.

In some embodiments, the method further comprises comparing a clinical indicator of the subject to a plurality of reference clinical indicators, wherein the clinical indicator comprises at least one of age, tumor grade, pathological tumor size or nodal status, preferably nodal status, and fitting these clinical indicators on the MDS, preferably using a multivariate Cox proportional hazards model.

Patients with a high risk prognosis therefore may benefit from more aggressive therapy, e.g. adjuvant therapy, in addition to hormone therapy. Adjuvant therapy may include chemotherapy, radiation therapy, hormone therapy, targeted therapy, or biological therapy.

In some embodiments, the method further comprises treating the subject with combined endocrine therapy and chemotherapy if the subject has a relatively high residual risk in relation to the population median of a reference cohort.

In some embodiments, the breast cancer is hormone receptor positive (ER+).

In some embodiments, the expression levels are determined using NanoString®.

In some embodiments, the residual risk represents distant relapse-free survival.

In an aspect, there is provided a method of treating a subject with breast cancer, comprising: a) determining the residual risk of a subject according to the method described herein; and b) selecting a treatment based on said residual risk, and preferably treating the subject according to the treatment. In some embodiments, a combination endocrine therapy and chemotherapy is selected as treatment if said patient has a relatively high residual risk in relation to the population median of a reference cohort.

Devices and Systems

In an aspect, there is provided a computer-implemented method of prognosing endocrine-only treatment in a subject with breast cancer, the method comprising: a) receiving, at at least one processor, data reflecting the expression level of at least 40 of the genes listed in Table 4 in the tumor sample; b) constructing, at the at least one processor, an expression profile corresponding to the expression levels; c) comparing, at the at least one processor, said expression levels to a reference expression level of the group of genes from control samples from a cohort of subjects; d) determining, at the at least one processor, a residual risk associated with the breast cancer; wherein a statistically significant difference or similarity in the expression of the group of genes compared to the reference expression level corresponds to the residual risk associated with breast cancer.

As used herein, "processor" may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof.

As used herein "memory" may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Portions of memory 102 may be organized using a conventional filesystem, controlled and administered by an operating system governing overall operation of a device.

As used herein, "computer readable storage medium" (also referred to as a machine-readable medium, a processor-readable medium, or a computer usable medium having a computer-readable program code embodied therein) is a medium capable of storing data in a format readable by a computer or machine. The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The computer readable storage medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the computer readable storage medium. The instructions stored on the computer readable storage medium can be executed by a processor or other suitable processing device, and can interface with circuitry to perform the described tasks.

As used herein, "data structure" a particular way of organizing data in a computer so that it can be used efficiently. Data structures can implement one or more particular abstract data types (ADT), which specify the operations that can be performed on a data structure and the computational complexity of those operations. In comparison, a data structure is a concrete implementation of the specification provided by an ADT.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

In some embodiments, the processor determines the residual risk by calculating a module dysregulation score (MDS) comprising the sum of weights of the group of genes multiplied to the scaled mRNA abundance.

In some embodiments, a high MDS score is associated with higher residual risk and/or worse survival and wherein a low MDS score is associated lower residual risk and/or better survival.

In some embodiments, the processor further normalizes said mRNA abundance using at least one control, preferably a plurality of controls.

In some embodiments, at least one of the plurality of controls comprises mRNA abundance of reference genes of a reference subject or the subject.

In some embodiments, the processor further compares a clinical indicator of the subject to a plurality of reference clinical indicators, wherein the clinical indicator comprises at least one of age, tumor grade, pathological tumor size or nodal status, preferably nodal status, and fits these clinical indicators on the MDS, preferably using a multivariate Cox proportional hazards model.

In some embodiments, the method further comprises outputting a suggestion for treating the subject with combined endocrine therapy and chemotherapy if the subject has a relatively high residual risk in relation to the population median of a reference cohort.

In some embodiments, the breast cancer is hormone receptor positive (ER+).

In some embodiments, the residual risk represents distant relapse-free survival.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided computer readable medium having stored thereon a data structure for storing the computer program product described herein.

In an aspect, there is provided a device for prognosing or classifying a subject with breast cancer and treated with endocrine therapy, the device comprising: at least one processor; and electronic memory in communication with the at one processor, the electronic memory storing processor-executable code that, when executed at the at least one processor, causes the at least one processor to: a) receive data reflecting the expression level of at least 40 of the genes listed in Table 4 in the tumor sample; b) construct an expression profile corresponding to the expression levels; c) compare said expression levels to a reference expression level of the group of genes from control samples from a cohort of subjects; and d) determining, at the at least one processor, a residual risk associated with the breast cancer wherein a statistically significant difference or similarity in the expression of the group of genes compared to the reference expression level corresponds to the residual risk associated with breast cancer.

Diagnostic Reagents

In an aspect, there is provided a composition comprising a plurality of isolated nucleic acid sequences, wherein each isolated nucleic acid sequence hybridizes to: (a) the mRNA of a group of genes corresponding to at least 40 of the genes listed in Table 4; and/or (b) a nucleic acid complementary to a), wherein the composition is used to measure the level of expression of the group of genes.

In an aspect, there is provided an array comprising one or more polynucleotide probes complementary and hybridizable to an expression product of at least 40 of the genes listed in Table 4.

In an aspect, there is provided a kit comprising reagents for detecting mRNA from a sample of a breast cancer tumour of at least one at least 40 of the genes listed in Table 4.

Examples of primers include an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature. A primer must be sufficiently long to prime the synthesis of extension products in the presence of an agent for polymerase. A typical primer contains at least about 5 nucleotides in length of a sequence substantially complementary to the target sequence, but somewhat longer primers are preferred. A primer will always contain a sequence substantially complementary to the target sequence, that is the specific sequence to be amplified, to which it can anneal.

The terms "complementary" or "complement thereof", as used herein, refer to sequences of polynucleotides which are capable of forming Watson & Crick base pairing with another specified polynucleotide throughout the entirety of the complementary region. This term is applied to pairs of polynucleotides based solely upon their sequences and does not refer to any specific conditions under which the two polynucleotides would actually bind The term "probe" refers to a molecule which can detectably distinguish between target molecules differing in structure, such as allelic variants. Detection can be accomplished in a variety of different ways but preferably is based on detection of specific binding. Examples of such specific binding include antibody binding and nucleic acid probe hybridization.

The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The polynucleotide compositions can be primers, can be cDNA, can be RNA, can be DNA complementary to target cDNA or a portion thereof, genomic DNA, unspliced RNA, spliced RNA, alternately spliced RNA, synthetic forms, and mixed polymers, both sense and antisense strands, and may be chemically or biochemically modified or may contain non-natural or derivatized nucleotide bases, as will be readily appreciated by those skilled in the art.

Where nucleic acid includes RNA, reference to the sequence shown should be construed as reference to the RNA equivalent, with U substituted for T.

The methods of nucleic acid isolation, amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Moller, R. Beynon, C. Howe, Springer Verlag; 1st edition (Oct. 15, 2000), ISBN: 0387916008.

Examples of amplification techniques include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in European Patent Appl. 320 308; gap filling ligase chain reaction amplification, as disclosed in U.S. Pat. No. 5,427,930; and RNA transcription-free amplification, as disclosed in U.S. Pat. No. 6,025,134.

"Kit" refers to a combination of physical elements, e.g., probes, including without limitation specific primers, labeled nucleic acid probes, antibodies, protein-capture agent(s), reagent(s), instruction sheet(s) and other elements useful to practice the invention, in particular to identify the levels of particular RNA molecules in a sample. These physical elements can be arranged in any way suitable for carrying out the invention. For example, probes and/or primers can be provided in one or more containers or in an array or microarray device.

In one embodiment, levels of RNA encoded by a target gene can be determined in one analysis. A combination kit may therefore include primers capable of amplifying cDNA derived from RNA encoded by different target genes. The primers may be differentially labeled, for example using different fluorescent labels, so as to differentiate between RNA from different target genes.

Multiplex, such as duplex, real-time RT-PCR enables simultaneous quantification of 2 targets in the same reaction, which saves time, reduces costs, and conserves samples. These advantages of multiplex, real-time RT-PCR make the technique well-suited for high-throughput gene expression analysis. Multiplex qPCR assay in a real-time format facilitates quantitative measurements and minimizes the risk of false-negative results. It is essential that multiplex PCR is optimized so that amplicons of all samples are compared insub-plateau phase of PCR. Yun, Z., I. Lewensohn-Fuchs, P. Ljungman, L. Ringholm, J. Jonsson, and J. Albert. 2003. A real-time TaqMan PCR for routine quantitation of cytomegalovirus DNA in crude leukocyte lysates from stem cell transplant patients. J. Virol. Methods 110:73-79. [PubMed]. Yun, Z., I. Lewensohn-Fuchs, P. Ljungman, and A. Vahlne. 2000. Real-time monitoring of cytomegalovirus infections after stem cell transplantation using the TaqMan polymerase chain reaction assays. Transplantation 69:1733-1736. [PubMed]. Simultaneous quantification of up to 2, 3, 4, 5, 6, 7, and 8 or more targets may be useful.

For example, the primers and probes contained within the kit may include those able to recognize any of genes of the 95 gene signature described herein.

A primer which "selectively hybridizes" to a target polynucleotide is a primer which is capable of hybridizing only, or mostly, with a single target polynucleotide in a mixture of polynucleotides consisting of RNA in a sample, or consisting of cDNA complementary to RNA within the sample.

A gene expression profile for breast cancer found in a sample at the RNA level of one or more genes comprising, but preferably not limited to, any of the 95 genes described herein, can be identified or confirmed using many techniques, including but preferably not limited to PCR methods, as for example discussed further in the working examples herein, Northern analyses and the microarray technique, NanoString® and quantitative sequencing. This gene expression profile can be measured in a sample, using various techniques including e.g. microarray technology. In an embodiment of this method, fluorescently labeled cDNA probes may be generated through incorporation of fluorescent nucleotides by reverse transcription of RNA extracted from a sample. Labeled cDNA probes applied to the chip hybridize with specificity to each spot of DNA on the array. Quantitation of hybridization of each arrayed element allows for assessment of corresponding mRNA abundance. For example, with dual color fluorescence, separately labeled cDNA probes generated from two sources of RNA are hybridized pair wise to the array. The relative abundance of the transcripts from the two sources corresponding to each specified gene is thus determined simultaneously. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106-149 (1996)). Microarray analysis can be performed by commercially available equipment, following manufacturer's protocols, such as by using the Affymetrix GenChip technology, or Incyte's microarray technology.

In the present description, for purposes of explanation, numerous details are set forth in order to provide a thorough understanding of the embodiments. However, it will be apparent to one skilled in the art that these specific details are not required. For example, specific details are not provided as to whether the embodiments described herein are implemented as a software routine, hardware circuit, firmware, or a combination thereof.

The above listed aspects and/or embodiments may be combined in various combinations as appreciated by a person of skill in the art. The advantages of the present disclosure are further illustrated by the following examples. The examples and their particular details set forth herein are presented for illustration only and should not be construed as a limitation on the claims of the present invention.

EXAMPLES

Materials and Methods

Figure 11A:
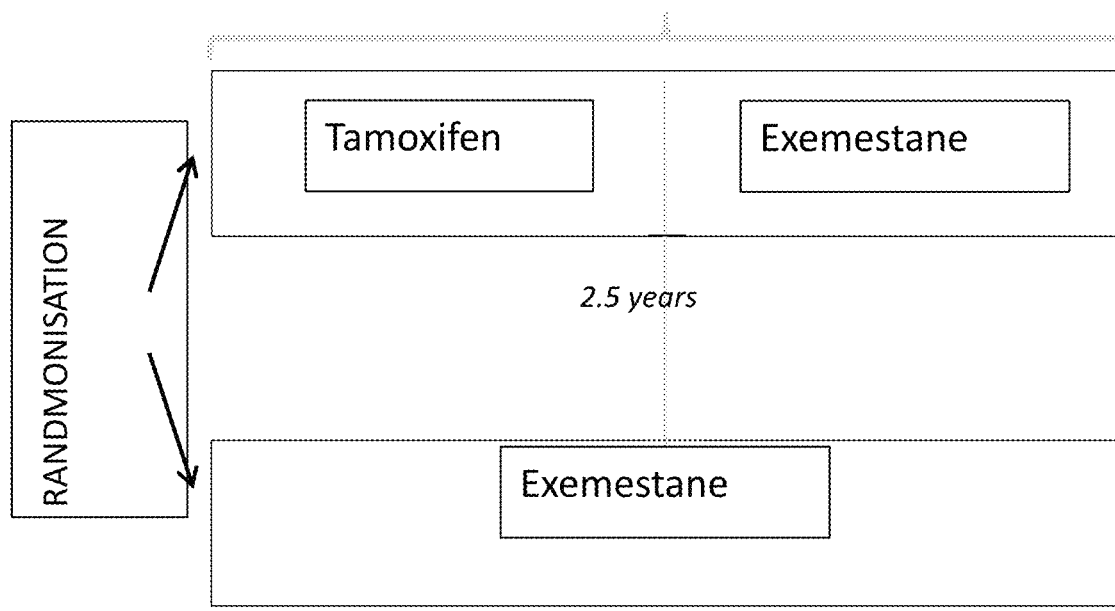
FIG. 11A-11C illustrates TEAM Trial Schema and Patient Samples. A) Trial schema for the Tamoxifen and Exemestane Adjuvant Multinational Trial (TEAM) pathology cohort. Eligible patients were randomized to receive either Tamoxifen for 2.5 years followed by Exemestane for the remaining 2.5 years; or Exemestane for 5 years. B) Summary of statistical power in the TEAM cohort. C) Summary of samples collected and processed for the current study.

The TEAM trial was a multinational, open-label, phase III trial in which postmenopausal women with hormone receptor-positive[19] early breast cancer were randomly assigned to receive Exemestane (25 mg) once daily, or Tamoxifen (20 mg) once daily for the first 2.5-3 years; followed by Exemestane (25 mg) (totaling 5 years of treatment) (see FIG. 11A). Hormone-receptor (ER and PgR) and HER2 status by immunohistochemistry were locally assessed for entry into the trial and then centrally confirmed[28], and HER2 status was confirmed by immunohistochemistry and fluorescence in situ hybridization (FISH)[29]. All assessment was performed according to ASCO/CAP guidelines[30-32]. None of the patients received anti-HER2 therapy. Distant relapse-free survival (DRFS) was defined as time from randomisation to distant relapse or death from breast cancer[19].

Figure 11B:
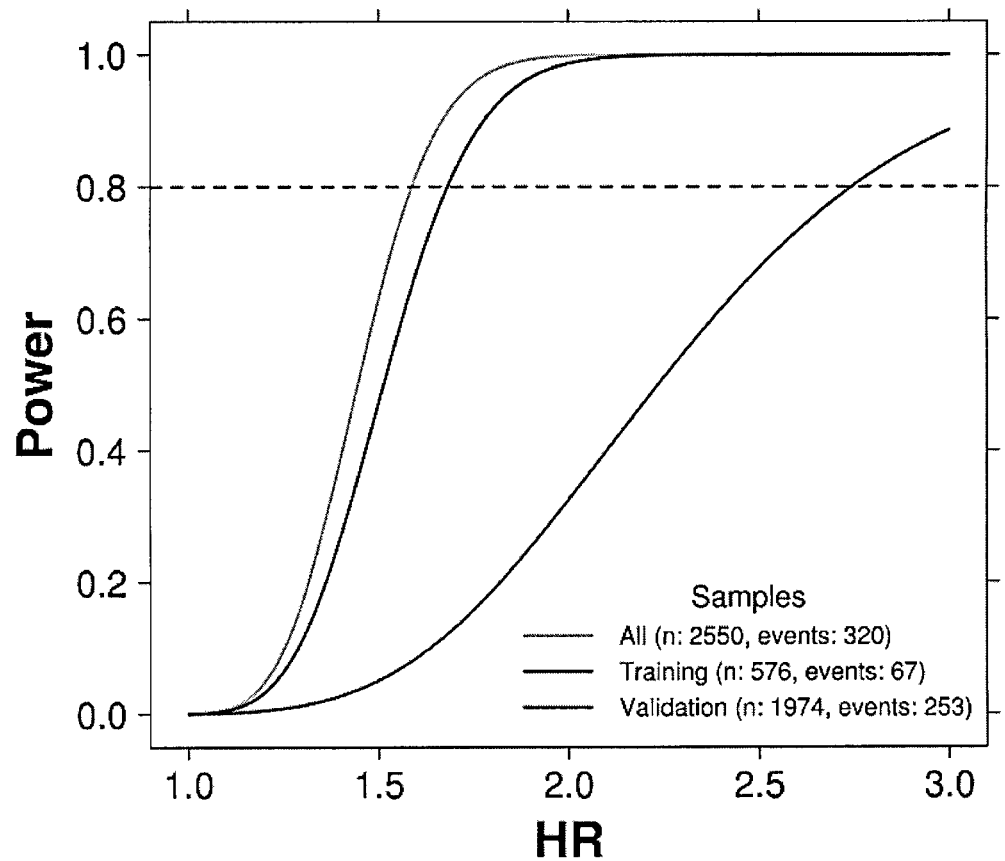
Figure 11C:
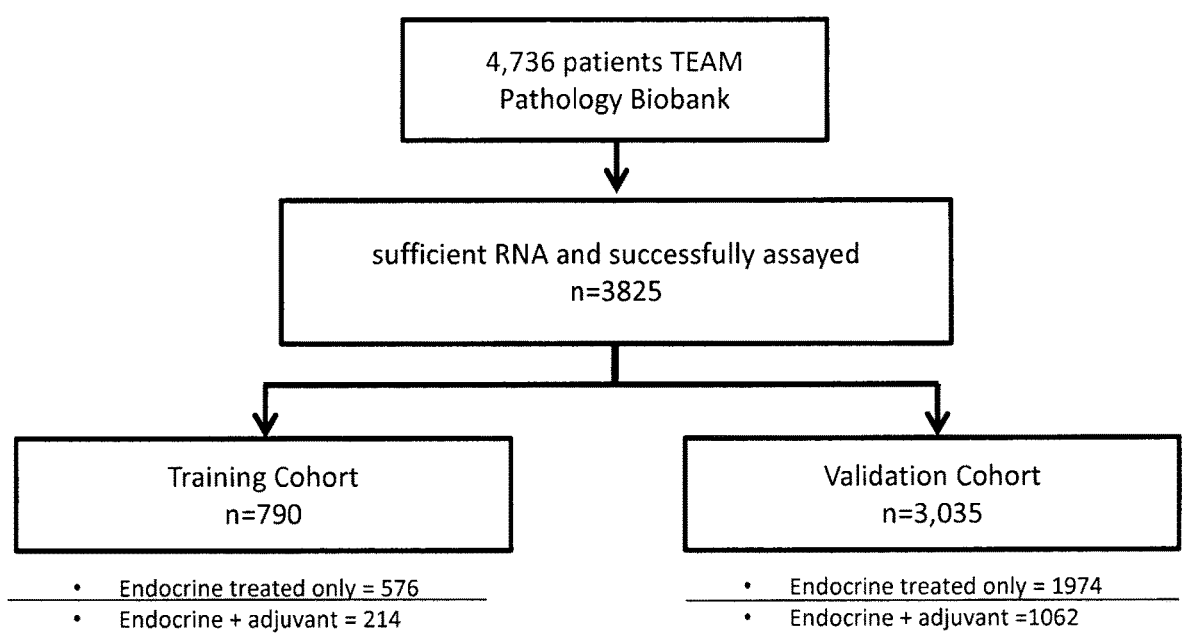

The TEAM trial included a pathology research study comprised of 4,736 patients from five countries with an average clinical follow-up of 6.86 years. Power analysis was performed to confirm the study size had 88.6% and 100% power to detect a HR of at least 3.0 in the training and validation cohorts respectively (see FIG. 11B). RNA was available and successfully assayed from 3,825 samples. Patients from the UK cohort were assigned as the training cohort (n=790); while the remaining patients from Germany, Belgium, Netherlands and Greece comprised a fully-independent validation cohort (n=3,035). All patients were assayed for mRNA abundance (see FIG. 11C). To identify a signature of residual risk following endocrine treatment only, the main analyses excluded those patients who received neo-adjuvant and adjuvant chemotherapy.

TEAM Cohort Power Calculations

To evaluate whether there was sufficient power to develop prognostic markers in this study, power calculations were performed for both endocrine-only cohort, as well as the endocrine+adjuvant chemotherapy cohort; the complete TEAM cohort (n=2549 and events=320; n=3,825 and events=507); and for each of the training (n=576 and events=67; n=790 and events=106) and validation (n=1973 and events=253; n=3,035 and events=431) subsets separately. Assuming equal-sized patient groups, power estimates representing the likelihood of observing a specific HR against the above-mentioned event numbers were derived using the formula (1) below [37]:

$$z_{power} = \frac{\sqrt{E} \times \ln(HR)}{2} - z\left(1 - \frac{\alpha}{2}\right) \quad (1)$$

where E represents the total number of events (DRFS) and a represents the significance level which was set to $10^{-3}$ to represent multiple testing adjustment. $z_{power}$ was calculated for HR ranging from 1 to 3 with steps of $0.01^{38}$ (Haider et al. submitted).

RNA Extraction and Expression Profiling

Five 4 μm formalin-fixed paraffin-embedded (FFPE) sections per case were deparaffinised, tumor areas were macrodissected and RNA extracted using the Ambion® Recoverall™ Total Nucleic Acid Isolation Kit-RNA extraction protocol (Life Technologies™, Ontario, Canada). RNA aliquots were quantified using a Nanodrop-8000 spectrophotometer (Delaware, USA). All 3825 RNAs extracted from the TEAM pathology cohort were successfully assayed. Probes for each gene were designed and synthesised at NanoString® Technologies (Seattle, Wash., USA); and 250 ng of RNA for each sample were hybridised, processed and analysed using the NanoString® nCounter® Analysis System, according to NanoString® Technologies protocols.

mRNA Abundance Analysis and Survival Modelling

Figure 12:
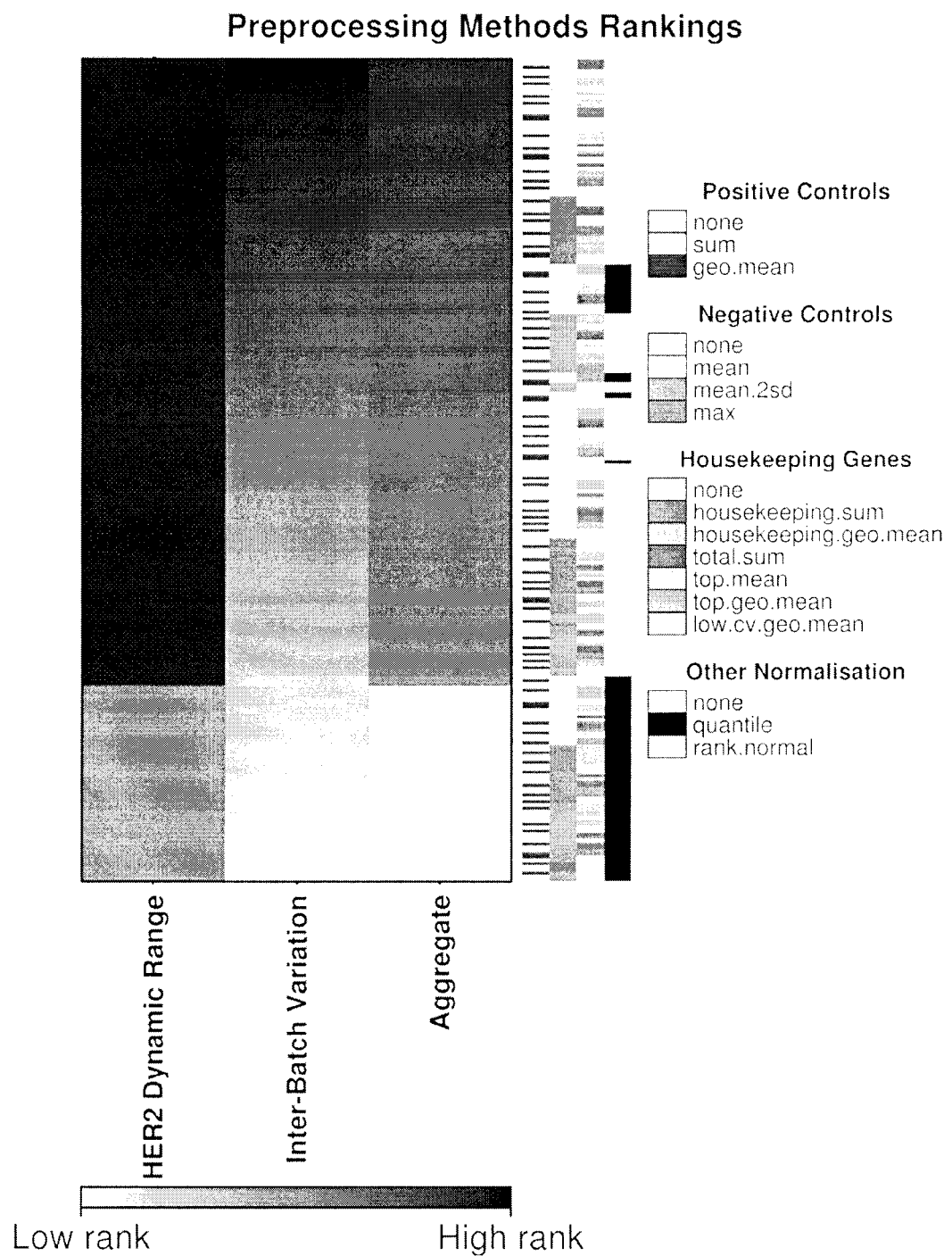
FIG. 12 illustrates pre-processing methods rankings of normalization strategies. Preprocessing TEAM cohort. Heatmap shows ranking of preprocessing methods based on their ability to maximise molecular differences between HER2+ve and HER2−ve profiles, while minimizing batch effects. For 252 combinations of preprocessing methods, two rankings were established as per above criteria, and subsequently aggregated using the rank product. The heatmap is sorted based on the aggregate rank with the most effective preprocessing parameters appearing at the top.

Raw mRNA abundance count data were pre-processed using the NanoStringNorm R package [33,39] (v1.1.19) using normalization factors derived from the geometric mean of the top expressing 75 genes. Samples with RNA content |z-score|>6 were flagged and removed as outliers. To assess the performance of the chosen normalization method in this cohort, a total of 252 combination of preprocessing methods were evaluated: spanning normalization methods that make use of six positive controls, eight negative controls and eight housekeeping genes (RPLP0, TFRC, MRPL19, SF3A1, GAPDH, PSMC4, ACTB, and GUS) followed by global normalization (see FIG. 12). To identify the most optimal preprocessing parameters, two criteria were assessed. Firstly, each preprocessing method was ranked based on their ability to maximize Euclidean distance of ERBB2 mRNA abundance between HER2-positive and HER2-negative samples. The process was repeated for 1 million random subsets of HER2-positive and HER2-negative samples for each of the preprocessing schemes. Secondly, each preprocessing method was evaluated and ranked based on their ability to minimize inter-batch variation by using 15 replicates of an RNA pool extracted from 5 randomly selected anonymized FFPE breast tumor samples. A mixed effects linear model was performed and residual estimates were used as an estimate of inter-batch variation (R package: nlme v3.1-117). Finally, cumulative ranks based on these two criteria were estimated based on RankProduct[40] of the two metrics. The final selection of an optimal pre-processing method was chosen based on the rank product, which normalizes the raw counts to the geometric mean derived from the top 75 expressing genes. Fourteen samples were removed as being potential outliers (having RNA content |z-score|>5 or low inter-array correlations). Fourteen samples were run in duplicates, and their raw counts were averaged and subsequently treated as a single sample prior to normalization. The method chosen was amongst the top 10 preprocessing methods in rank product (see FIG. 12).

Univariate survival analysis of preprocessed mRNA abundance data was performed by median-dichotomizing patients into high- and low-expression groups. Clinical variable age was modeled as binary (dichotomized around age 55), while grade and nodal status were modelled as ordinal variables, and pathological size was modeled as a continuous variable.

Network-Based Signature Derivation and Module Dysregulation Score

Feature-selection of genes was first performed based on univariate Cox proportional hazards modelling in the endocrine-treated only training cohort; those with p<0.25 were retained. These retained genes were used to calculate a "module-dysregulation score".

Module dysregulation scores (MDS) were calculated using the following process (Haider et al., submitted): 1) weights (β) of all evaluated genes were calculated by fitting a univariate Cox proportional hazards model based on the Training cohort only; and 2) these weights were then multiplied to the scaled mRNA abundance levels to estimate per-patient module dysregulation score as represented by formula (2):

$$MDS = \sum_{i=1}^{n} \beta X_i \quad (2)$$

Here, n represents the number of genes in a given module and $X_i$ represents the scaled (z-score) abundance of gene i. MDS for patients in the Validation cohort were generated using parameters estimated through the Training cohort.

A multivariate Cox proportional hazards model was then fit on MDSs, along with clinical covariates (age, grade, pathological size and nodal status); a stepwise backward selection approach using AIC was performed to refine the multivariate model. The final selected model was trained in the training cohort and validated in the fully independent validation cohort (see Table 1). DRFS truncated to 10 years was used as an end-point. Recurrence probabilities were estimated as described below. All survival modelling was performed on DRFS, in the R statistical environment with the survival package (v2.37-4). Model performances were evaluated through area under the receiver operating characteristic (ROC) curve (AUC).

TABLE 1

Clinical Characteristics of the Endocrine-Treated Patients

| | Training | | | | Validation | | | |
|---|---|---|---|---|---|---|---|---|
| | HR | 95% CI | P-value | N | HR | 95% CI | P-value | N |
| Age (<55) | 1.791 | 0.44-7.32 | 0.417 | 576 | 0.856 | 0.52-1.40 | 0.535 | 1974 |
| Nodal Status | | | | | | | | |
| 0 vs. 1-3 | 1.372 | 0.81-2.33 | 0.240 | 567 | 1.323 | 0.98-1.78 | 0.066 | 1925 |
| 0 vs. 4-9 | 3.314 | 1.46-7.53 | 0.004 | | 4.021 | 2.77-5.83 | $1.916 \times 10^{-13}$ | |
| 0 vs. 10+ | 4.973 | 1.75-14.10 | 0.003 | | 6.562 | 4.17-10.34 | $4.907 \times 10^{-16}$ | |
| Pathological Size (Categorical) | | | | | | | | |
| ≤2 vs. (>2 cm & ≤5 cm) | 1.953 | 1.19-3.20 | 0.008 | 576 | 2.148 | 1.63-2.83 | $5.765 \times 10^{-08}$ | 1972 |
| ≤2 vs. >5 | 3.096 | 0.94-10.17 | 0.063 | | 2.755 | 1.75-4.33 | $1.117 \times 10^{-5}$ | |
| Pathological Size (Continuous) | 1.163 | 1.06-1.27 | 0.001 | 560 | 1.311 | 1.21-1.42 | $9.401 \times 10^{-12}$ | 1963 |
| Grade | | | | | | | | |
| 1 vs. 2 | 1.835 | 0.56-5.99 | 0.315 | 563 | 1.433 | 0.90-2.29 | 0.131 | 1869 |
| 1 vs. 3 | 3.341 | 1.02-10.93 | 0.046 | | 2.606 | 1.64-4.15 | $5.452 \times 10^{-5}$ | |
| HER2 | 2.31 | 1.33-4.02 | 0.003 | 564 | 1.835 | 1.32-2.55 | $2.745 \times 10^{-4}$ | 1890 |

Recurrence Probability

Recurrence probabilities at 5- and 10-years were estimated by splitting the predicted risk-scores in 25 equal bins. For each bin, recurrence probability R(t) was calculated as 1-S(t), where S(t) is the Kaplan-Meier survival estimate at year 5 or year 10. A local polynomial regression was used to smooth the R(t) estimates of these 25 bin. The predicted estimates were then plotted against the median risk score of each group except the first and last group, where the lowest risk score and 99th percentile were used, respectively. All survival modelling was performed in the R statistical environment (R package: survival v 2.38-3).

Model Evaluation

Performance of survival models was evaluated using the area under the receiver operating characteristic (ROC) curve. A permutation analysis was performed to evaluate the significance of AUC differences across the different models (scores were shuffled 10,000 times while preserving the order of the survival objects).

Derivation of Commercially-Based and Academically-Based Risk Stratification Scores The derivation of similar risk classifications using genes comprising the following multi-parametric tests OncotypeDx® (Genomic Health Inc.)[5, 6], Prosigna™ (NanoString Technologies, Inc.)[7-9], Mammaprint® (Agendia Inc.)[10, 11].

mRNA-IHC4 Risk Score:

IHC4-protein model risk scores were calculated as described [41, 42] and adjusted for clinical covariates. ER10 scores were calculated by dividing ER histoscores by 30 and PgR10 scores were calculated by dividing the percent PgR staining by 10. A 10-fold cross validation approach was used to train the model and generate IHC4 RNA risk scores. An mRNA-IHC4 model was trained on mRNA abundance profiles of ESR1, PGR, ERBB2 and MKI67 in the training cohort using multivariate Cox proportional hazards modelling (Table 2). Model predictions (continuous risk scores) were grouped into quartiles and analysed using Kaplan-Meier analysis and multivariate Cox proportional hazards model adjusted for clinical variables as above.

OncotypeDX-Like Recurrence Score:

Data from the 16 test genes were normalized as previously described [43] and NanoString intensity values log 2 transformed to fit the 0-15 measurement range from the original publication. Unscaled recurrence scores were then calculated based on: $RS_U$=+0.47×GRB7 group score−0.34× ER group score+1.04× proliferation group score+0.10× invasion group score+0.05× CD68−0.08×GSTM1−0.07× BAG1; and finally the scores are scaled as previously described [43] Patients were then classified into high or low outcome groups based on a recurrence score of above or below 25, respectively; and modeled for DRFS.

Prosigna-Like Subtyping and Risk of Recurrence Score:

Samples were scored based on the method outlined by Parker et al.[44] and trained in the context of ER-positivity, using the 50 genes of the PAM50 gene list [45-47]. The "normal-like" subgroup was removed from the final subtyping classification. R scripts were obtained from the supplementary files [44] and scores were generated which were then modelled against DRFS.

MammaPrint-Like Risk Score:

Samples were scored based on the gene70 function of the genefu R package (v1.14.0). Derivation of low and high-risk categories were modelled according to van de Vijver et al. [48] and outcome based on DRFS.

Genomic Grade Index-Like Risk Modelling:

Samples were scored based on the procedure outlined in Toussaint et al.[49] using MYBL2, KPNA2, CDC2 and CDC20. Expression data was used to calculate average expression housekeeping genes (GUS, TBP, RPLPO and TFRC), which was used to normalize the expression of the four genes used to determine the GGI score. Patients were classified into low or high risk groups and modelled for DRFS. Genomic Grade Index [34]; in addition to IHC4 [35, 36] are described previously by Prat et al., [18] and in Table 2.

TABLE 2

Coefficients and P-values of mRNA-IHC4 Risk Model

| | exp(coef) | exp(−coef) | lower .95 | upper .95 |
|---|---|---|---|---|
| ESR1 | 1.03637 | 0.96490 | 0.88913 | 1.20801 |
| HER2 | 1.11903 | 0.89363 | 0.94665 | 1.32279 |
| PGR | 0.83413 | 1.19885 | 0.74507 | 0.93384 |
| MKI67 | 1.66025 | 0.60232 | 1.26213 | 2.18394 |

TABLE 2-continued

Coefficients and P-values of mRNA-IHC4 Risk Model

|  | coef | exp(coef) | se(coef) | z | Pr(>\|z\|) |
|---|---|---|---|---|---|
| ESR1 | 0.03573 | 1.03637 | 0.07819 | 0.45695 | 0.647705369 |
| HER2 | 0.11246 | 1.11903 | 0.08535 | 1.31762 | 0.187629665 |
| PGR | −0.18136 | 0.83413 | 0.05761 | −3.14801 | 0.001643889 |
| MKI67 | 0.50697 | 1.66025 | 0.13988 | 3.62424 | 0.000289815 |

Pathway Analyses Using Reactome

The final gene list was loaded into the Cytoscape Reactome Functional Interaction (FI) plugin in Cytoscape (v3.0.2). Symbols were loaded as a gene set with the 2013 version of the FI network. A FI network was constructed with FI annotations and no linker genes. Spectral clustering and Pathway Enrichment were computed for each module using the Reactome FI plugin functions.

Results

The RNA abundance profiles of all genes were generated for 3,825 patients. Of patients who had complete therapy information, 2,549 were treated with endocrine therapies alone, while 1,275 also received adjuvant chemotherapy. The endocrine-treated only patients were divided into a 576-patient training cohort (n=67 events), and a 1,973-patient validation cohort (n=253 events), which was used for signature discovery and validation, respectively. To test the prognostic ability of the signature, which was trained and validated in the endocrine-treated patients, to patients who were treated with adjuvant chemotherapy, the signature was then modeled against all patients in the validation cohort and adjusted for adjuvant chemotherapy (n=3,035). The median follow-up in each cohort was 7.51 and 6.21 years respectively. The clinical characteristics of the endocrine-treated training and validation cohorts are described in Table 1. The clinical characteristics of the entire cohort of 3,825 patients are summarized in Table 3. High tumor grade, nodal status, pathological size and HER2 IHC status were univariately prognostic in both training and validation cohorts (see Table 1 and Table 3).

Figure 1B:
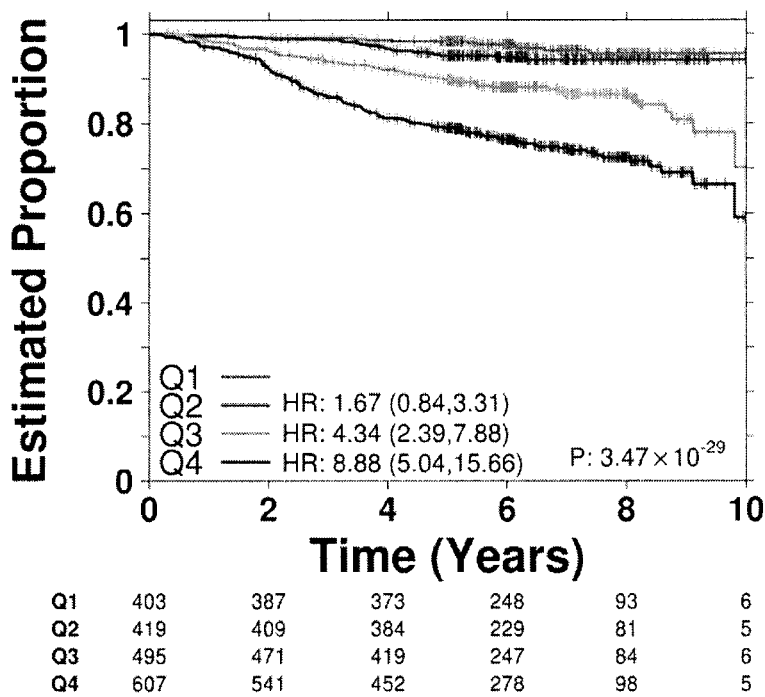
Figure 1C:
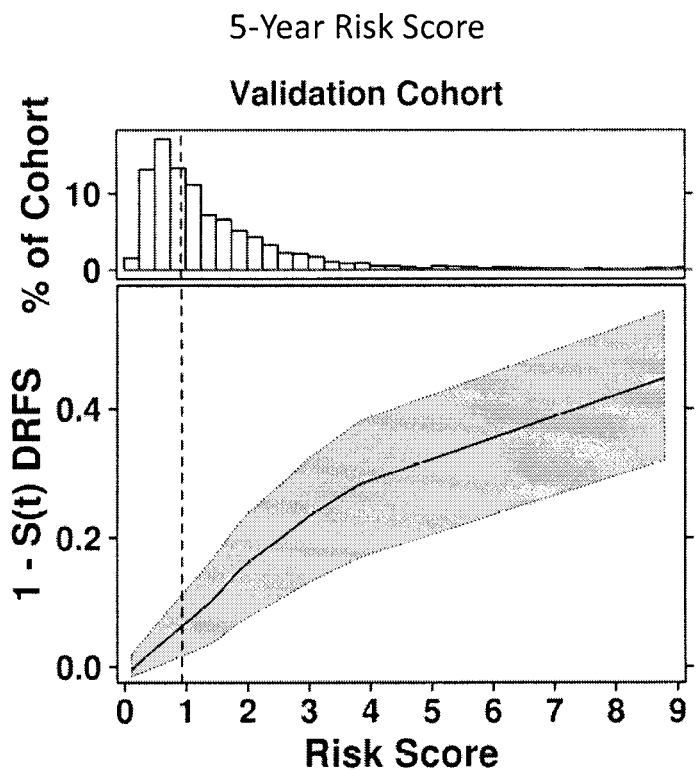
Figure 1D:
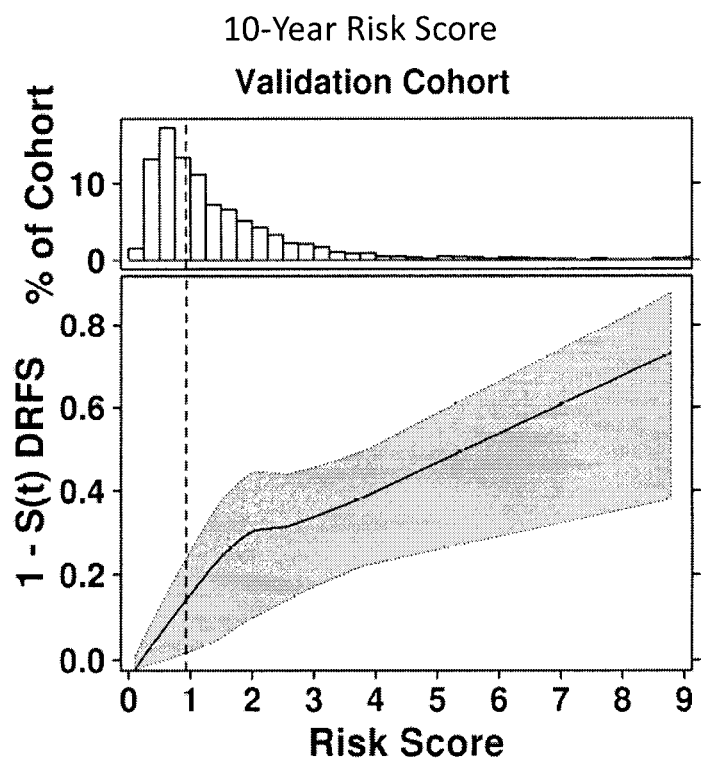
Figure 4:
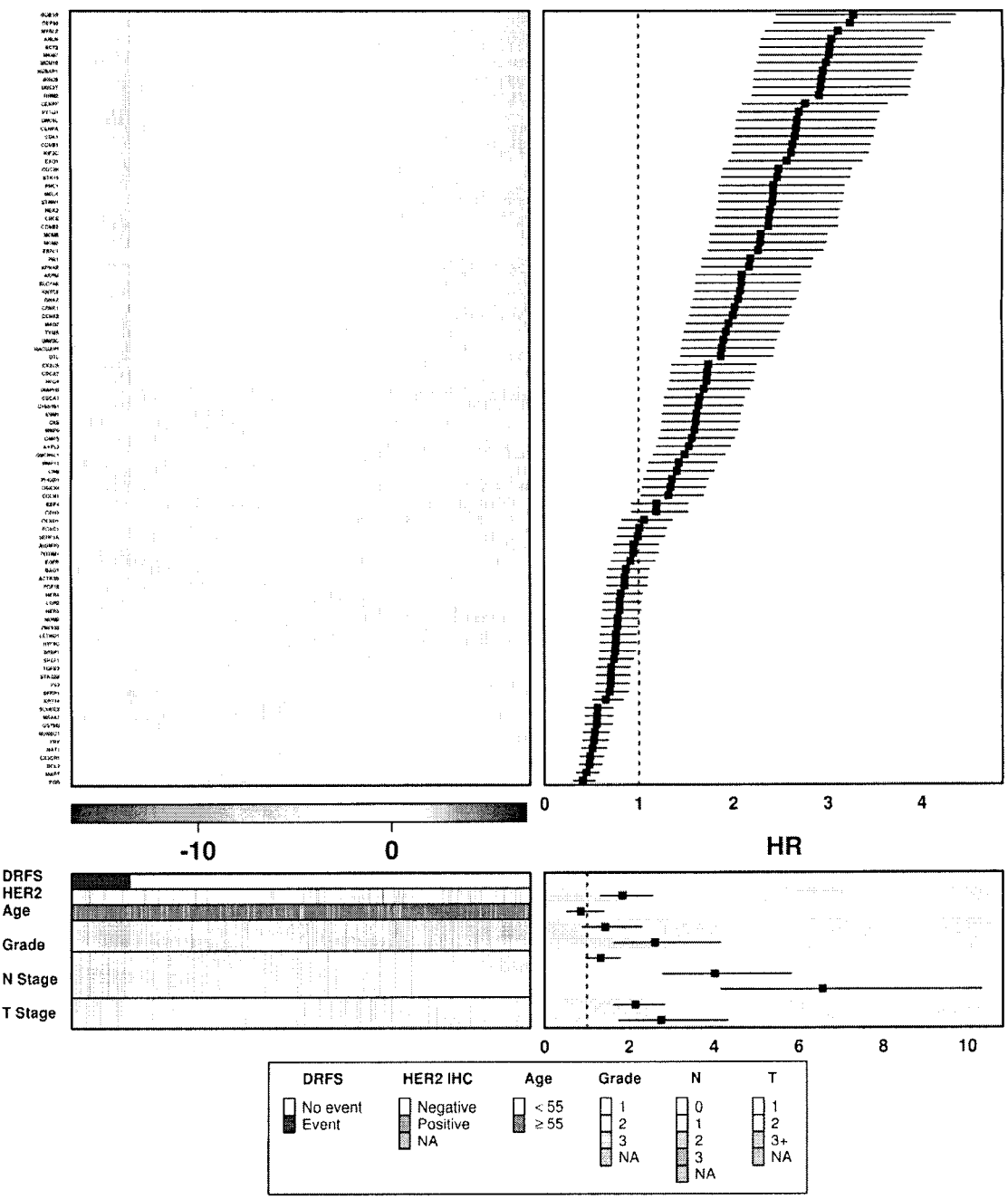
FIG. 4 illustrates univariate results of genes comprising the 95-gene residual risk signature. A heatmap shows the normalized and scaled mRNA abundance profiles of the 95 genes comprising the final residual risk signature, in the training cohort of endocrine-treated patients only. The 95 genes shown on the heatmap are listed in order as follows: BUB1B, CEP55, MYBL2, ANLN, ECT2, MKI67, MCM10, NUSAP1, BIRC5, UBE2T, RRM2, CENPF, PTTG1, ORC6L, CENPA, CDK1, CCNB1, KIF2C, EXO1, CDC20, STK15, PRC1, MELK, STMN1, NEK2, CDC6, CCNB2, MCM6, MCM2, ESPL1, Plk1, KPNA2, ASPM, SLC7AS, KNTC2, GNAZ, CCNE1, CCNE2, MAD2, TYMS, UBE2C, RACGAP1, DTL, CXXC5, CDCA7, RFC4, DIAPH3, CDCA1, C16ort61, ESM1, CK8, MMP9, GMPS, AYTL2, OSCN6L1, MMP11, LIN9.
Figures 5A, 5B:
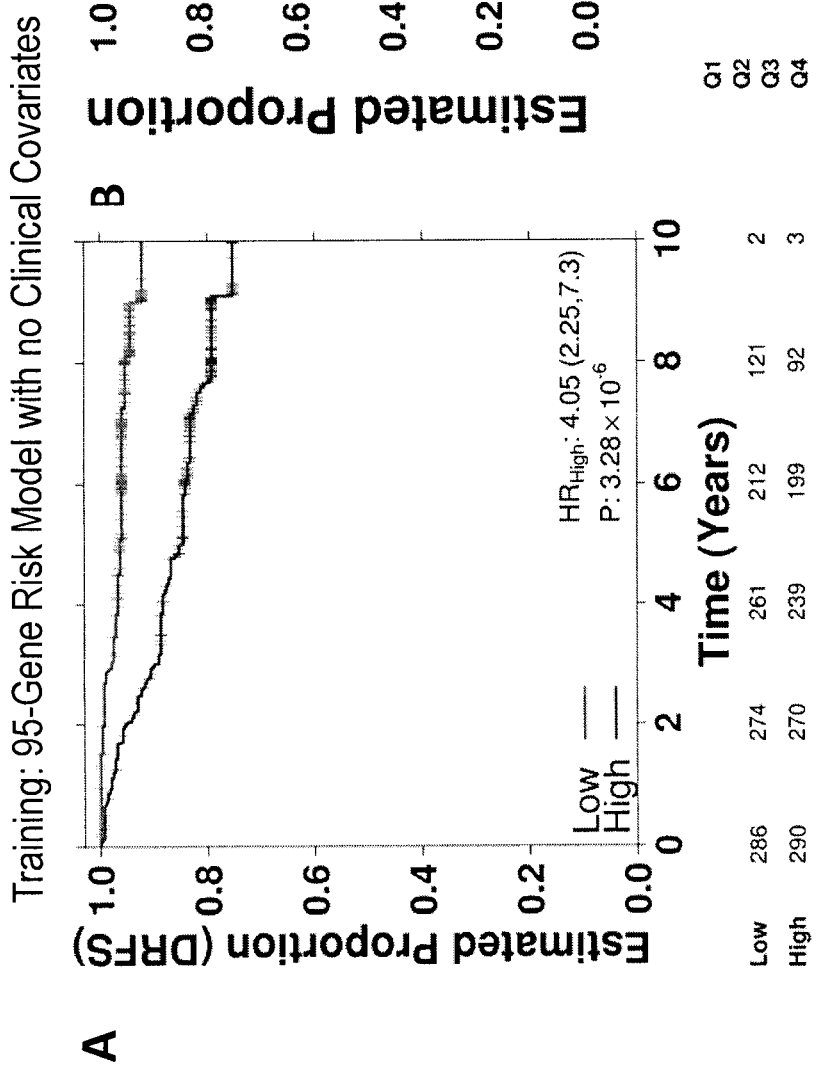
FIG. 5A-5F illustrates Kaplan Meier Curves for model comparison in the training cohort. A) Kaplan Meier survival curves based on the prognostic modeling for the 95-gene residual risk signature modeled without clinical covariates and representing patients receiving only endocrine therapy. B) Risk score estimates shown in A grouped as quartiles with each group compared against Q1. Hazard ratios were estimated using Cox proportional hazards model and significance of survival difference was estimated using the log-rank test. C) Kaplan Meier survival curves based on the prognostic modeling for the 95-gene residual risk signature modeled with clinical covariates including age, grade, pathological tumor size and nodal status; and representing patients receiving only endocrine therapy. D) Risk score estimates shown in C grouped as quartiles with each group compared against Q1. Hazard ratios were estimated using Cox proportional hazards model and significance of survival difference was estimated using the log-rank test. E) Kaplan Meier survival curves based on the prognostic modeling for the 95-gene residual risk signature modeled only with nodal status as the only clinical covariate among patients receiving only endocrine therapy. F) Risk score estimates shown in E grouped as quartiles with each group compared against Q1. Hazard ratios were estimated using Cox proportional hazards model and significance of survival difference was estimated using the log-rank test.
Figures 5C, 5D:
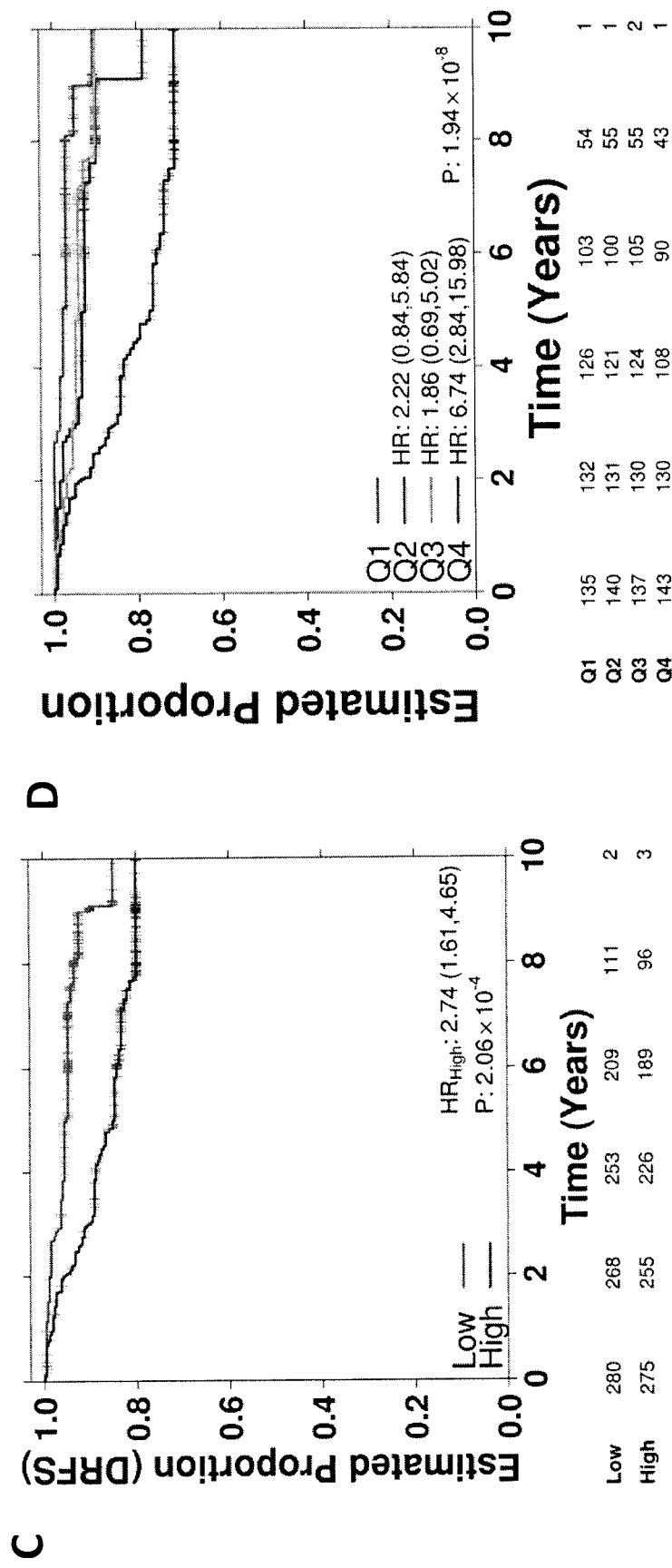
Figures 5E, 5F:
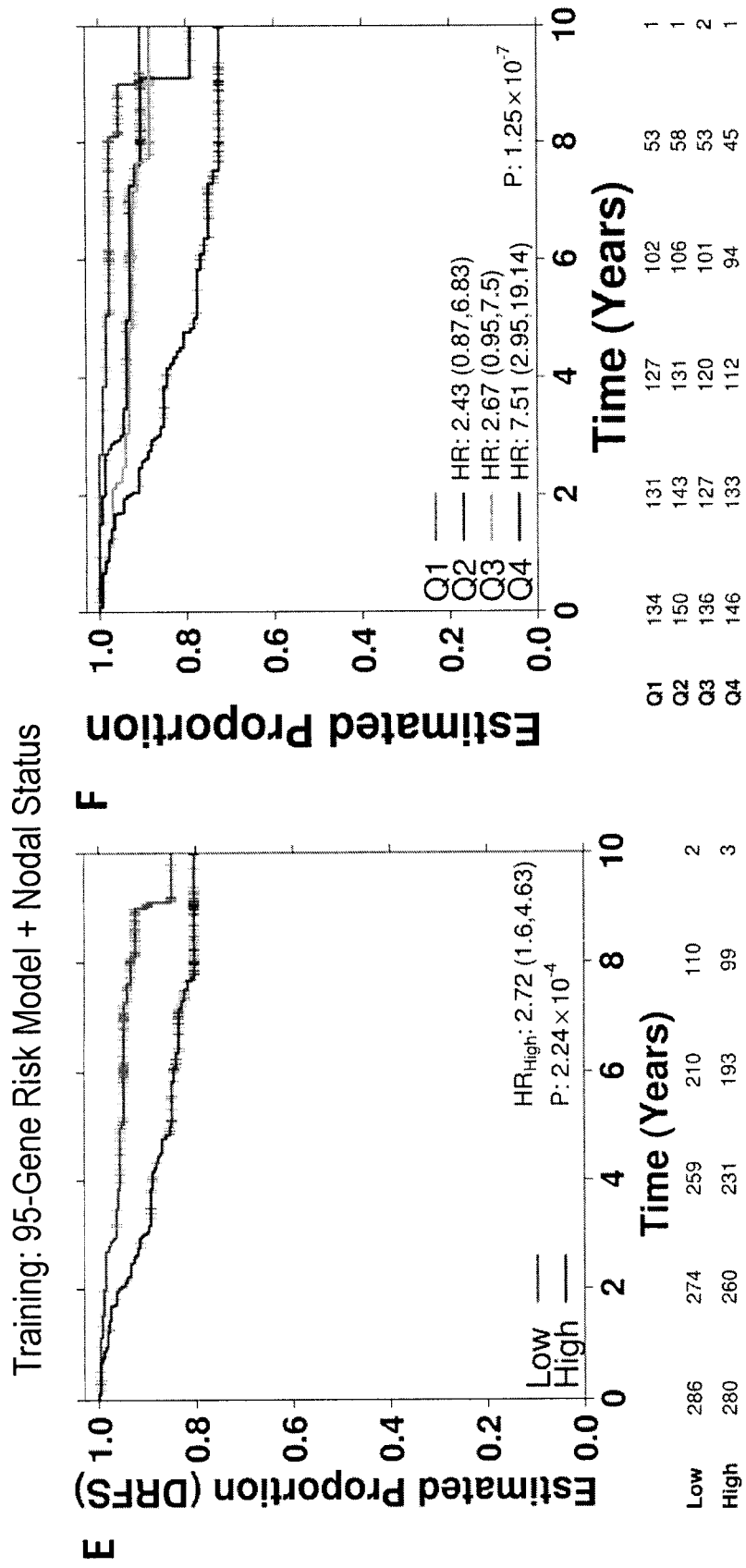
Figures 6A, 6B:
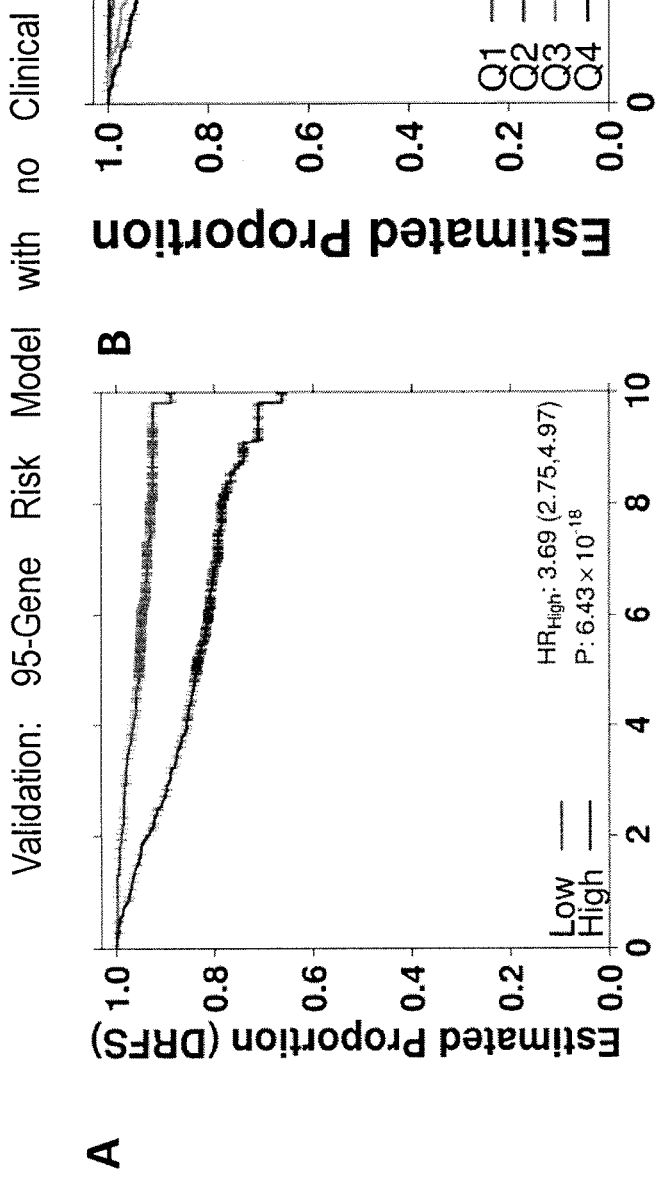
Figure 10:
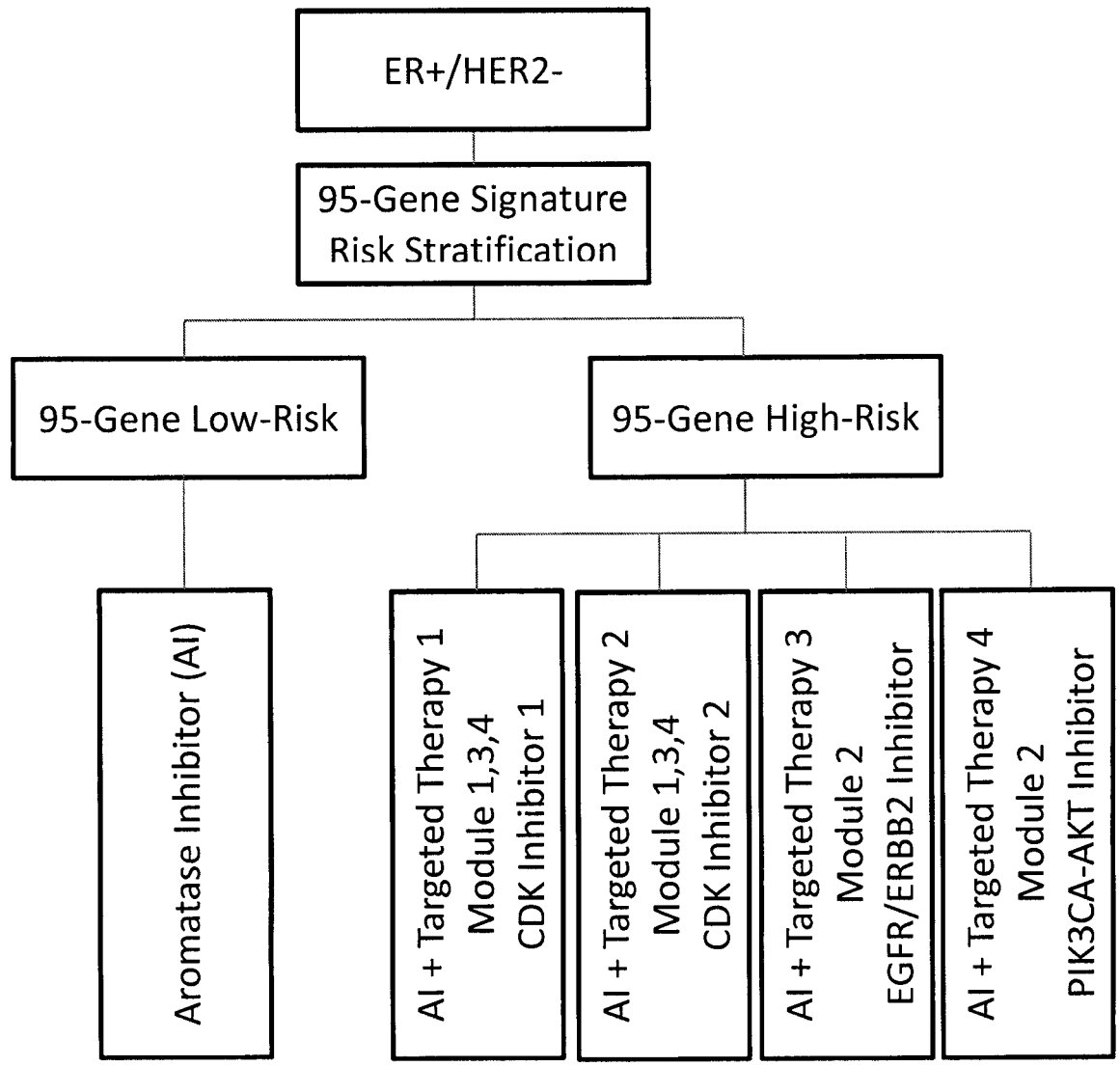
FIG. 10 illustrates putative stratification of patients to novel therapeutics using the 95-gene signature of residual risk. Shown is a putative clinical trial design based on the 95-gene signature to targeted therapies identified by in silico pathway analyses based on expression profiling. In this schema, patients identified as low-risk by the signature receive endocrine treatment only. Those deemed as high-risk, along with the integration of other genomic markers such as gene mutational status and copy-number, are then triaged to targeted treatment directed at the pathways driving their cancer.

Identification and Validation of a Residual Risk Signature Following Endocrine Treatment Univariate assessment of the original gene list of 165 genes identified 95 genes which were prognostically significant in the endocrine only-treated patients (Table 4, see FIG. 4). The 95 genes were aggregated into functional modules and used to train a residual risk model. Modelling of the MDS generated from these 95 genes, with and without clinical covariates, resulted in a final refined signature that included nodal status as the only clinical covariate (see FIG. 1). This risk model was found to be comparable in the training cohort when the 95-gene signature was used, without clinical covariates ($HR_{high}$=4.05, 95% CI 2.25-7.3, p=3.28×10$^{-6}$; 10-fold cross validation) and when clinical co-variates such as age, tumor grade, pathological tumor size and nodal status were included ($HR_{high}$=2.74, 95% CI 1.61-4.65, p=2.06×10$^{-4}$; 10-fold cross validation) (see FIG. 5). When dichotomized around the median and applied to the validation set, the resulting 95-gene signature was a robust predictor of DFRS following endocrine treatment ($HR_{high}$=5.05, 95% CI 3.53-7.22, p=7.51×10$^{-19}$, see FIG. 1A). As with the training set, similar results were obtained when all clinical covariates were included in the model of the validation cohort ($HR_{high}$=5.56, 95% CI 3.85-8.03, p=5.75×10$^{-20}$, see FIG. 6). When samples were split into quartiles (see FIG. 1B), the signature identified patients at very low risk (<5% DRFS at 10 years). Continuous risk scores from this signature were directly correlated with the likelihood of recurrence at 5—(see FIG. 10) and 10-years (see FIG. 1D), with a higher risk score associated with a markedly higher likelihood of a metastatic event.

Performance of the 95-Gene Signature of Residual Risk in the Presence of Adjuvant Chemotherapy To determine whether the 95-gene residual signature continued to be prognostic amongst patients who also received adjuvant chemotherapy, the model was applied to

TABLE 3

Clinical Description of Training and Validation Cohorts (Endocrine-Treated and Endocrine-Treated with Adjuvant Chemotherapy)

Figure 7:
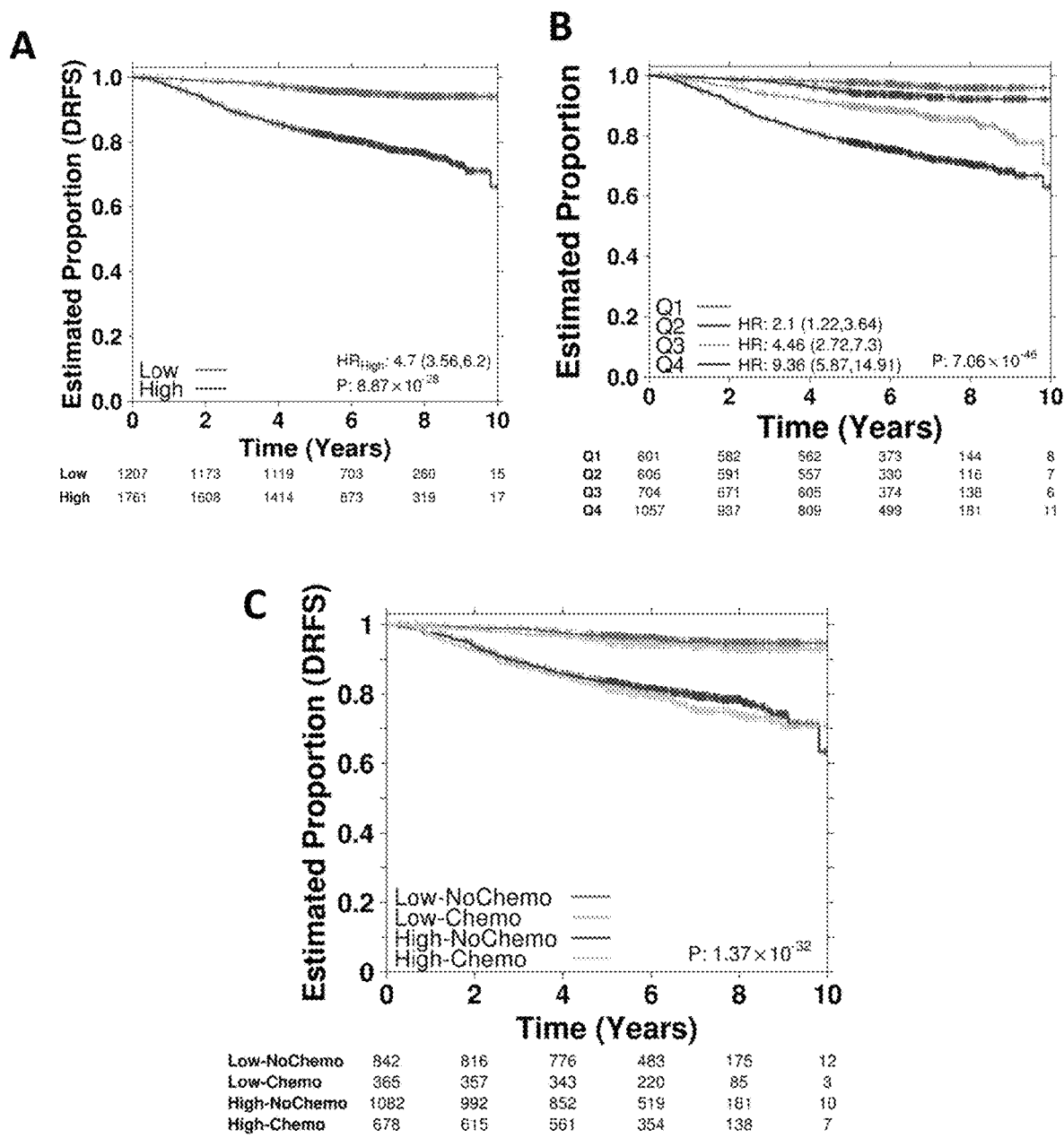
FIG. 7 illustrates validation of the 95-Gene Residual Risk Signature in Chemotherapy-treated and Non-Chemotherapy-treated Patients in the Validation Cohort. A) Kaplan Meier survival curves based on the prognostic modeling of the 95-gene residual risk signature including nodal status in the validation cohort including patients who received adjuvant chemotherapy and adjusted for chemotherapy. B) Risk score estimates shown in A grouped as quartiles with each group compared against Q1. Hazard ratios were estimated using Cox proportional hazards model and significance of survival difference was estimated using the log-rank test. C) Survival curves as shown in A and distinguishing patients identified as high- or low-risk and treatment with adjuvant chemotherapy and adjusted for chemotherapy.

| Samples | Overall | Training Cohort | Validation Cohort | P (Training vs. Validation) |
|---|---|---|---|---|
| Age |  |  |  | 2.48 × 10$^{-2}$ |
| ≥55 | 3322 (86.8%) | 705 (89.2%) | 2617 (86.2%) |  |
| <55 | 503 (13.2%) | 85 (10.8%) | 418 (13.8%) |  |
| Grade |  |  |  | 1.09 × 10$^{-3}$ |
| 1 | 427 (11.7%) | 66 (8.7%) | 361 (12.5%) |  |
| 2 | 1945 (53.4%) | 444 (58.5%) | 1501 (52.0%) |  |
| 3 | 1271 (34.9%) | 249 (32.8%) | 1022 (35.4%) |  |
| Number of positive nodes |  |  |  | 3.92 × 10$^{-8}$ |
| 0 | 1466 (39.3%) | 375 (49.0%) | 1091 (36.8%) |  |
| 1-3 | 1662 (44.5%) | 289 (37.7%) | 1373 (46.3%) |  |
| 4-9 | 416 (11.1%) | 71 (9.3%) | 345 (11.6%) |  |
| 10+ | 190 (5.1%) | 31 (4.0%) | 159 (5.4%) |  |
| Pathological Size (Categorical) |  |  |  | 3.59 × 10$^{-10}$ |
| ≤2 cm | 1806 (47.3%) | 448 (56.8%) | 1358 (44.8%) |  |
| >2 & ≤5 cm | 1787 (46.8%) | 317 (40.2%) | 1470 (48.5%) |  |
| >5 cm | 226 (5.9%) | 24 (3.0%) | 202 (6.7%) |  |
| HER2 |  |  |  | 8.09 × 10$^{-2}$ |
| Negative | 3202 (87.0%) | 659 (85.1%) | 2543 (87.5%) |  |
| Positive | 477 (13.0%) | 115 (14.9%) | 362 (12.5%) |  | all patients in the validation cohort (with and without chemotherapy), but stratified to chemotherapy (see FIGS. 7A and 7B). The results showed that the 95-gene signature was still prognostic in this subset of patients ($HR_{high}$=4.7, 95% Cl 3.56–6.2, p=8.87×10$^{-28}$). Stratifying according to adjuvant chemotherapy showed no difference in the DRFS between patients defined as low or high risk by the signature (see FIG. 7C).

Figure 8:
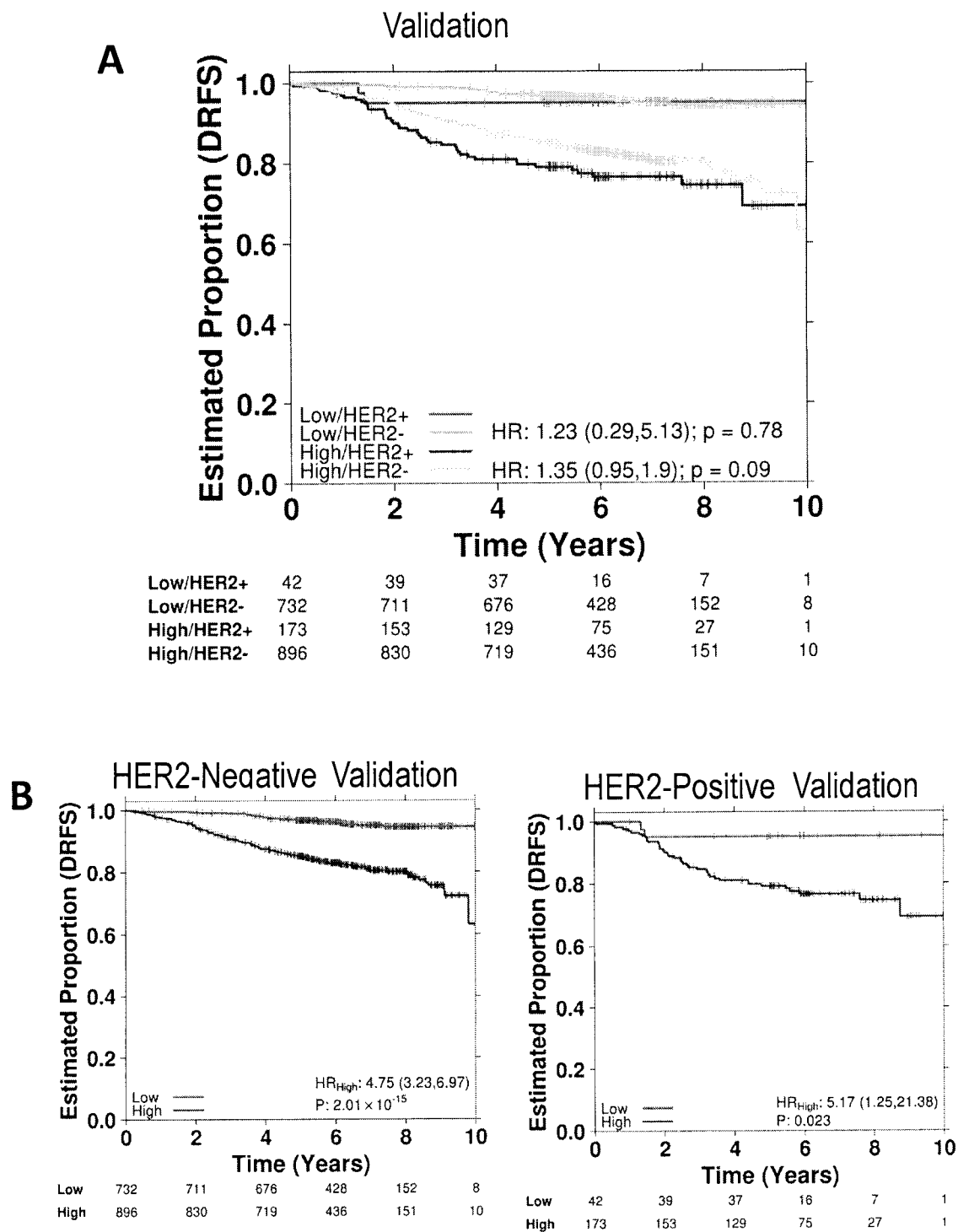
FIG. 8 illustrates validation of the 95-gene residual risk signature in HER2-positive and HER2-negative patients in the validation cohort. A) Kaplan Meier survival curves based on the prognostic modeling of the 95-gene residual risk signature including nodal status in the validation cohort of patients who did not receive adjuvant chemotherapy adjusted for HER2 status. B) Kaplan Meier survival curves based on the prognostic modeling of the 95-gene residual risk signature including nodal status in the validation of cohort patients who did not receive adjuvant chemotherapy adjusted for HER2-negative patients. C) Kaplan Meier survival curves based on the prognostic modeling of the 95-gene residual risk signature including nodal status in the validation cohort of patients who did not receive adjuvant chemotherapy adjusted for HER2-positive patients.
Figures 9A, 9B:
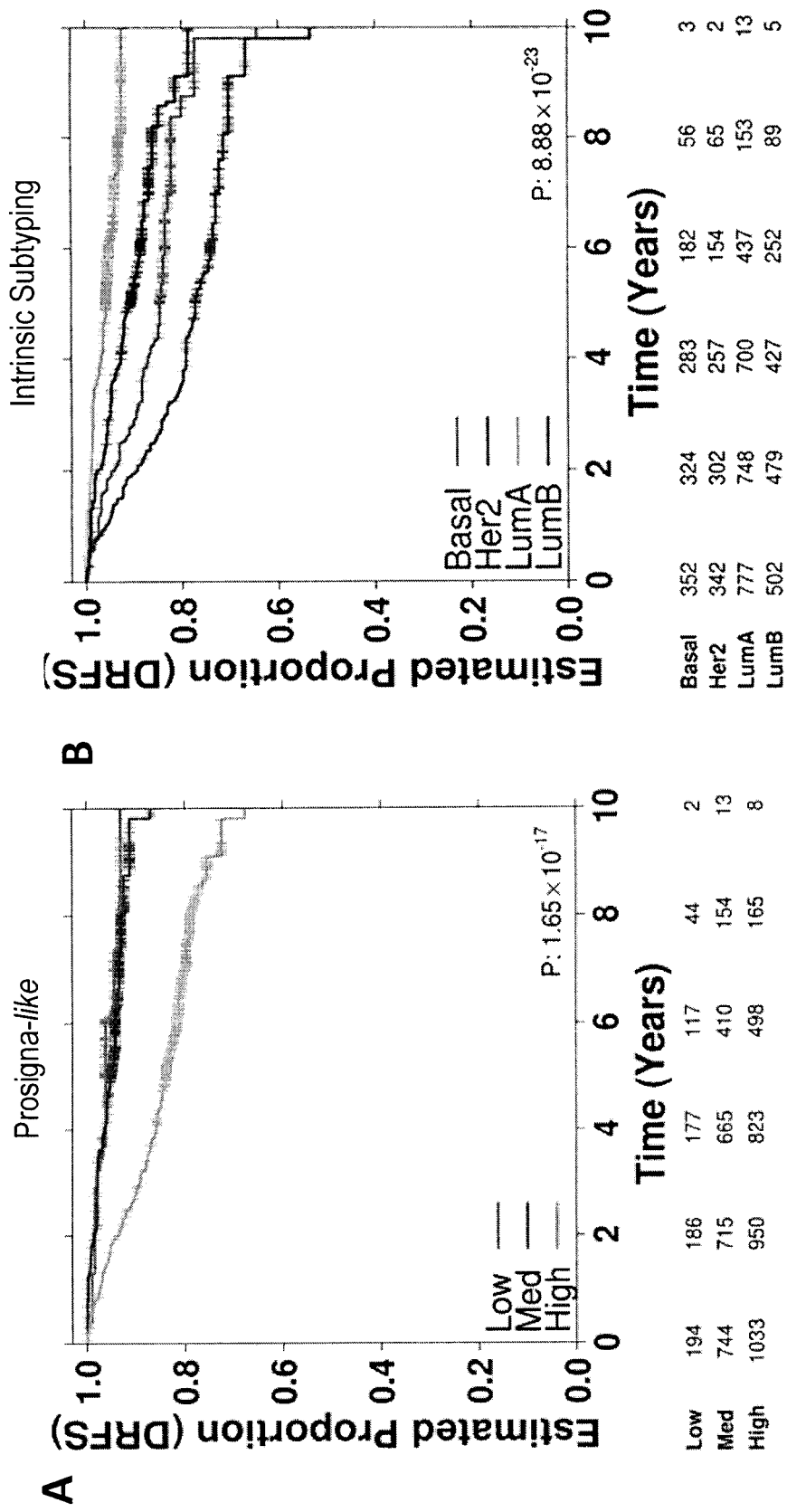
FIG. 9A-9G illustrates Kaplan Meier survival analyses of current commercial and academic multiparametric tests. Shown in the figures are the Kaplan Meier survival curves based on the expression of genes modeled for the various multiparametric tests in the validation cohort. A) Results of the Prosigna test of patients in the validation cohort. Patients identified as low- and intermediate-risk show similar survival, with high-risk patients showing worse DRFS. B) Kaplan Meier survival of patients according to the intrinsic subtyping results based on the Prosigna multiparametric algorithm. C) Kaplan Meier survival analyses of the validation cohort based on OncotypeDx-like expression analyses, dichotomized using a risk score (RS) cut off of 25. D) Kaplan Meier survival analyses of the validation cohort based on MammaPrint-like expression analyses. E) Kaplan Meier survival analyses of the validation cohort based on Genomic Grade Index-like expression analyses. F) Kaplan Meier survival analyses of the validation cohort patients defined as low- and high-risk based on the RNA expression values of the IHC4 genes (ER, PgR, Ki67 and HER2). G) Kaplan Meier survival analyses of the validation cohort patients defined as low- and high-risk based on the protein expression values of the IHC4 genes (ER, PgR, Ki67 and HER2).
Figures 9C, 9D:
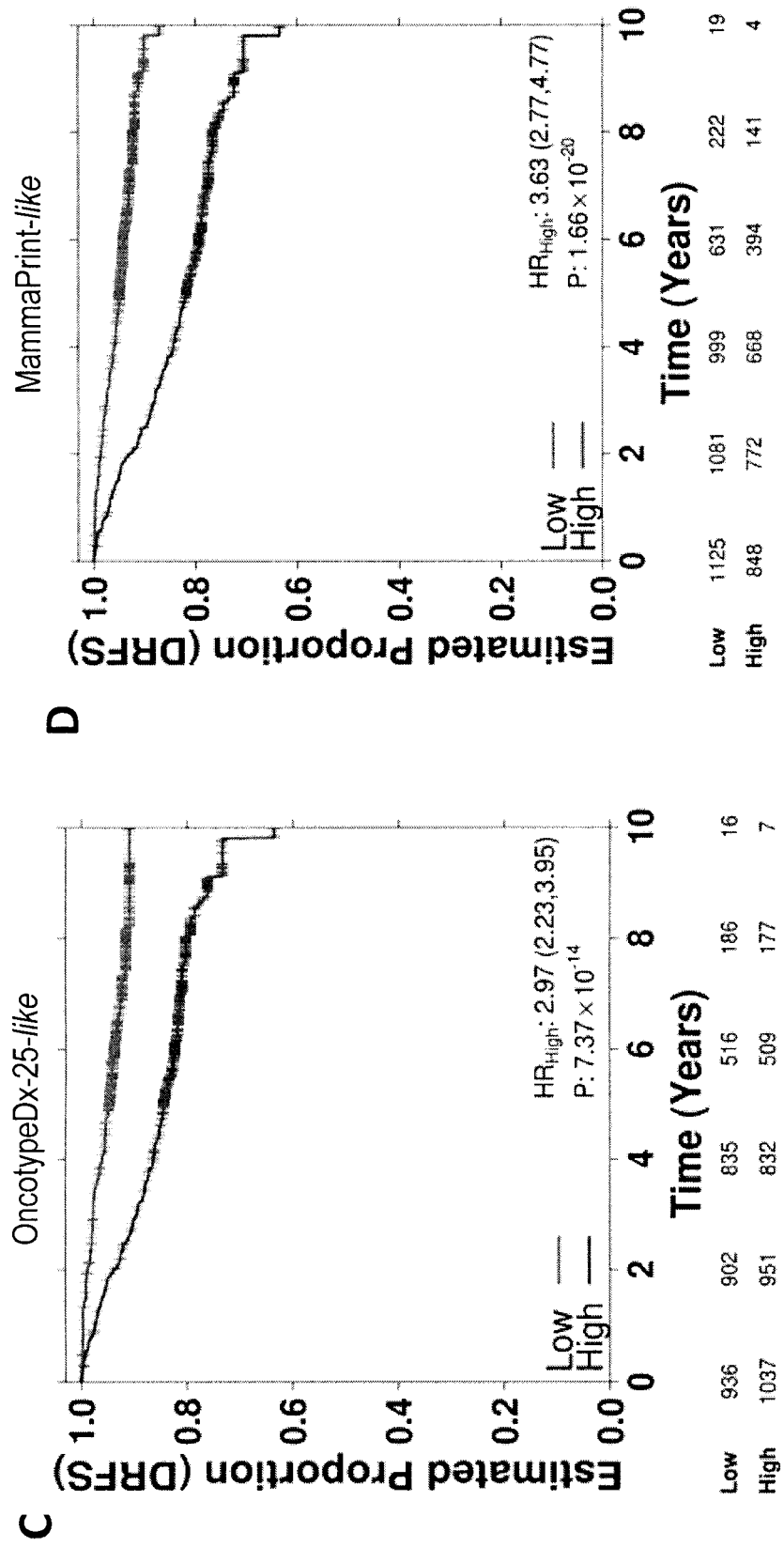
Figure 9F:
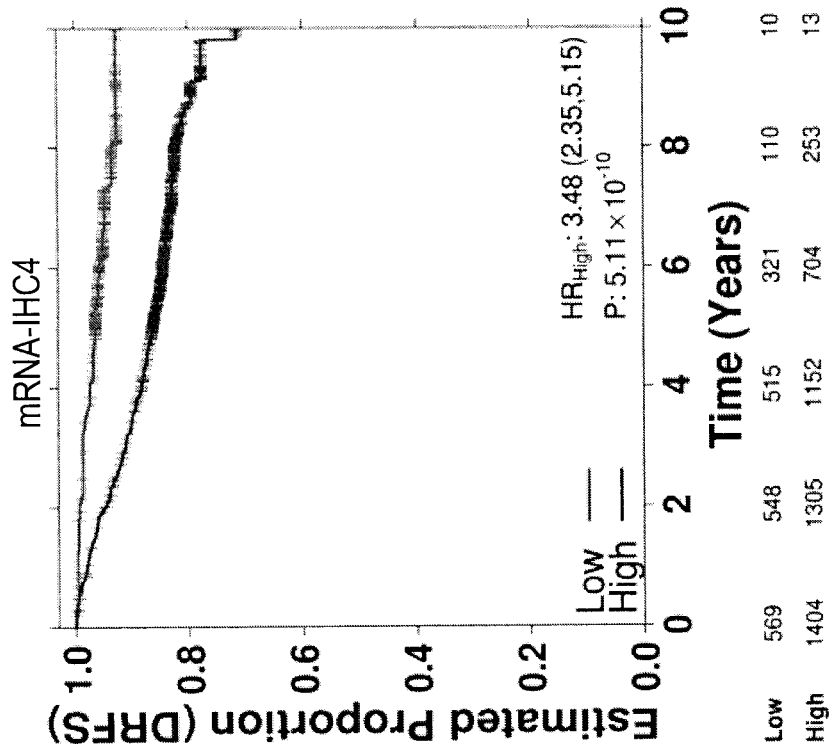
Figure 9E:
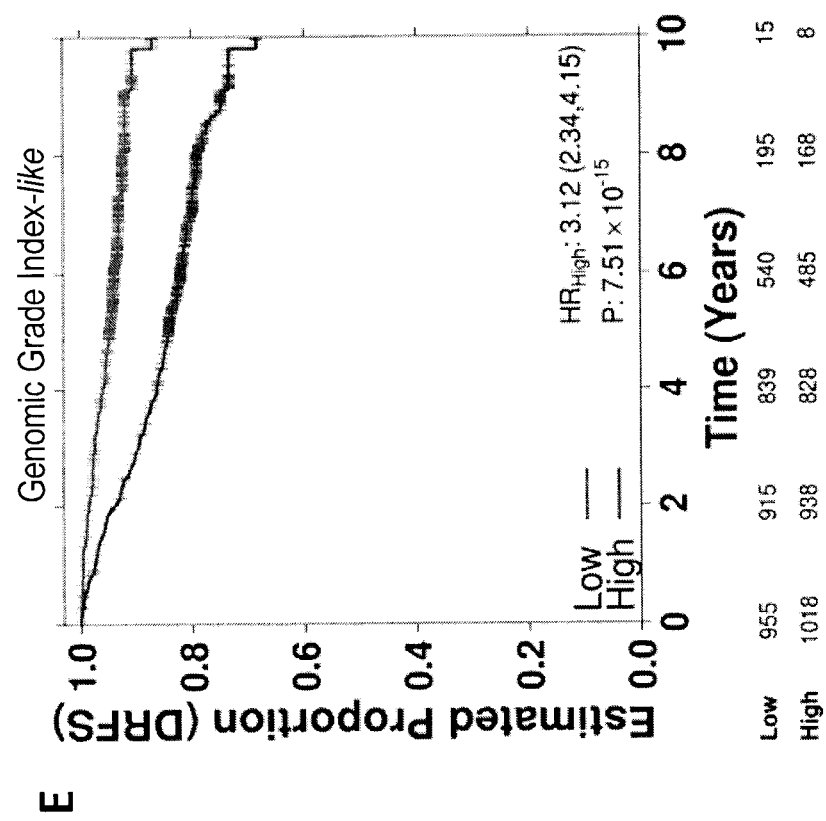
Figure 9G:
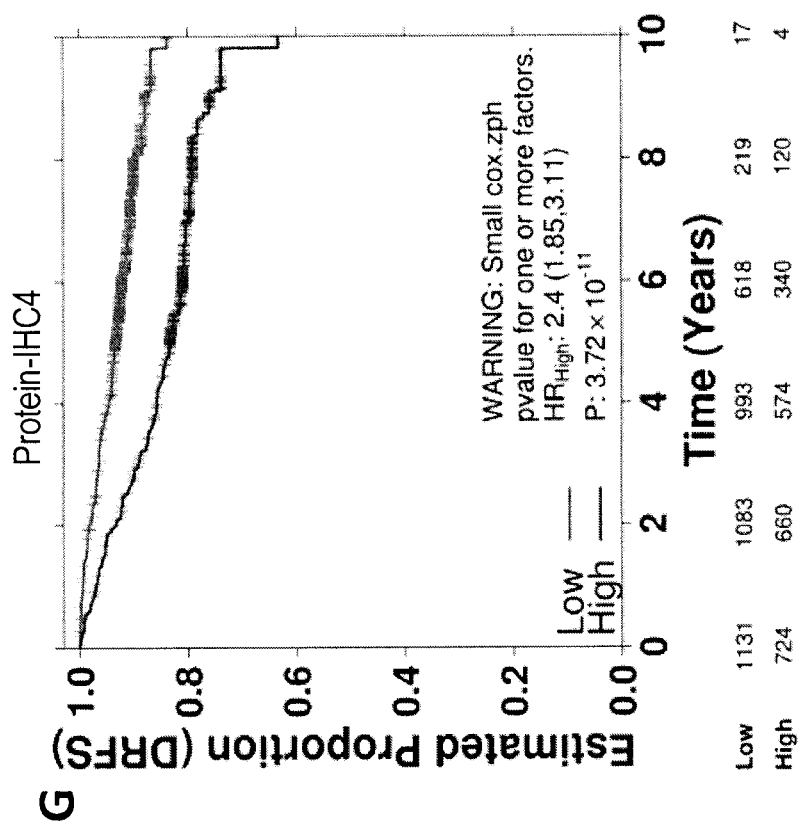

Performance of the 95-Gene Signature of Residual Risk when Adjusted for HER2 Status To determine whether the 95-gene residual risk signature remained prognostic in both HER2-positive and HER2-negative patients, the model was applied to patients in the validation cohort who did not receive any additional adjuvant chemotherapy and results stratified by HER2-status (see FIG. 8). When the model was applied to all patients and stratified by HER2-status (see FIG. 8A), patients identified as low-risk by the 95-gene signature, showed no significant difference in DRFS between HER2-positive or HER-2 negative patients (p=0.78). Similarly, for patients identified as high-risk, no statistically significant difference in DRFS between HER2-positive or HER2-negative patients was observed (p=0.09), although HER2-positive patients were observed to show a trend for worse outcome. Overall, the signature can differentiate high risk from low risk individuals within either HER2-positive (HR=5.17; 95% Cl: 1.25-21.38; p=0.023) or HER2-negative (HR=4.75; 95% Cl: 3.23-6.97; p=2.01×10$^{-15}$) patient subsets (see FIG. 8B).

Performance of the 95-Gene Signature to Multiparametric Tests

Figure 2A:
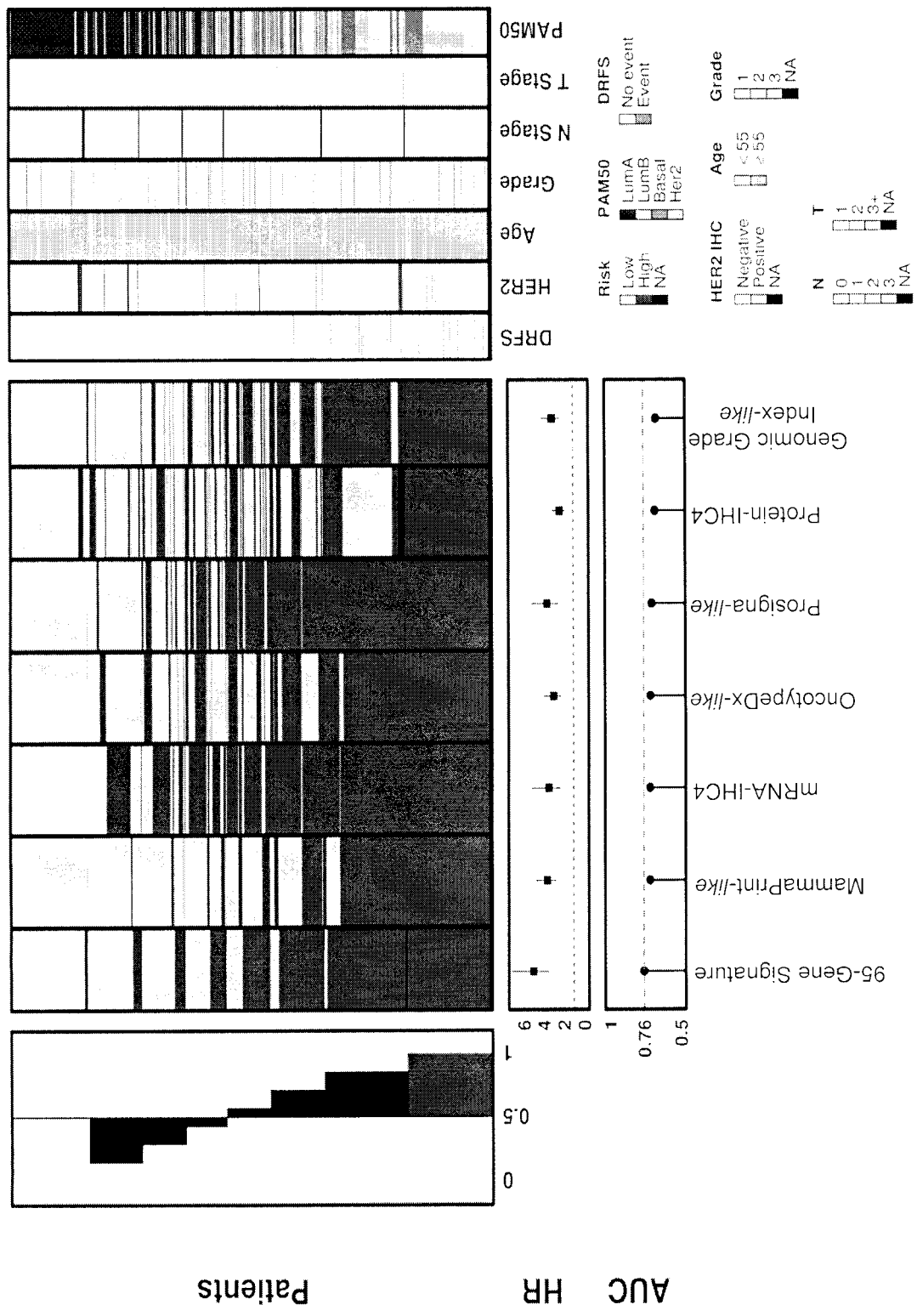
FIGS. 2A and 2B illustrates a comparison of the 95-gene residual risk signature to multi-parametric tests in the validation cohort. A) Summary of patients assessed in the validation cohort using the 95-gene residual risk signature and other current multiparametric tests in addition to clinical covariates. Patients samples were ranked according to overall concordance, with all patients called as high- or low-risk, across all tests organized at the bottom and top of the heatmap, respectively. Standard clinical covariates such as HER2 status, age, grade, nodal status, stage are included. Molecular subtyping based on the PAM50/Prosigna-like test is also shown. B) As performance indicator, area under the receiver operating characteristic (AUC) curves for each multiparametric test is also shown. All patients represented are those who only received endocrine treatment.
Figure 2B:
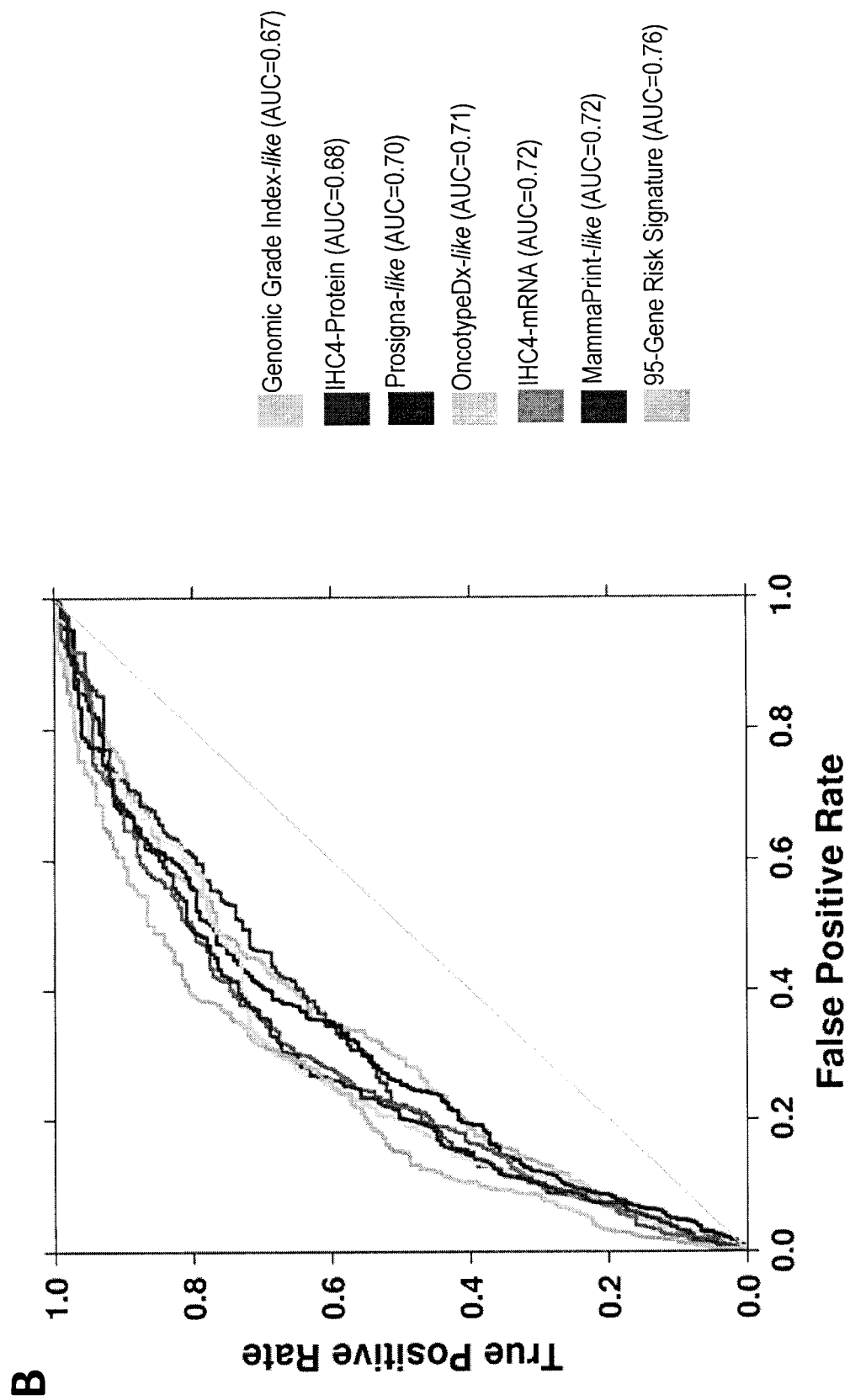

Using the NanoString RNA abundance data, risk scores from current multiparametric test were generated and are summarized in FIG. 2A and Table 5, along with known prognostic clinical factors. Molecular intrinsic subtyping results are also shown (see FIG. 2A). While there exists a common group of high- and low-risk patients across all tests, there are large numbers of patients with discordant results (see FIG. 2A, Table 6). When compared to the risk scores generated based on the commercial tests (see FIG. 2B, Table 7), the 95-gene signature in this study performed better than these multiparametric tests, with an AUC of 0.76. The differences in AUC between the commercial tests and the 95-gene risk score were found to be statistically significant (Table 8). The summary of commercial-like risk scores across the validation cohort, in addition to the overall concordance between the tests are shown in Tables 5 and 6, with Kaplan Meier survival plots for each of the commercial or academic risk stratification tests shown in FIG. 9 and described further in the Supplementary Data. Overall, each test, as recapitulated using the NanoString RNA abundance data, could discriminate with statistical significance (see FIG. 9), between patients at low or high risk for recurrence.

TABLE 5

Summary of Risk Scores Across Different Tests of the Validation Cohort

|  | 95-Gene Signature | MammaPrint-like | OncotypeDx-like (RS cut-off 25) | Prosigna-like | Genomic Grade Index-like | mRNA-IHC4 |
|---|---|---|---|---|---|---|
| Low Risk | n = 822 | n = 1125 | n = 936 | n = 194 | n = 955 | n = 569 |
| Intermediate Risk | NA | NA | NA | n = 744 | NA | NA |
| High Risk | n = 1102 | n = 848 | n = 1037 | n = 1033 | n = 1018 | n = 1404 |
| Luminal A | NA | NA | NA | n = 777 | NA | NA |
| Luminal B | NA | NA | NA | n = 502 | NA | NA |
| Basal-like | NA | NA | NA | n = 352 | NA | NA |
| HER2 enriched-like | NA | NA | NA | n = 342 | NA | NA |

TABLE 6

Multiparametric Test Concordance in the Validation Cohort

|  |  | IHC4 Protein | | Genomic Grade Index-like | | MammaPrint-like | | Prosigna-like | | Oncotype DX-like | |
|---|---|---|---|---|---|---|---|---|---|---|---|
|  |  | Low | High | Low | High | Low | High | Low | High | Low | High |
| Genomic Grade Index-like | Low | 652 | 234 | | | | | | | | |
|  | High | 479 | 490 | | | | | | | | |
| MammaPrint-like | Low | 762 | 291 | 838 | 287 | | | | | | |
|  | High | 369 | 433 | 117 | 731 | | | | | | |
| Prosigna-like | Low | 647 | 221 | 808 | 130 | 844 | 94 | | | | |
|  | High | 483 | 502 | 146 | 887 | 280 | 753 | | | | |
| Oncotype DX-like | Low | 719 | 160 | 661 | 275 | 758 | 178 | 659 | 277 | | |
|  | High | 412 | 564 | 294 | 743 | 367 | 670 | 279 | 756 | | |
| 95-Gene Signature | Low | 585 | 176 | 687 | 135 | 746 | 76 | 705 | 116 | 599 | 223 |
|  | High | 517 | 533 | 241 | 861 | 346 | 756 | 207 | 894 | 312 | 790 |

TABLE 7

Performance of the 95-Gene Residual Risk Signature and
Multiparametric Tests in the Validation Cohort

|  | HR | HR.95L | HR.95U | P | N | AUC |
|---|---|---|---|---|---|---|
| 95-Gene Signature | 5.045 | 3.528 | 7.215 | $7.51 \times 10^{-19}$ | 1924 | 0.76 |
| MammaPrint-like | 3.631 | 2.765 | 4.767 | $1.66 \times 10^{-20}$ | 1973 | 0.72 |
| Prosigna-like | 3.49 | 2.592 | 4.699 | $1.75 \times 10^{-16}$ | 1971 | 0.70 |
| IHC4-RNA | 3.475 | 2.346 | 5.148 | $5.11 \times 10^{-19}$ | 1973 | 0.72 |
| Genomic Grade Index-like | 3.118 | 2.341 | 4.153 | $7.51 \times 10^{-15}$ | 1973 | 0.67 |
| OncotypeDX-iike | 2.969 | 2.232 | 3.948 | $7.37 \times 10^{-14}$ | 1973 | 0.71 |
| IHC4-Protein | 2.398 | 1.851 | 3.108 | $3.72 \times 10^{-11}$ | 1855 | 0.68 |

TABLE 8

Statistical Differences in AUC between Multiparametric Tests and the 95-Gene Residual Risk Signature

|  | Genomic Grade Index-like | IHC4-Protein | Prosigna-like | Oncotype DX-like | IHC4-RNA | MammaPrint-like | 95-Gene Signature |
|---|---|---|---|---|---|---|---|
| Genomic Grade Index-like |  |  |  |  |  |  |  |
| IHC4-Protein | $6.88 \times 10^{-1}$ |  |  |  |  |  |  |
| Prosigna-like | $3.53 \times 10^{-1}$ | $8.81 \times 10^{-1}$ |  |  |  |  |  |
| OncotypeDX-like | $2.04 \times 10^{-2}$ | $8.01 \times 10^{-2}$ | $8.84 \times 10^{-2}$ |  |  |  |  |
| IHC4-RNA | $4.16 \times 10^{-3}$ | $4.28 \times 10^{-2}$ | $2.23 \times 10^{-2}$ | $8.11 \times 10^{-1}$ |  |  |  |
| MammaPrint-like | $2.21 \times 10^{-3}$ | $5.78 \times 10^{-2}$ | $1.21 \times 10^{-2}$ | $7.81 \times 10^{-1}$ | $9.50 \times 10^{-1}$ |  |  |
| 95-Gene Signature | $2.83 \times 10^{-9}$ | $4.02 \times 10^{-5}$ | $3.02 \times 10^{-8}$ | $5.10 \times 10^{-3}$ | $4.25 \times 10^{-3}$ | $2.98 \times 10^{-3}$ |  |

Performance of the 95-gene Residual Risk Signature and Multi-Parametric Tests:

The composition of the gene list enabled the derivation of similar risk classifications representing a number of commercial and academic residual risk stratification tests (see FIG. 2). Kaplan Meier survival plots for each of the commercial and academic tests across the validation cohort showed statistically significant results consistent with the performance for those multi-parametric tests (see FIG. 9, Tables 5 and 6). In direct comparisons, the 95-gene residual-risk classifier produced an area under the curve (AUC) of 0.76, which performed significantly better than other multiparametric test results (Tables 7 and 8). The next best performing classifiers were the MammaPrint-Re results (AUC=0.72), OncotypeDx-like (AUC=0.71), mRNA-IHC4 (AUC=0.72), Prosigna-like (AUC=0.70), protein-IHC4 (AUC=0.68), and the Genomic Grade Index-like results (AUC=0.67). The 95-gene signature performed significantly better than the Genomic Grade Index-like ($2.83 \times 10^{-9}$) and Prosigna-like ($p=3.02 \times 10^{-8}$) results; while also performing better than OncotypeDx-like ($p=5.10 \times 10^{-3}$) and MammaPrint-like ($p=2.98 \times 10^{-3}$) test results generated by the NanoString expression data in this study. Concordance between tests is shown in Table 9 with the 95-gene signature exhibiting greater concordance with MammaPrint-like and Prosigna-like results.

Prosigna-Like Risk of Recurrence Scores and Molecular Subtyping:

Using the genes comprising the Prosigna test, 1971 patients across the endocrine-only treated validation cohort n=194 were identified as being low risk; n=744 were identified as having intermediate risk; and n=1033 identified as being high risk (see Table 5, FIG. 9). The observed DRFS of the validation cohort confirmed previous studies, showing those identified as low- and intermediate-risk experiencing a longer DRFS over high-risk patients ($p=1.65 \times 10^{17}$) (see FIG. 9). Combining low- and intermediate-risk patients resulted in an $HR_{high}$ of 3.49, 95% Cl 2.59-4.7, $p=1.75 \times 10^{-16}$ (see FIG. 9). Molecular subtyping identified 777 (39.3%) patients as Luminal A, 502 patients as Luminal B (25.4%), 352 (17.8%) patients as possessing a Basal-like molecular signature; and 342 (17.5%) patients with a HER2 enriched-like molecular signature (Table 5). Of those patients who were identified as being HER2 enriched-like, and for whom information was available for HER2 status, 113/334 (33.8%) were found to be amplified for HER2 or positive for HER2 overexpression by IHC, while the remaining 221 (66.2%) were negative for gene amplification of protein expression. Differences between the DRFS across molecular subtypes showed a longer DRFS was experienced by Luminal A-classified patients (see FIG. 9), over Luminal B-classified patients; and similarly, Basal-like patients experienced a similar DRFS at 8 years with HER2 enriched-like cases also experiencing shorter DRFS ($p=8.88 \times 10^{-23}$) (see FIG. 9).

OncotypeDx-Like Risk Score:

OncotypeDx-like risk scores were generated according to Paik et al. [43]. In keeping with the cut-off used in the TAILORx study [50, 51], patients were dichotomized into low- or high-risk groups using a risk score of 25 as the cut-off (see FIG. 9), identifying 936 (47.4%) were deemed low-risk and 1037 patients (52.6%) deemed high-risk. A shorter DRFS was shown for patients with risk scores greater than 25 than those with lower risk scores ($HR_{high}=2.97$, 95% Cl 2.23-3.95, $p=7.37 \times 10^{-14}$).

MammaPrint-Like Risk Assessment:

MammaPrint-like risk assessment identified 1125 (57.0%) patients across the endocrine only treated cohort identified as being low risk; and 848 (43%) identified as being high risk. DRFS was longer for low-risk patients and shorter for MammaPrint-like high-risk patients ($HR_{high}=3.63$, 95% Cl 2.77-4.77, $p=1.66 \times 10^{-20}$, see FIG. 9).

Genomic Grade Index-Like Risk Modelling:

When patients were stratified according to the Genomic Grade Index using 995 patients (50.4%) were identified as low risk with the remaining 1018 patients (49.6%) deemed high risk ($HR_{high}=3.12$, 95% Cl 2.34-4.15, $p=7.51 \times 10^{-15}$) see FIG. 9).

IHC4-mRNA Risk Assessment:

Conversion of the protein-based residual risk classifier, IHC4 using the expression values of ER, PgR, Ki67 and HER2 within the code set resulted in 569 (28.8%) patients identified as low-risk and 1404 (71.2%) patients identified as high-risk within the endocrine-only treated patients. DFRS for endocrine-only treated patients deemed low-risk by IHC4-mRNA was longer than those deemed as high-risk ($HR_{high}$=3.48, 95% CI 2.35-5.15, p=5.11×10$^{-10}$, see FIG. 9). Indeed the use of mRNA was comparable in HR to IHC4 using the immunohistochemical results according to the original report, ($HR_{high}$=2.4, 95% CI 1.85-3.11, p=3.72×10$^{-11}$, see FIG. 9).

Figure 3A:
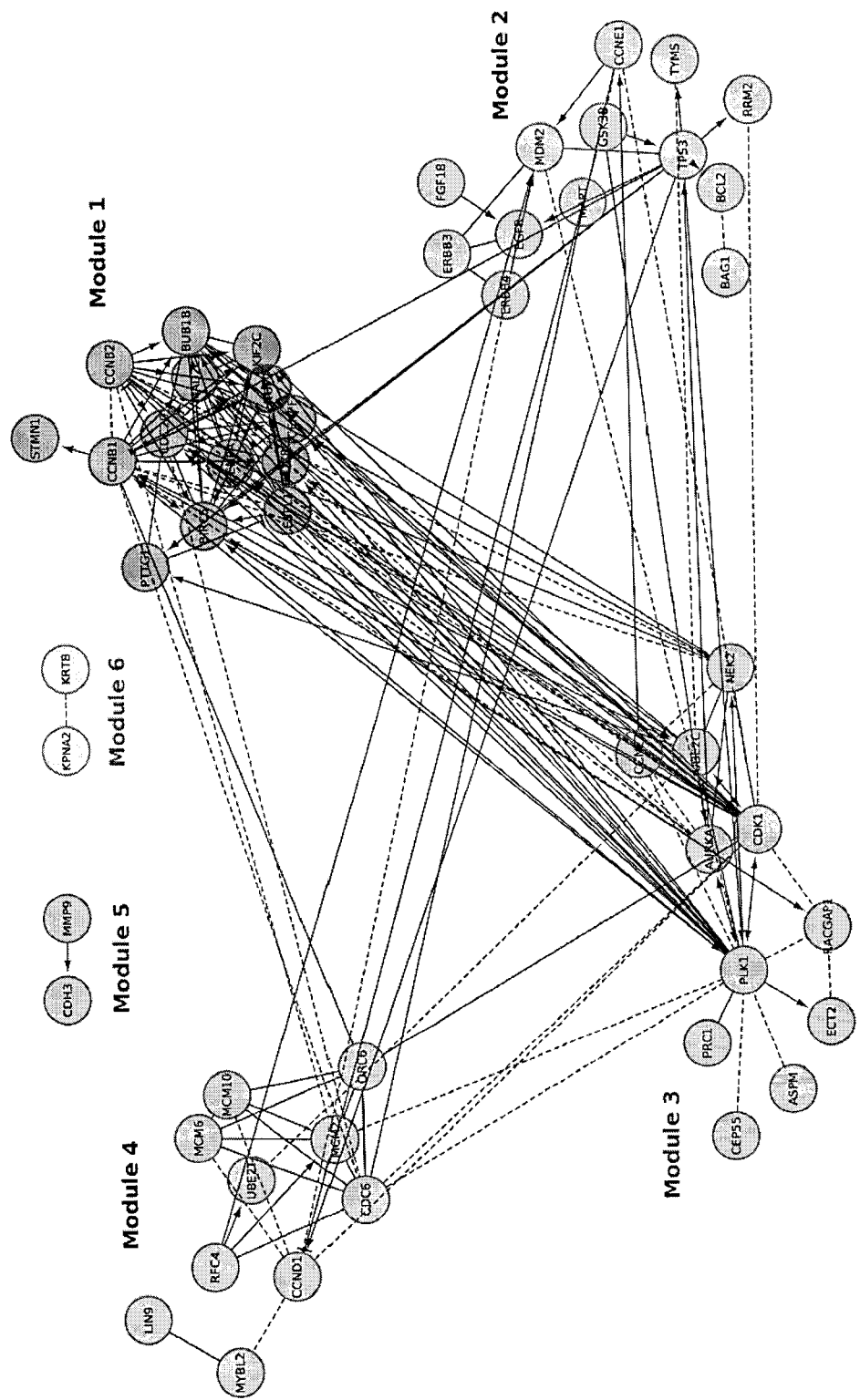
FIG. 3A-3G illustrates signaling modules within the 95-gene residual risk signature.

Identification of Drug Targets in the 95-Gene Signature and Implications for Stratified Precision Medicine Six significant network modules were identified using the Reactome Functional Interaction (FI) tool, comprising 52 of 95 genes in the signature (see FIG. 3A, Table 10). Modules 1, 3 and 4 included genes involved in mitosis (FDR<5.0×10$^{-4}$), cell cycle (FDR<3.33×10$^{-4}$), as well as pathways associated with cell cycle checkpoints (FDR=0.0001). Module 2 included genes and pathways involved in receptor-tyrosine signaling including ERBB pathway signaling (FDR<6.66×10$^{-5}$), PI3K-AKT signaling (FDR<8.33×10$^{-5}$), p53 signaling (FDR<5.00×10$^{-4}$) and apoptosis (FDR=0.00479). Normalized expression for the individual genes (Table 9) within the modules showed that all genes within Modules 1, 3 and 4 were more highly expressed among patients classed as high-risk (Table 9; Wilcoxon rank-sum test).

Figure 3B:
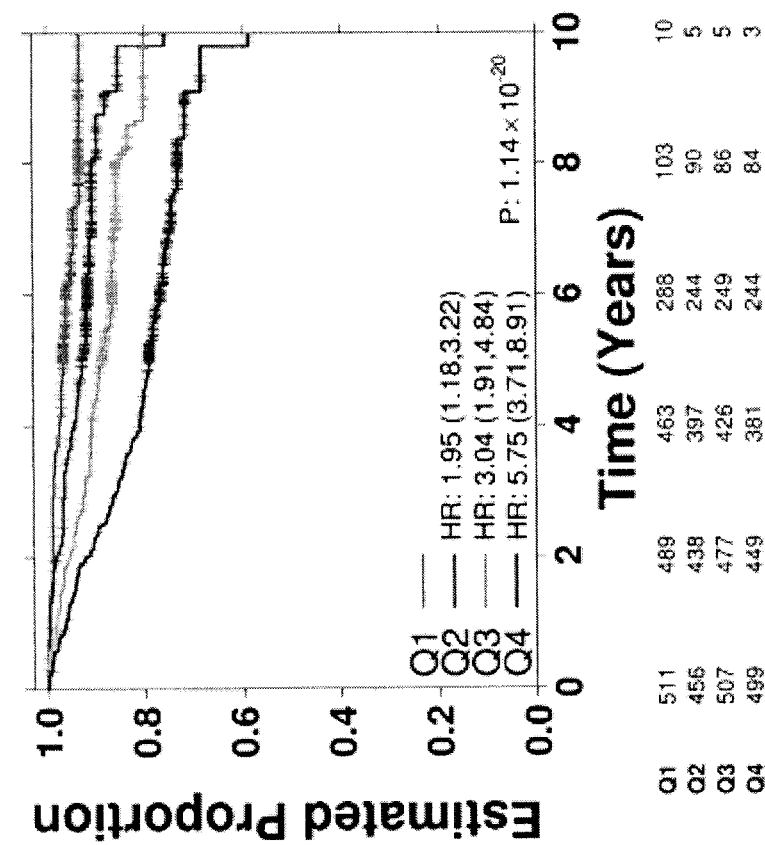
Figure 3B:
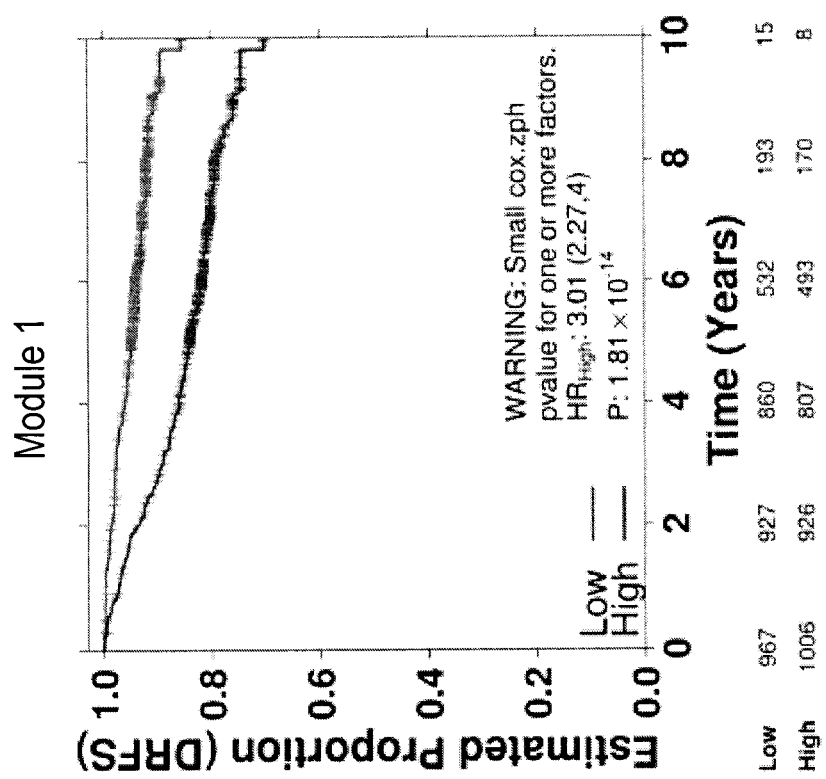
Figure 3C:
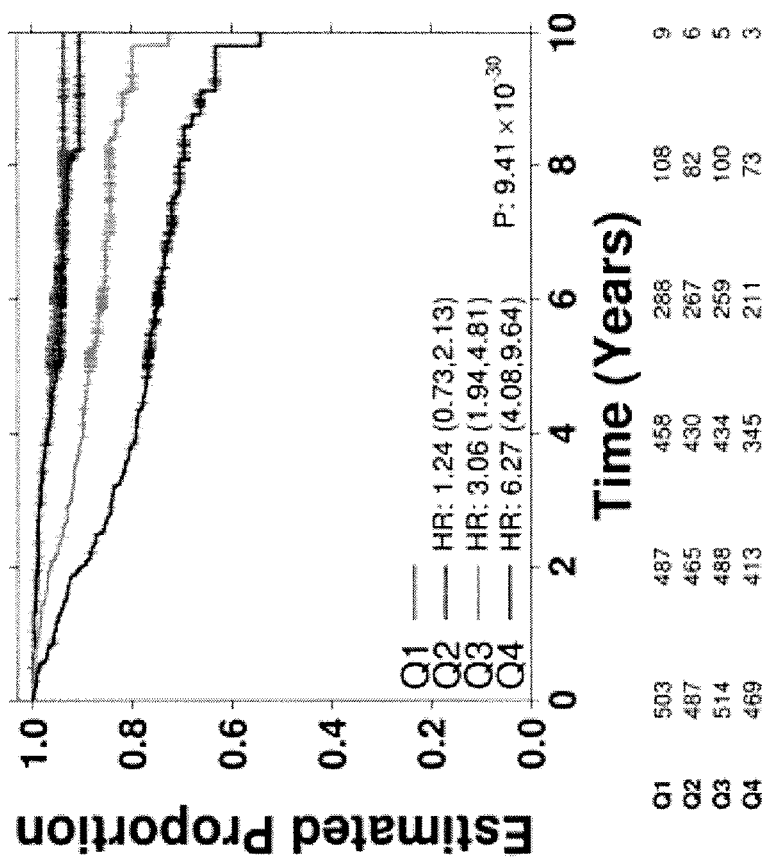
Figure 3C:
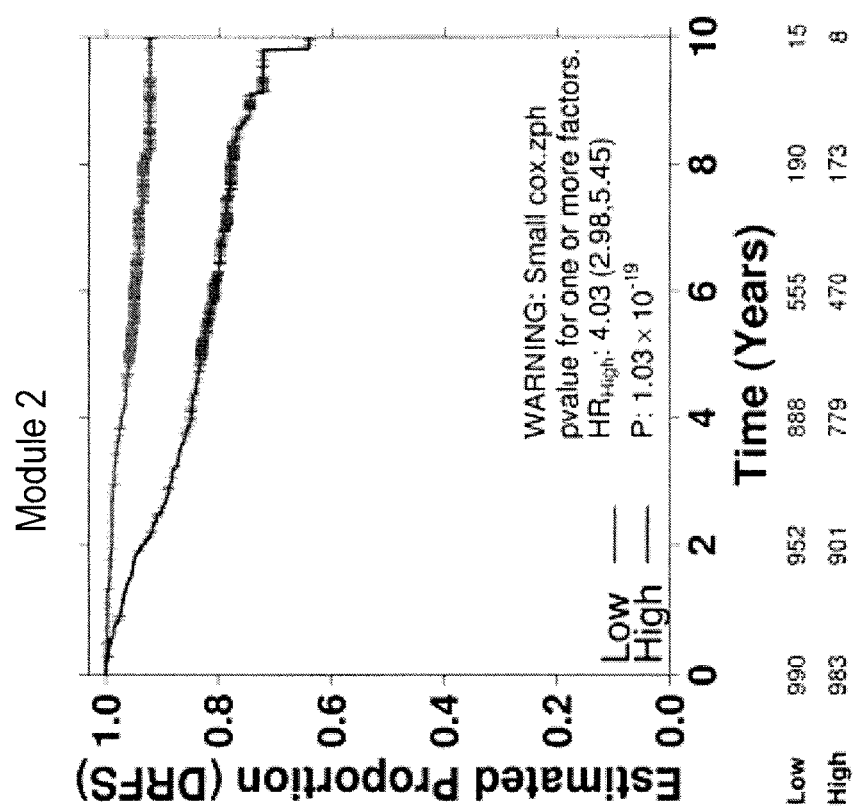
Figure 3D:
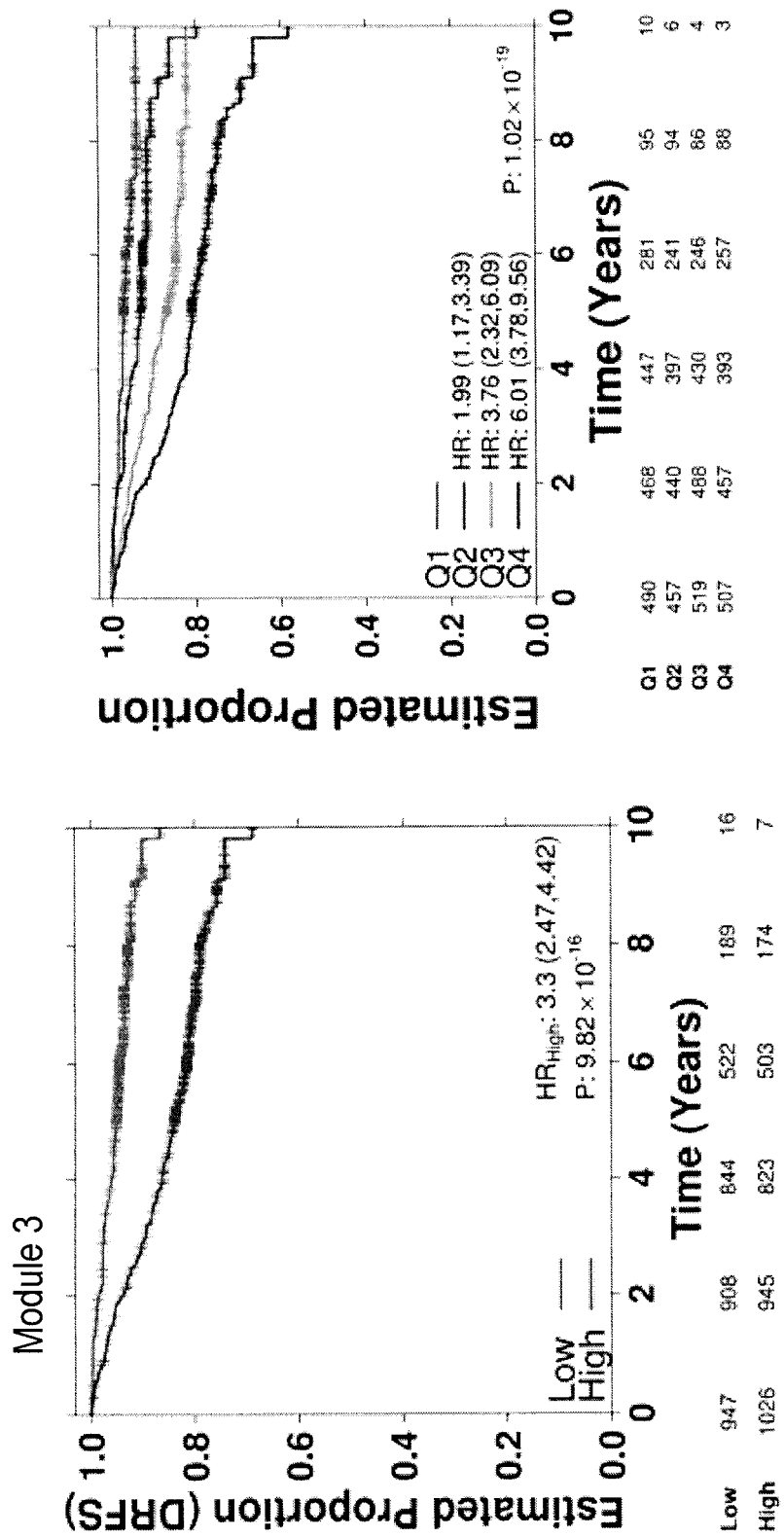
Figure 3E:
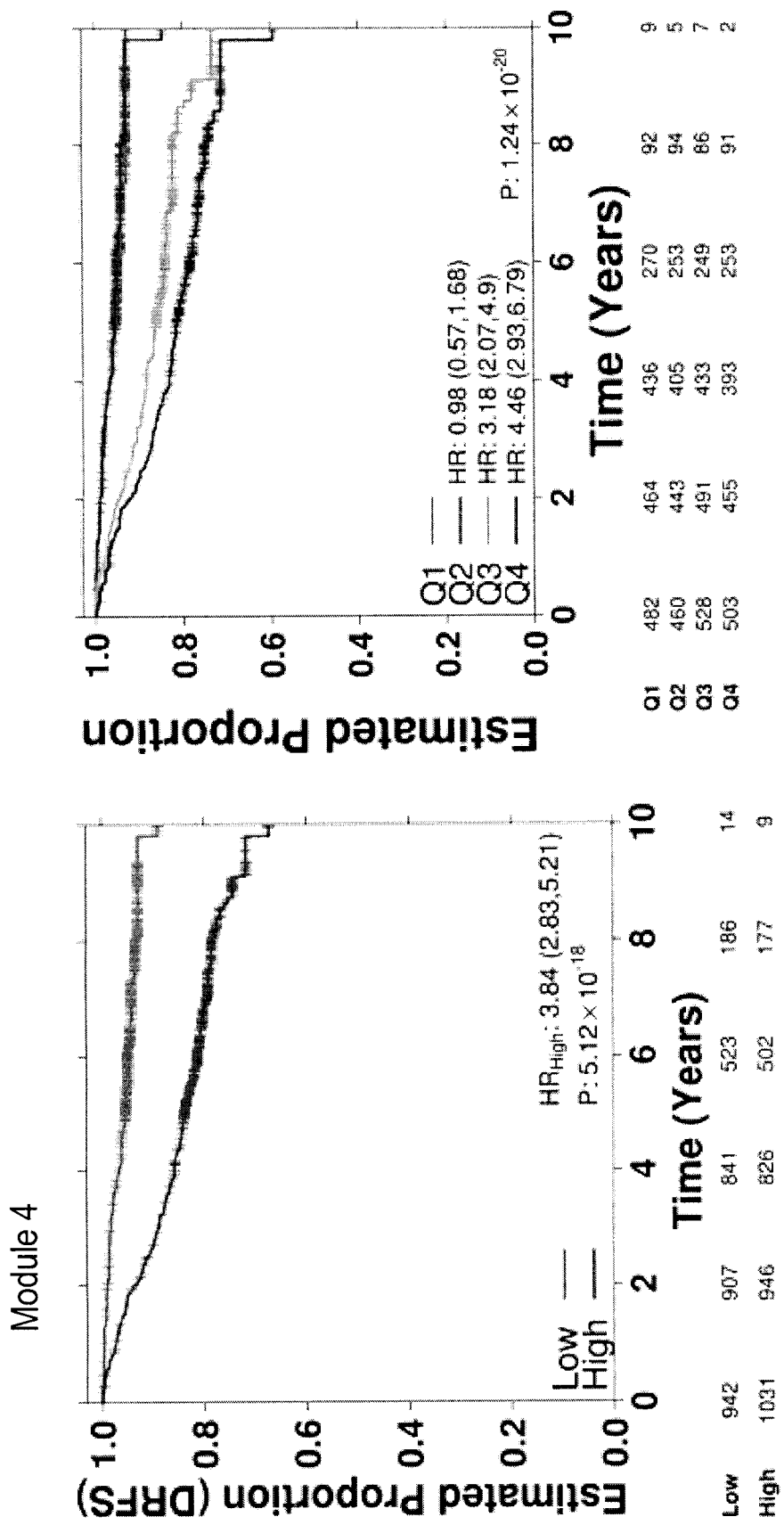
Figure 3F:
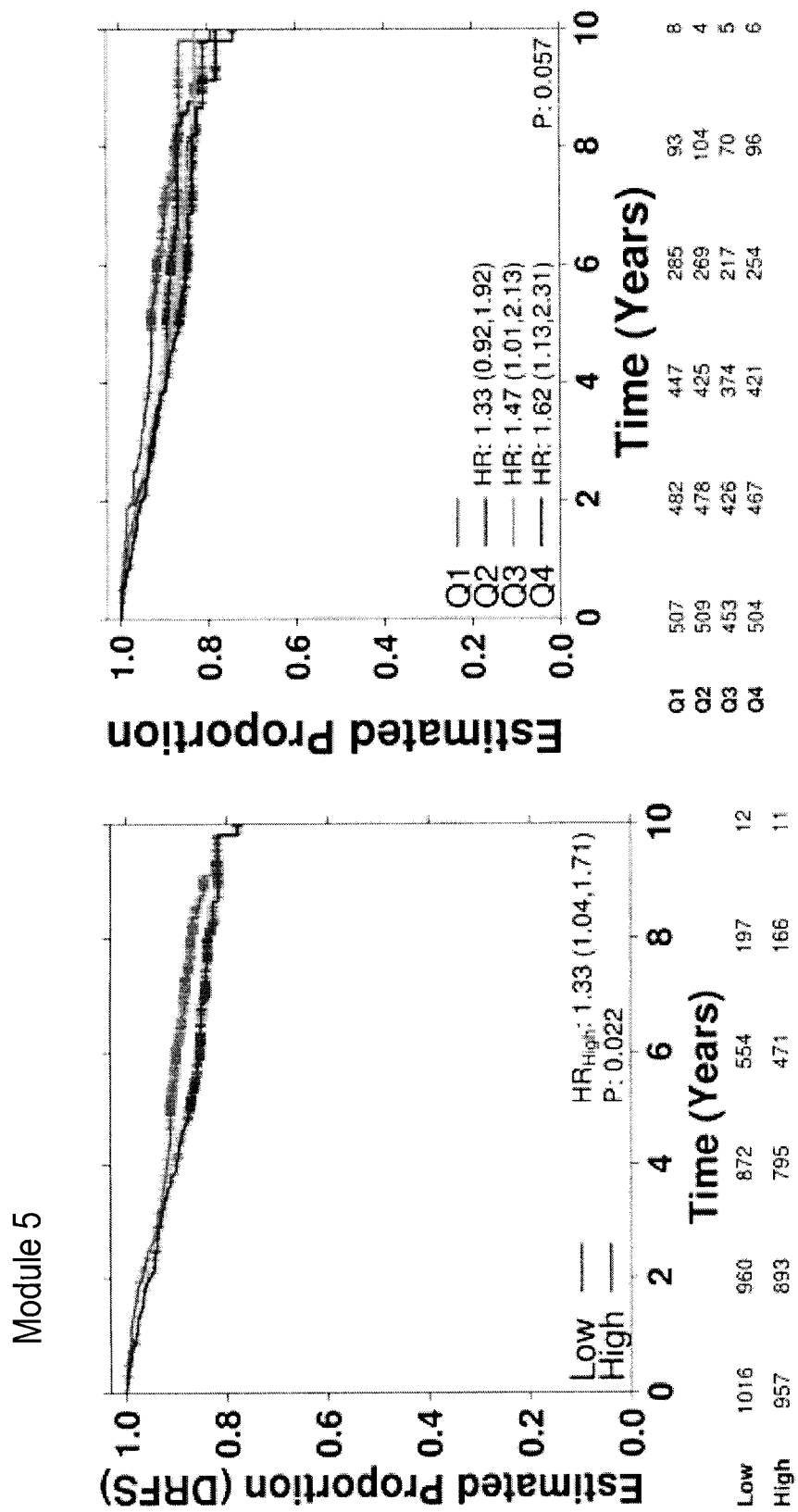
Figure 3G:
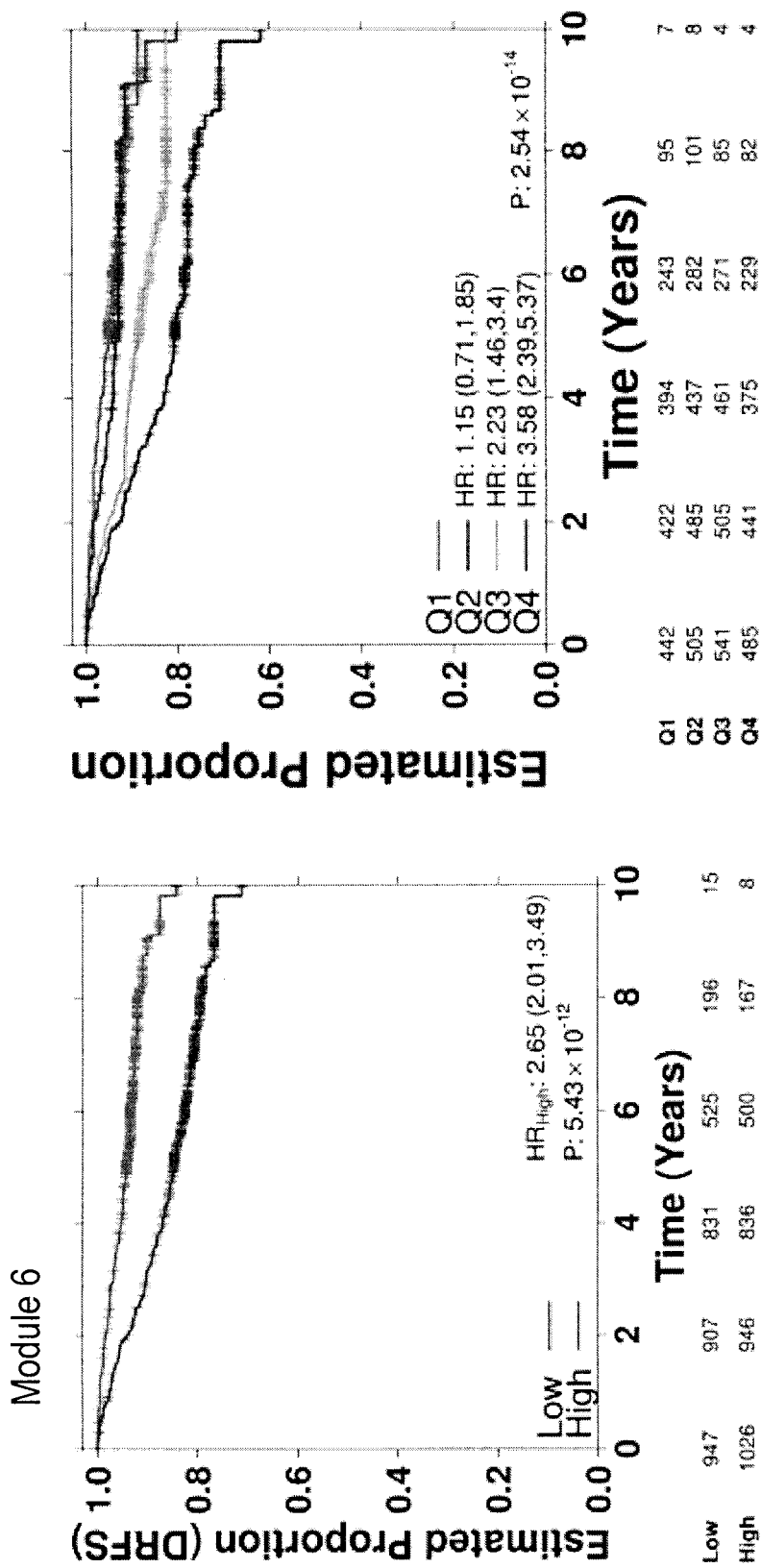

These differences were found to be statistically significant (Table 9). As individual modules, they were statistically significant predictors of outcome (see FIG. 3B). Though not statistically significant, a higher AUC was observed when using all 95 genes together as a residual risk signature set and hence was carried over as the final list ($HR_{high}$=5.05, 95% CI 3.53-7.22, p=7.51×10$^{-19}$). Module 1, comprised of genes largely associated with mitosis and regulation of the cell cycle such as BIRC5, BUB1B, CCNB1 and PTTG1 (Table 10); could classify patients in the validation cohort as low- or high-risk ($HR_{high}$=3.01, 95% CI, p=1.81×10$^{-18}$). Similarly, genes from Modules 3 and 4, including AURKA, CDK1, CCND1, CCNE2, CDC6 and PLK1, classified patients in low- and high-risk categories: $HR_{high}$=3.3, 95% CI 2.47-4.42, p=9.82×10$^{-18}$ and $HR_{high}$=3.84, 95% CI 2.83-5.21, p=5.12×10$^{-18}$, respectively (see FIG. 3B). Normalized RNA abundance within Module 2 was mixed (Table 9), with some showing decreased expression among high-risk patients (i.e. TP53 and BCL2), and others showing increased expression (i.e. CCNE1 and RRM2); but when modelled as a group, Module 2 was could also identify patients with worse prognosis ($HR_{high}$=4.03, 95% CI 2.98-5.45, p=1.03×10$^{-19}$). Finally, Module 5, comprising of CDH3 and MMP9 was also a significant predictor of DRFS ($HR_{high}$=1.33, 95% CI 1.04-1.71, p=0.022), as well as Module 6 comprising two genes; KPNA2 and KRT8 ($HR_{high}$=2.65, 95% CI 2.01-3.49, p=5.43×10$^{12}$).

TABLE 10

Summary of Pathway Modules Comprising the 95-Gene Residual Risk Signature

| Module | Gene List | Pathways in Modules | Putative Targeted Therapy* (Gene Target) |
|---|---|---|---|
| 1 | BIRC5 BUB1B CCNB1 CCNB2 CDC20 CENPA CENPF ESPL1 KIF2C MAD2L1 NDC80 NUF2 PTTG1 STMN1 | Mitotic Metaphase and Anaphase, Mitotic Prometaphase, Cell cycle, Mitotic G2-G2/M phases, Aurora A and B signaling, FOXM1 transcription factor network, Oocyte meiosis, APC/C-mediated degradation of cell cycle proteins, PLK1 signaling events, Cell Cycle Checkpoints, | Gataparsen (BIRC5) |
| 2 | BAG1 BCL2, CCNE1 EGFR, ERBB3 ERBB4 FGF18 GSK3B MAPT MDM2 RRM2 TP53 TYMS | p53 signaling pathway, ERBB-family signalling, PIK3CA-AKT signaling, Aurora A signalling, PLK signalling, cell-cycle checkpoints, apoptotic signalling. AKT-signalling, FGFR signalling, PDGF signalling | Oblimersen Sodium (BCL2), Venetoclax (BCL2), Obatoclax Mesylate (BCL2), Navitoclax (BCL2), Patritumab (ERBB3), Sapitinib (ERBB3), Afatinib (ERBB4), Neratinib (ERBB4), Dacomitinib (ERBB4), Gefitinib (EGFR), Erlotinib (EGFR), Lapatinib (EGFR), Pan-FGFR inhibitor (AP24534, FGF18) |
| 3 | ASPM AURKA CCNE2 CDK1 CEP5 ECT2 NEK2 PLK1 PRC1 RACGAP1 UBE2C | PLK1 signalling, Cell cycle checkpoints, Mitotic telophase and cytokinesis, Mitotic telophase and anaphase, FOXM1 transcription | Diniciclib (CDK1), Rigosertib sodium (PLK1), Volasertib (PLK1) |

TABLE 10-continued

Summary of Pathway Modules Comprising the 95-Gene Residual Risk Signature

| Module | Gene List | Pathways in Modules | Putative Targeted Therapy* (Gene Target) |
|---|---|---|---|
| 4 | CCND1 CDC6 LIN9 MCM10 MCM2 MCM6 MYBL2 ORC6, RFC4 UBE2T | S-phase, Regulation of DNA replication, Cell cycle, p53 signalling, M/G1 transition | Palbociclib (CCND1) |
| 5 | CDH3 MMP9 | Alzheimer disease-presenilin pathway, role of ran in mitotic spindle regulation | |
| 6 | KPNA2 KRT8 | role of ran in mitotic spindle regulation, Regulation of cytoplasmic and nuclear SMAD2/3 signaling | |

Pathways chosen with False Discovery Rate (FDR) p < 0.001
*Compound search conducted using Thomson Reuters Integrity$^{SM}$ and ClinicalTrials.gov (https://clinicaltrials.gov/)

Using the Integrity Compound Search (Thomson Reuters) for the genes within these modules, a number of targeted compounds were identified as being currently used in the clinic for treatment of breast cancer or other neoplasms; or in phase II and/or phase III development (https://clinicaltrials.gov/) (see FIG. 3, Table 11). Among these compounds, a number have potential for stratified use in the early luminal breast cancer setting (Table 10) for those deemed high-risk by the classifier used in this study. Therefore, these compounds hold potential for repurposing targeted therapies to early luminal breast cancers (see FIG. 10).

Relapse following endocrine treatment remains a significant clinical challenge, as more women die following treatment for ER+ disease than for any other breast cancer subtype[3]. Therefore, there is an ongoing need to identify women who are at risk for relapse following endocrine therapy. More importantly, simultaneously identifying targets for future therapeutic intervention and the means to effectively stratify women to such targeted therapies will improve the clinical management of these patients, and potentially reducing their overtreatment, or conversely identifying patients who may be currently undertreated. Using 3825 patients from the TEAM pathology cohort, a signature was derived that both significantly improves risk stratification and identifies genes for which there are drugs currently in use, or under evaluation (https://clinicaltrials.gov/) in other malignancies. These patients could potentially be matched to the specific functional modules within this 95 gene signature (Table 10, Table 11). As alluded to by the prognostic capacity of the individual modules (see FIG. 3), this approach has the potential to better stratify patients to existing targeted therapies based on the molecular drivers of their cancer, and/or to novel/putative targets for in vitro validation studies (see FIG. 10). Despite the fact that the commercial risk score and subtype classification was derived based on NanoString RNA abundance profiling, this study confirmed the recent findings of the UK-OPTIMA prelim trial[17] that most current breast cancer multiparametric risk tests provide broadly equivalent risk information for a population of women with ER+ breast cancers (see FIG. 9), but can exhibit discordance between tests at the individual patient level (see FIG. 2, Tables 5 and 6). Targeted therapies against the molecular drivers of these high-risk patients as revealed by the genes in the signature should be considered and identified, in addition to identifying those patients who may be sensitive to current standard cytotoxic chemotherapies.

While current multiparametric tests can identify those who may benefit from current adjuvant chemotherapy regimens, none of these tests predicts response to a drug-specific chemotherapy. This challenge is hampered by the identification of driver pathways in addition to the complexities of both global and individual chemotherapeutic response. Using the information generated by this data, a model for the examination and validation of candidate drugs which target the gene modules comprising the 95-gene signature (see FIG. 10, Table 11) can be developed.

In this way, genes associated with the G2/M checkpoint, as identified in Module 1, such as BIRC5 (Survivin), could be targeted. YM155, a Survivin suppressor, was evaluated in the metastatic breast cancer setting in combination with docetaxel in a phase II, multicenter, open-label, 2-arm study[20]. However, in that study, the lack of up-front patient stratification for YM155 benefit likely contributed to the finding of no significant benefit in its addition to Docetaxel, thus obscuring the potential benefit of targeting this pathway. While known to be overexpressed in breast cancers, the relatively higher expression of BIRC5 observed among the high-risk patients ($p=7.23\times10^{-180}$) (Table 9) suggests there is a tipping point of mRNA abundance leading to increased risk. All genes within Modules 1, 3 and 4 were observed to show a higher expression among patients at higher risk for relapse which were statistically significant (Table 9), reflecting the prominent role of cell cycle and proliferation in breast cancer pathogenesis.

Module 3 is characterized by pathways involving late mitotic events. The overexpression of CDK1 offers a theranostic target, with the use of Dinacilib or similar molecules, currently under evaluation in phase III trials (Table 11). Regaining cell cycle and mitotic checkpoint control is another attractive mechanism for directed therapies, with theranostic targets such as PLK1 (see FIG. 3), being treated with inhibitors in the preclinical and clinical setting[21,22]. The regulation of S-phase and DNA replication pathways of Module 4, including CCND1, supports the potential stratification of patients to Palbociclib or other CDK inhibitors (Table 11). Findings for the PALOMA-1 trial [23] resulted in approval for Palbociclib (CDK4/6 inhibitor) in combination with Letrozole in the metastatic breast cancer setting; paving the way for the randomization of high-risk patients with ER+/HER2-cancer and residual disease, in the PENELOPE-B trial. While promising in the late and metastatic setting, CDK inhibitor use in the early breast cancer setting has not yet been adequately assessed, nor is there a validated method to stratify patients who would most benefit from this treatment. Interestingly, recent in vitro evidence of synergy between Palbociclib with Tamoxifen showed resensitization to Tamoxifen in ER-resistant cell lines [24], suggesting that the identification of those who may be ER-resistant, could experience greater benefit with the use combined use of endocrine therapy and a CDK inhibitor. Genes of Module 2 are characterized by receptor tyrosine kinase signaling, apoptosis and control of the cell cycle have drug targets among the members of ERBB-family of genes. Anti-HER therapies are effective in ERBB2/HER2-positive patients, but crosstalk between other members of the EGFR/ERBB family suggest the aberrant expression of members aside from ERBB2/HER2 could justify their use in the absence of HER2 amplification. EGFR inhibitors such as Gefitinib and Laptinib have shown efficacy in other malignancies, but only moderate success in breast cancer, suggesting that an improved method of patient selection is required to identify those who would benefit the most. Interestingly, 296/342 (86.5%) HER2-enriched-like patients were identified as high-risk by the classifier used in this study.

However, with 33.8% of HER2-enriched-like patients possessing confirmed HER2 gene amplification or protein over-expression, these results suggest some patients may benefit from therapy targeting the ERBB-family and associated pathways. In fact, the 95-gene signature was still prognostic irrespective of ERBB2/HER2-status, in this population of patients that pre-dates the use of anti-ERBB2/HER2 therapies (see FIG. 8). Moreover, while ERBB3 and ERBB4 were found to be univariately prognostic and part of the final signature, ERBB2/HER2 expression was not (Table 4). This data would suggest that in current clinical practice, a number of the ERBB2/HER2-positive, low-risk patients would have received anti-ERBB2/HER2 therapies, resulting with an outcome potentially no better than ERBB2/HER2-negative patients. With respect to high-risk patients who were also ERBB2/HER2-positive, anti-ERBB2/HER2 treatment would have some benefit to a subset in this group, but it is clear that there are other molecular drivers of recurrence in this high-risk population. Downstream pathways of ERBB, like PIK3/AKT/mTOR, which was identified as a significant pathway by the present analyses, supports the potential use of Everolimus in patients identified as high-risk [25, 26]. Interestingly, 278/352 (78.9%) of patients identified as Basal-like were classified as high-risk by the gene signature despite being clinically classified as ER+; highlighting the need to recognize the importance of molecular heterogeneity among the hormone receptor positive cancers, and the implications for novel treatment.

It was demonstrated that a 95-gene signature of residual risk, which integrates nodal status, has significantly better clinical utility for early recurrence than the currently available multiparametric tests. This signature appears to remain prognostic for later recurrence. Unlike these multiparametric tests, modular analysis of the genes in the signature, have identified several genes and pathways suitable for therapeutic intervention among the high-risk patients. There is a need for significant improvement in the targeted selection of patients suitable for new therapies, rather than the randomization of all-comers in future clinical trial design.

Hormone-receptor positive cancers are molecularly heterogeneous, thus requiring novel treatment strategies (see FIG. 2A and Table 5, Table 11). A multiparametric gene signature is one means of selection, but improved stratification must also include the integration of gene mutational and copy-number status. Therefore in order to improve the clinical management of women with early hormone-receptor positive breast cancer, future clinical trial design requires a multiparametric test that not only improves identification of high-risk patients, but also improves the selection of patients to existing therapeutics which target key genes/pathways that underlies the signature.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 4

Univariate Results of Prognostically Significant Genes in the 95-Gene Signature of the Validation Cohort

| | Validation: Endocrine-treated | | | | | Validation: Endocrine-treated + Adjuvant Chemotherapy | | | | |
| --- | --- | --- | --- | --- | --- | --- | --- | --- | --- | --- |
| | Coef | HR | HR.95L | HR.95U | P | | Coef | HR | HR.95L | HR.95U | P |
| ACTR3B | −0.1555 | 0.856 | 0.669 | 1.096 | $2.19 \times 10^{-1}$ | ACTR3B | −0.2033 | 0.816 | 0.675 | 0.986 | $3.50 \times 10^{-2}$ |
| ANLN | 1.1135 | 3.045 | 2.302 | 4.027 | $5.99 \times 10^{-15}$ | ANLN | 0.9639 | 2.622 | 2.131 | 3.228 | $9.11 \times 10^{-20}$ |
| ASPM | 0.7400 | 2.096 | 1.615 | 2.721 | $2.71 \times 10^{-8}$ | ASPM | 0.7743 | 2.169 | 1.774 | 2.653 | $4.66 \times 10^{-14}$ |
| AURKA | 0.9042 | 2.47 | 1.886 | 3.236 | $5.10 \times 10^{-11}$ | AURKA | 0.6931 | 2 | 1.638 | 2.44 | $9.19 \times 10^{-12}$ |
| BAG1 | −0.1416 | 0.868 | 0.678 | 1.111 | $2.60 \times 10^{-1}$ | BAG1 | −0.1031 | 0.902 | 0.746 | 1.089 | $2.83 \times 10^{-1}$ |
| BCL2 | −0.7423 | 0.476 | 0.367 | 0.618 | $2.54 \times 10^{-8}$ | BCL2 | −0.7508 | 0.472 | 0.386 | 0.576 | $1.90 \times 10^{-13}$ |
| BIRC5 | 1.0784 | 2.94 | 2.227 | 3.883 | $2.91 \times 10^{-14}$ | BIRC5 | 0.9666 | 2.629 | 2.135 | 3.238 | $8.70 \times 10^{-20}$ |
| BUB1B | 1.1869 | 3.277 | 2.464 | 4.358 | $3.30 \times 10^{-16}$ | BUB1B | 0.9888 | 2.688 | 2.181 | 3.313 | $1.89 \times 10^{-20}$ |
| CCNB1 | 0.9670 | 2.63 | 2.004 | 3.452 | $3.20 \times 10^{-12}$ | CCNB1 | 0.9103 | 2.485 | 2.023 | 3.052 | $4.31 \times 10^{-18}$ |
| CCNB2 | 0.8658 | 2.377 | 1.818 | 3.106 | $2.38 \times 10^{-10}$ | CCNB2 | 0.8817 | 2.415 | 1.967 | 2.965 | $3.87 \times 10^{-17}$ |
| CCND1 | 0.0602 | 1.062 | 0.83 | 1.36 | $6.31 \times 10^{-1}$ | CCND1 | 0.0862 | 1.09 | 0.902 | 1.316 | $3.74 \times 10^{-1}$ |
| CCNE1 | 0.7041 | 2.022 | 1.559 | 2.623 | $1.13 \times 10^{-7}$ | CCNE1 | 0.7376 | 2.091 | 1.711 | 2.555 | $5.69 \times 10^{-13}$ |
| CCNE2 | 0.6941 | 2.002 | 1.544 | 2.595 | $1.58 \times 10^{-7}$ | CCNE2 | 0.6851 | 1.984 | 1.627 | 2.42 | $1.34 \times 10^{-11}$ |
| CDC20 | 0.9099 | 2.484 | 1.897 | 3.254 | $3.89 \times 10^{-11}$ | CDC20 | 0.8616 | 2.367 | 1.929 | 2.904 | $1.45 \times 10^{-16}$ |
| CDC6 | 0.8684 | 2.383 | 1.825 | 3.112 | $1.81 \times 10^{-10}$ | CDC6 | 0.7056 | 2.025 | 1.66 | 2.472 | $3.80 \times 10^{-12}$ |
| CDCA7 | 0.5481 | 1.73 | 1.342 | 2.23 | $2.35 \times 10^{-5}$ | CDCA7 | 0.4440 | 1.559 | 1.286 | 1.89 | $6.39 \times 10^{-6}$ |
| CDH3 | 0.1748 | 1.191 | 0.93 | 1.525 | $1.67 \times 10^{-1}$ | CDH3 | 0.0535 | 1.055 | 0.873 | 1.274 | $5.79 \times 10^{-1}$ |
| CDK1 | 0.9768 | 2.656 | 2.023 | 3.487 | $1.97 \times 10^{-12}$ | CDK1 | 0.8842 | 2.421 | 1.974 | 2.971 | $2.31 \times 10^{-17}$ |

TABLE 4-continued

Univariate Results of Prognostically Significant Genes in the 95-Gene Signature of the Validation Cohort

| | Validation: Endocrine-treated | | | | | Validation: Endocrine-treated + Adjuvant Chemotherapy | | | | | |
|---|---|---|---|---|---|---|---|---|---|---|---|
| | Coef | HR | HR.95L | HR.95U | P | | Coef | HR | HR.95L | HR.95U | P |
| CENPA | 0.9817 | 2.669 | 2.033 | 3.503 | $1.54 \times 10^{-12}$ | CENPA | 0.8312 | 2.296 | 1.874 | 2.812 | $9.56 \times 10^{-16}$ |
| CENPF | 1.0178 | 2.767 | 2.105 | 3.636 | $2.89 \times 10^{-13}$ | CENPF | 0.9075 | 2.478 | 2.018 | 3.043 | $4.54 \times 10^{-18}$ |
| CEP55 | 1.1762 | 3.242 | 2.442 | 4.306 | $4.35 \times 10^{-16}$ | CEP55 | 1.0396 | 2.828 | 2.291 | 3.491 | $4.08 \times 10^{-22}$ |
| CMC2 | 0.4916 | 1.635 | 1.268 | 2.108 | $1.48 \times 10^{-4}$ | CMC2 | 0.5642 | 1.758 | 1.445 | 2.138 | $1.68 \times 10^{-8}$ |
| CX3CR1 | −0.7236 | 0.485 | 0.374 | 0.629 | $4.70 \times 10^{-8}$ | CX3CR1 | −0.5745 | 0.563 | 0.463 | 0.684 | $7.73 \times 10^{-9}$ |
| CXXC5 | 0.5562 | 1.744 | 1.353 | 2.249 | $1.80 \times 10^{-5}$ | CXXC5 | 0.3723 | 1.451 | 1.198 | 1.758 | $1.40 \times 10^{-4}$ |
| DHX58 | −0.2244 | 0.799 | 0.624 | 1.024 | $7.66 \times 10^{-2}$ | DHX58 | −0.2319 | 0.793 | 0.656 | 0.959 | $1.67 \times 10^{-2}$ |
| DIAPH3 | 0.5271 | 1.694 | 1.314 | 2.183 | $4.79 \times 10^{-5}$ | DIAPH3 | 0.4612 | 1.586 | 1.307 | 1.924 | $2.88 \times 10^{-6}$ |
| DTL | 0.6286 | 1.875 | 1.45 | 2.426 | $1.70 \times 10^{-6}$ | DTL | 0.6334 | 1.884 | 1.547 | 2.295 | $3.15 \times 10^{-10}$ |
| EBF4 | 0.1756 | 1.192 | 0.931 | 1.526 | $1.64 \times 10^{-1}$ | EBF4 | 0.0602 | 1.062 | 0.879 | 1.283 | $5.32 \times 10^{-1}$ |
| ECT2 | 1.1072 | 3.026 | 2.289 | 4.002 | $7.87 \times 10^{-15}$ | ECT2 | 1.0392 | 2.827 | 2.288 | 3.491 | $5.32 \times 10^{-22}$ |
| EGFR | −0.0866 | 0.917 | 0.717 | 1.174 | $4.92 \times 10^{-1}$ | EGFR | −0.0790 | 0.924 | 0.765 | 1.117 | $4.14 \times 10^{-1}$ |
| EGLN1 | 0.2769 | 1.319 | 1.029 | 1.692 | $2.90 \times 10^{-2}$ | EGLN1 | 0.2562 | 1.292 | 1.068 | 1.562 | $8.36 \times 10^{-3}$ |
| ERBB3 | −0.2256 | 0.798 | 0.623 | 1.022 | $7.32 \times 10^{-2}$ | ERBB3 | −0.1948 | 0.823 | 0.681 | 0.994 | $4.35 \times 10^{-2}$ |
| ERBB4 | −0.2095 | 0.811 | 0.633 | 1.039 | $9.72 \times 10^{-2}$ | ERBB4 | −0.1649 | 0.848 | 0.702 | 1.025 | $8.76 \times 10^{-2}$ |
| ESM1 | 0.4781 | 1.613 | 1.253 | 2.077 | $2.06 \times 10^{-4}$ | ESM1 | 0.4600 | 1.584 | 1.306 | 1.921 | $2.91 \times 10^{-6}$ |
| ESPL1 | 0.8198 | 2.27 | 1.743 | 2.957 | $1.22 \times 10^{-9}$ | ESPL1 | 0.7090 | 2.032 | 1.665 | 2.48 | $3.03 \times 10^{-12}$ |
| EXO1 | 0.9435 | 2.569 | 1.96 | 3.369 | $8.66 \times 10^{-12}$ | EXO1 | 0.9066 | 2.476 | 2.015 | 3.043 | $6.70 \times 10^{-18}$ |
| FGF18 | −0.1590 | 0.853 | 0.666 | 1.092 | $2.08 \times 10^{-1}$ | FGF18 | −0.1744 | 0.84 | 0.695 | 1.016 | $7.22 \times 10^{-2}$ |
| FOXC1 | 0.0109 | 1.011 | 0.79 | 1.293 | $9.32 \times 10^{-1}$ | FOXC1 | 0.0305 | 1.031 | 0.853 | 1.245 | $7.54 \times 10^{-1}$ |
| FRY | −0.6444 | 0.525 | 0.406 | 0.678 | $8.84 \times 10^{-7}$ | FRY | −0.4829 | 0.617 | 0.508 | 0.749 | $9.96 \times 10^{-7}$ |
| GMPS | 0.4492 | 1.567 | 1.218 | 2.016 | $4.77 \times 10^{-4}$ | GMPS | 0.4035 | 1.497 | 1.235 | 1.814 | $3.93 \times 10^{-5}$ |
| GNAZ | 0.7222 | 2.059 | 1.588 | 2.669 | $4.91 \times 10^{-8}$ | GNAZ | 0.5755 | 1.778 | 1.463 | 2.162 | $7.48 \times 10^{-9}$ |
| GSK3B | 0.2919 | 1.339 | 1.044 | 1.716 | $2.15 \times 10^{-2}$ | GSK3B | 0.2814 | 1.325 | 1.095 | 1.603 | $3.76 \times 10^{-3}$ |
| GSTM3 | −0.5888 | 0.555 | 0.43 | 0.717 | $6.74 \times 10^{-6}$ | GSTM3 | −0.4797 | 0.619 | 0.51 | 0.751 | $1.19 \times 10^{-6}$ |
| JHDM1D | −0.0523 | 0.949 | 0.741 | 1.214 | $6.75 \times 10^{-1}$ | JHDM1D | −0.0111 | 0.989 | 0.818 | 1.194 | $9.05 \times 10^{-1}$ |
| KIF2C | 0.9620 | 2.617 | 1.994 | 3.435 | $4.16 \times 10^{-12}$ | KIF2C | 0.8078 | 2.243 | 1.832 | 2.746 | $5.13 \times 10^{-15}$ |
| KPNA2 | 0.7766 | 2.174 | 1.671 | 2.829 | $7.46 \times 10^{-9}$ | KPNA2 | 0.6790 | 1.972 | 1.617 | 2.404 | $1.90 \times 10^{-11}$ |
| KRT14 | −0.4292 | 0.651 | 0.506 | 0.836 | $7.99 \times 10^{-4}$ | KRT14 | −0.3230 | 0.724 | 0.598 | 0.876 | $8.91 \times 10^{-4}$ |
| KRT8 | 0.4756 | 1.609 | 1.251 | 2.07 | $2.11 \times 10^{-4}$ | KRT8 | 0.3148 | 1.37 | 1.132 | 1.657 | $1.20 \times 10^{-3}$ |
| LETMD1 | −0.2744 | 0.76 | 0.593 | 0.974 | $3.01 \times 10^{-2}$ | LETMD1 | −0.1696 | 0.844 | 0.699 | 1.02 | $7.96 \times 10^{-2}$ |
| LIN9 | 0.3407 | 1.406 | 1.095 | 1.805 | $7.52 \times 10^{-3}$ | LIN9 | 0.4266 | 1.532 | 1.263 | 1.857 | $1.48 \times 10^{-5}$ |
| LPCAT1 | 0.4285 | 1.535 | 1.194 | 1.974 | $8.25 \times 10^{-4}$ | LPCAT1 | 0.3974 | 1.488 | 1.228 | 1.803 | $4.95 \times 10^{-5}$ |
| MAD2L1 | 0.6714 | 1.957 | 1.51 | 2.537 | $3.93 \times 10^{-7}$ | MAD2L1 | 0.5800 | 1.786 | 1.468 | 2.174 | $7.17 \times 10^{-9}$ |
| MAPT | −0.8119 | 0.444 | 0.341 | 0.578 | $1.64 \times 10^{-9}$ | MAPT | −0.7700 | 0.463 | 0.379 | 0.566 | $5.53 \times 10^{-14}$ |
| MCM10 | 1.0946 | 2.988 | 2.263 | 3.947 | $1.23 \times 10^{-14}$ | MCM10 | 1.0163 | 2.763 | 2.24 | 3.407 | $2.09 \times 10^{-21}$ |
| MCM2 | 0.8290 | 2.291 | 1.757 | 2.987 | $9.05 \times 10^{-10}$ | MCM2 | 0.7495 | 2.116 | 1.732 | 2.586 | $2.39 \times 10^{-13}$ |
| MCM6 | 0.8320 | 2.298 | 1.763 | 2.995 | $7.71 \times 10^{-10}$ | MCM6 | 0.7710 | 2.162 | 1.769 | 2.643 | $5.37 \times 10^{-14}$ |
| MDM2 | −0.2497 | 0.779 | 0.608 | 0.998 | $4.78 \times 10^{-2}$ | MDM2 | −0.2971 | 0.743 | 0.614 | 0.898 | $2.19 \times 10^{-3}$ |
| MELK | 0.8858 | 2.425 | 1.855 | 3.17 | $9.22 \times 10^{-11}$ | MELK | 0.7505 | 2.118 | 1.733 | 2.588 | $2.23 \times 10^{-13}$ |
| MK167 | 1.1049 | 3.019 | 2.283 | 3.993 | $9.27 \times 10^{-15}$ | MK167 | 1.0310 | 2.804 | 2.272 | 3.462 | $8.68 \times 10^{-22}$ |
| MMP11 | 0.3556 | 1.427 | 1.112 | 1.831 | $5.23 \times 10^{-3}$ | MMP11 | 0.3988 | 1.49 | 1.23 | 1.805 | $4.51 \times 10^{-5}$ |
| MMP9 | 0.4662 | 1.594 | 1.239 | 2.051 | $2.91 \times 10^{-4}$ | MMP9 | 0.3457 | 1.413 | 1.167 | 1.711 | $3.89 \times 10^{-4}$ |
| MS4A7 | −0.5834 | 0.558 | 0.432 | 0.721 | $7.74 \times 10^{-6}$ | MS4A7 | −0.5192 | 0.595 | 0.49 | 0.723 | $1.67 \times 10^{-7}$ |
| MYBL2 | 1.1356 | 3.113 | 2.347 | 4.128 | $3.17 \times 10^{-15}$ | MYBL2 | 0.9616 | 2.616 | 2.124 | 3.221 | $1.36 \times 10^{-19}$ |
| NAT1 | −0.6773 | 0.508 | 0.392 | 0.658 | $2.82 \times 10^{-7}$ | NAT1 | −0.5551 | 0.574 | 0.472 | 0.698 | $2.47 \times 10^{-6}$ |
| NDC80 | 0.7314 | 2.078 | 1.601 | 2.697 | $3.96 \times 10^{-8}$ | NDC80 | 0.6811 | 1.976 | 1.62 | 2.41 | $1.76 \times 10^{-11}$ |
| NEK2 | 0.8734 | 2.395 | 1.834 | 3.128 | $1.42 \times 10^{-10}$ | NEK2 | 0.8224 | 2.276 | 1.858 | 2.788 | $1.88 \times 10^{-15}$ |
| NUF2 | 0.4996 | 1.648 | 1.279 | 2.123 | $1.10 \times 10^{-4}$ | NUF2 | 0.5527 | 1.738 | 1.43 | 2.113 | $2.84 \times 10^{-8}$ |
| NUSAP1 | 1.0842 | 2.957 | 2.236 | 3.91 | $2.80 \times 10^{-14}$ | NUSAP1 | 1.0210 | 2.776 | 2.249 | 3.427 | $2.10 \times 10^{-21}$ |
| ORC6 | 0.9851 | 2.678 | 2.038 | 3.519 | $1.59 \times 10^{-12}$ | ORC6 | 0.8489 | 2.337 | 1.906 | 2.865 | $3.12 \times 10^{-16}$ |
| PGR | −0.9039 | 0.405 | 0.31 | 0.53 | $3.93 \times 10^{-11}$ | PGR | −0.9571 | 0.384 | 0.312 | 0.473 | $1.48 \times 10^{-19}$ |
| PHGDH | 0.3053 | 1.357 | 1.058 | 1.741 | $1.63 \times 10^{-2}$ | PHGDH | 0.3866 | 1.472 | 1.215 | 1.783 | $7.95 \times 10^{-5}$ |
| PITRM1 | −0.0555 | 0.946 | 0.739 | 1.21 | $6.57 \times 10^{-1}$ | PITRM1 | −0.0640 | 0.938 | 0.777 | 1.134 | $5.10 \times 10^{-1}$ |
| PLK1 | 0.7830 | 2.188 | 1.682 | 2.848 | $5.62 \times 10^{-9}$ | PLK1 | 0.7115 | 2.037 | 1.668 | 2.486 | $2.78 \times 10^{-12}$ |
| PRC1 | 0.8875 | 2.429 | 1.858 | 3.175 | $8.46 \times 10^{-11}$ | PRC1 | 0.7880 | 2.199 | 1.797 | 2.691 | $2.10 \times 10^{-14}$ |
| PTTG1 | 0.9936 | 2.701 | 2.055 | 3.549 | $1.03 \times 10^{-12}$ | PTTG1 | 0.9030 | 2.467 | 2.008 | 3.03 | $7.88 \times 10^{-18}$ |
| QSOX2 | 0.3988 | 1.49 | 1.159 | 1.915 | $1.84 \times 10^{-3}$ | QSOX2 | 0.3674 | 1.444 | 1.192 | 1.749 | $1.72 \times 10^{-4}$ |
| RACGAP1 | 0.6339 | 1.885 | 1.457 | 2.439 | $1.39 \times 10^{-6}$ | RACGAP1 | 0.4867 | 1.627 | 1.341 | 1.975 | $8.32 \times 10^{-7}$ |
| RFC4 | 0.5435 | 1.722 | 1.335 | 2.221 | $2.88 \times 10^{-5}$ | RFC4 | 0.5110 | 1.667 | 1.373 | 2.025 | $2.49 \times 10^{-7}$ |
| RRM2 | 1.0699 | 2.915 | 2.207 | 3.849 | $4.61 \times 10^{-14}$ | RRM2 | 0.8725 | 2.393 | 1.951 | 2.936 | $5.90 \times 10^{-17}$ |
| RUNDC1 | −0.6311 | 0.532 | 0.411 | 0.687 | $1.36 \times 10^{-6}$ | RUNDC1 | −0.5586 | 0.572 | 0.471 | 0.695 | $1.96 \times 10^{-8}$ |
| SCUBE2 | −0.5745 | 0.563 | 0.436 | 0.727 | $1.02 \times 10^{-5}$ | SCUBE2 | −0.5092 | 0.601 | 0.495 | 0.73 | $2.76 \times 10^{-7}$ |
| SERF1A | −0.0030 | 0.997 | 0.779 | 1.276 | $9.83 \times 10^{-1}$ | SERF1A | −0.0161 | 0.984 | 0.815 | 1.188 | $8.66 \times 10^{-1}$ |
| SFRP1 | −0.3682 | 0.692 | 0.539 | 0.889 | $3.92 \times 10^{-3}$ | SFRP1 | −0.2904 | 0.748 | 0.618 | 0.905 | $2.81 \times 10^{-3}$ |
| SLC7A5 | 0.7381 | 2.092 | 1.61 | 2.718 | $3.23 \times 10^{-8}$ | SLC7A5 | 0.6119 | 1.844 | 1.515 | 2.245 | $1.08 \times 10^{-9}$ |
| SPEF1 | −0.3038 | 0.738 | 0.576 | 0.947 | $1.68 \times 10^{-2}$ | SPEF1 | −0.3383 | 0.713 | 0.589 | 0.863 | $5.23 \times 10^{-4}$ |
| STK32B | −0.3481 | 0.706 | 0.55 | 0.906 | $6.24 \times 10^{-3}$ | STK32B | −0.3453 | 0.708 | 0.585 | 0.857 | $4.03 \times 10^{-4}$ |
| STMN1 | 0.8842 | 2.421 | 1.854 | 3.162 | $8.38 \times 10^{-11}$ | STMN1 | 0.7328 | 2.081 | 1.704 | 2.54 | $6.09 \times 10^{-13}$ |
| TGFB3 | −0.3439 | 0.709 | 0.552 | 0.91 | $6.88 \times 10^{-3}$ | TGFB3 | −0.2666 | 0.766 | 0.634 | 0.927 | $6.12 \times 10^{-3}$ |
| TP53 | −0.3552 | 0.701 | 0.546 | 0.9 | $5.35 \times 10^{-3}$ | TP53 | −0.3052 | 0.737 | 0.609 | 0.892 | $1.74 \times 10^{-3}$ |
| TRMT2A | −0.2758 | 0.759 | 0.592 | 0.974 | $3.00 \times 10^{-2}$ | TRMT2A | −0.1863 | 0.83 | 0.687 | 1.004 | $5.47 \times 10^{-2}$ |
| TYMS | 0.6560 | 1.927 | 1.489 | 2.495 | $6.31 \times 10^{-7}$ | TYMS | 0.6021 | 1.826 | 1.501 | 2.222 | $1.81 \times 10^{-9}$ |
| UBE2C | 0.6429 | 1.902 | 1.47 | 2.461 | $9.88 \times 10^{-7}$ | UBE2C | 0.6785 | 1.971 | 1.617 | 2.404 | $1.95 \times 10^{-11}$ |

TABLE 4-continued

Univariate Results of Prognostically Significant Genes in the 95-Gene Signature of the Validation Cohort

| | Validation: Endocrine-treated | | | | | | Validation: Endocrine-treated + Adjuvant Chemotherapy | | | | |
|---|---|---|---|---|---|---|---|---|---|---|---|
| | Coef | HR | HR.95L | HR.95U | P | | Coef | HR | HR.95L | HR.95U | P |
| UBE2T | 1.0753 | 2.931 | 2.22 | 3.871 | $3.41 \times 10^{-14}$ | UBE2T | 0.9532 | 2.594 | 2.108 | 3.192 | $2.29 \times 10^{-19}$ |
| WISP1 | −0.2850 | 0.752 | 0.587 | 0.965 | $2.48 \times 10^{-2}$ | WISP1 | −0.2107 | 0.81 | 0.67 | 0.979 | $2.94 \times 10^{-2}$ |
| ZNF385B | −0.2536 | 0.776 | 0.605 | 0.994 | $4.50 \times 10^{-2}$ | ZNF385B | −0.1948 | 0.823 | 0.681 | 0.995 | $4.38 \times 10^{-2}$ |

TABLE 9

Normalized RNA Abundance Values per Gene Within Pathway Modules showing Relative RNA Abundance in the Validation Cohort

| Gene | Low | High | FC | P | Q | Gene | Low | High | FC | P | Q |
|---|---|---|---|---|---|---|---|---|---|---|---|
| | | | | | Module 1 | | | | | | |
| BIRC5 | 5.63 | 7.07 | 1.44 | $7.23 \times 10^{-180}$ | $1.37 \times 10^{-178}$ | ESPL1 | 4.15 | 5.38 | 1.23 | $2.38 \times 10^{-167}$ | $2.06 \times 10^{-166}$ |
| BUB1B | 4.60 | 5.74 | 1.15 | $1.78 \times 10^{-180}$ | $4.24 \times 10^{-179}$ | KIF2C | 3.94 | 5.01 | 1.06 | $1.80 \times 10^{-139}$ | $6.84 \times 10^{-139}$ |
| CCNB1 | 6.25 | 7.30 | 1.05 | $1.76 \times 10^{-173}$ | $2.39 \times 10^{-172}$ | MAD2L1 | 4.92 | 5.58 | 0.66 | $1.12 \times 10^{-107}$ | $2.95 \times 10^{-107}$ |
| CCNB2 | 4.34 | 5.45 | 1.11 | $6.28 \times 10^{-153}$ | $2.84 \times 10^{-152}$ | NDC80 | 3.64 | 4.65 | 1.01 | $6.61 \times 10^{-137}$ | $2.42 \times 10^{-136}$ |
| CDC20 | 5.48 | 6.48 | 1.00 | $1.68 \times 10^{-153}$ | $8.00 \times 10^{-153}$ | NUF2 | 3.59 | 4.37 | 0.78 | $1.70 \times 10^{-83}$ | $3.85 \times 10^{-83}$ |
| CENPA | 3.87 | 5.02 | 1.15 | $1.47 \times 10^{-149}$ | $6.34 \times 10^{-149}$ | PTTG1 | 6.25 | 7.24 | 0.99 | $9.36 \times 10^{-175}$ | $1.48 \times 10^{-173}$ |
| CENPF | 6.65 | 7.80 | 1.15 | $4.51 \times 10^{-167}$ | $3.57 \times 10^{-166}$ | STMN1 | 7.55 | 8.24 | 0.70 | $7.53 \times 10^{-103}$ | $1.93 \times 10^{-102}$ |
| | | | | | Module 2 | | | | | | |
| BAG1 | 6.01 | 5.96 | 0.04 | $6.01 \times 10^{-2}$ | $6.80 \times 10^{-2}$ | GSK3B | 7.73 | 7.82 | 0.10 | $4.22 \times 10^{-10}$ | $5.20 \times 10^{-10}$ |
| BCL2 | 7.06 | 6.67 | 0.39 | $1.60 \times 10^{-22}$ | $2.17 \times 10^{-22}$ | MAPT | 8.24 | 7.50 | 0.74 | $4.38 \times 10^{-34}$ | $7.43 \times 10^{-34}$ |
| CCNE1 | 4.27 | 4.96 | 0.69 | $7.17 \times 10^{-91}$ | $1.70 \times 10^{-90}$ | MDM2 | 8.39 | 8.42 | 0.03 | $4.86 \times 10^{-1}$ | $5.13 \times 10^{-1}$ |
| EGFR | 5.79 | 5.20 | 0.59 | $2.28 \times 10^{-29}$ | $3.61 \times 10^{-29}$ | RRM2 | 6.14 | 7.35 | 1.22 | $2.66 \times 10^{-164}$ | $1.94 \times 10^{-163}$ |
| ERBB3 | 7.97 | 7.99 | 0.02 | $7.16 \times 10^{-1}$ | $7.31 \times 10^{-1}$ | TP53 | 7.06 | 6.94 | 0.12 | $1.12 \times 10^{-7}$ | $1.35 \times 10^{-7}$ |
| ERBB4 | 5.93 | 5.46 | 0.48 | $2.17 \times 10^{-17}$ | $2.86 \times 10^{-17}$ | TYMS | 6.83 | 7.67 | 0.84 | $8.16 \times 10^{-131}$ | $2.50 \times 10^{-130}$ |
| FGF18 | 4.52 | 3.99 | 0.53 | $5.15 \times 10^{-25}$ | $7.53 \times 10^{-25}$ | | | | | | |
| | | | | | Module 3 | | | | | | |
| ASPM | 4.35 | 5.49 | 1.15 | $2.59 \times 10^{-155}$ | $1.29 \times 10^{-154}$ | NEK2 | 5.89 | 7.11 | 1.21 | $7.06 \times 10^{-169}$ | $6.71 \times 10^{-168}$ |
| AURKA | 5.09 | 5.76 | 0.68 | $8.61 \times 10^{-115}$ | $2.34 \times 10^{-114}$ | PLK1 | 4.78 | 5.97 | 1.19 | $5.68 \times 10^{-156}$ | $3.18 \times 10^{-155}$ |
| CCNE2 | 4.32 | 5.35 | 1.03 | $1.75 \times 10^{-115}$ | $4.89 \times 10^{-115}$ | PRC1 | 5.23 | 6.24 | 1.01 | $1.67 \times 10^{-155}$ | $8.82 \times 10^{-155}$ |
| CDK1 | 5.11 | 6.26 | 1.15 | $2.52 \times 10^{-157}$ | $1.50 \times 10^{-156}$ | RACGAP1 | 3.23 | 3.78 | 0.55 | $6.58 \times 10^{-46}$ | $1.28 \times 10^{-45}$ |
| CEP55 | 5.03 | 6.23 | 1.20 | $2.43 \times 10^{-169}$ | $2.88 \times 10^{-168}$ | UBE2C | 7.38 | 8.10 | 0.72 | $2.79 \times 10^{-100}$ | $6.98 \times 10^{-100}$ |
| ECT2 | 6.84 | 7.51 | 0.66 | $7.19 \times 10^{-136}$ | $2.44 \times 10^{-135}$ | | | | | | |
| | | | | | Module 4 | | | | | | |
| CCND1 | 10.63 | 10.86 | 0.23 | $1.55 \times 10^{-6}$ | $1.82 \times 10^{-6}$ | MCM6 | 6.56 | 7.00 | 0.44 | $3.02 \times 10^{-90}$ | $7.00 \times 10^{-90}$ |
| CDC6 | 4.65 | 5.66 | 1.01 | $2.07 \times 10^{-131}$ | $6.56 \times 10^{-131}$ | MYBL2 | 5.22 | 6.94 | 1.71 | $7.49 \times 10^{-182}$ | $2.37 \times 10^{-180}$ |
| LIN9 | 5.42 | 5.81 | 0.38 | $3.91 \times 10^{-44}$ | $7.14 \times 10^{-44}$ | ORC6 | 3.64 | 4.72 | 1.08 | $7.86 \times 10^{-122}$ | $2.33 \times 10^{-121}$ |
| MCM10 | 4.13 | 5.30 | 1.17 | $9.54 \times 10^{-164}$ | $6.47 \times 10^{-163}$ | RFC4 | 5.73 | 6.20 | 0.47 | $7.71 \times 10^{-72}$ | $1.70 \times 10^{-71}$ |
| MCM2 | 5.26 | 5.98 | 0.72 | $4.90 \times 10^{-119}$ | $1.41 \times 10^{-118}$ | UBE2T | 5.67 | 6.77 | 1.10 | $6.07 \times 10^{-169}$ | $6.41 \times 10^{-168}$ |
| | | | | | Module 5 | | | | | | |
| CDH3 | 5.12 | 5.09 | 0.03 | $4.99 \times 10^{-1}$ | $5.21 \times 10^{-1}$ | MMP9 | 6.73 | 7.56 | 0.84 | $1.97 \times 10^{-26}$ | $3.06 \times 10^{-26}$ |
| MMP9 | 6.73 | 7.56 | 0.84 | $1.97 \times 10^{-26}$ | $3.06 \times 10^{-26}$ | | | | | | |
| | | | | | Module 6 | | | | | | |
| KPNA2 | 6.61 | 7.44 | 0.83 | $6.72 \times 10^{-133}$ | $2.20 \times 10^{-132}$ | KRT8 | 10.81 | 11.13 | 0.32 | $2.48 \times 10^{-16}$ | $3.19 \times 10^{-16}$ |

TABLE 11

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| BCL2 | Flupirtine maleate<br>Lindopharm<br>AWD Pharma<br>Meda Synthetic Biologics<br>Bayer | Launched-1986 | Non-Opioid Analgesics<br>Creutzfeldt-Jakob Disease<br>Treatment of Multiple Sclerosis | Signal Transduction Modulators<br>Voltage-Gated K(V) 7 (KCNQ) Channel Activators<br>NMDA Antagonists |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Oblimersen sodium<br>Genta<br>National Cancer Institute<br>Merck & Co. | Pre-Registered | BCL2 Expression Inhibitors<br>Apoptosis Inducers | Small Cell Lung Cancer<br>Prostate Cancer<br>Lymphocytic Leukemia<br>Multiple Myeloma<br>Non-Small Cell Lung Cancer<br>Leukemia<br>Gastric Cancer<br>Melanoma Skin Cancer<br>Breast Cancer<br>Pancreatic Cancer<br>Renal Cancer<br>Myeloid Leukemia<br>Colorectal Cancer<br>Liver Cancer<br>Non-Hodgkin's Lymphoma<br>Solid Tumor |
| | Venetoclax<br>AbbVie<br>Genentech | Pre-Registered | Bcl-2 Inhibitors Signal<br>Transduction Modulators<br>Apoptosis Inducers | Lymphocytic Leukemia<br>Multiple Myeloma<br>Myeloid Leukemia<br>Systemic Lupus<br>Erythematosus<br>Agents for Non-Hodgkin's<br>Lymphoma |
| | Obatoclax mesylate<br>National Cancer Institute<br>Teva | Phase III | Bcl-2 Inhibitors<br>Bcl-xl Inhibitors Signal<br>Transduction<br>Modulators Bcl-2-Related<br>Protein A1 (BFL-1; BCL2A1)<br>Inhibitors<br>Apoptosis Inducers | Small Cell Lung Cancer<br>Lymphocyti Leukemia<br>Multiple Myeloma<br>Myelodysplastic Syndrome<br>Non-Small Cell Lung Cancer<br>Lymphoma<br>Myeloid<br>Leukemia<br>Solid Tumors<br>Hematologic Agents |
| | Alvocidib Hydrochloride<br>National Cancer Institute<br>Sanofi<br>Memorial Sloan-Kettering<br>Cancer Center<br>Tolero Pharmaceuticals<br>Mayo Clinic | Phase II | Mcl-1 Inhibitors<br>Bcl-2 Inhibitors<br>CDK1 Inhibitors<br>Signal Transduction Modulators<br>CDK4 Inhibitors<br>CDK9/Cyclin T1 Inhibitors<br>CDK2 Inhibitors<br>CDK7 Inhibitors<br>Apoptosis Inducers<br>CDK6 Inhibitors<br>Survivin Inhibitors<br>X-Chromosome-Linked Inhibitor<br>of Apoptosis<br>Protein (XIAP) Inhibitors | Prostate Cancer<br>Lymphocytic Leukemia<br>Multiple Myeloma<br>Sarcoma<br>Lung Cancer<br>Leukemia<br>Gastric Cancer<br>Melanoma<br>Breast Cancer<br>Ovarian Cancer<br>Cancer of Unspecified Body<br>Location/System<br>Pancreatic Cancer<br>Colorectal Cancer<br>Renal Cancer<br>Myeloid Leukemia<br>Hematological Cancer<br>Liver Cancer<br>Non-Hodgkin's Lymphoma<br>Solid Tumors<br>Head and Neck Cancer |
| | Bardoxolone methyl<br>Dartmouth College<br>Abbott<br>M. D. Anderson Cancer Center<br>Kyowa Hakko Kirin<br>Reata Pharmaceuticals | Phase II | Bcl-2 Inhibitors Nuclear Factor<br>Erythroid 2-Related Factor 2<br>(NFE2-Related Factor<br>2; NFE2L2; NRF2) Activators<br>NF-kappaB (NFKB) Activation<br>Inhibitors<br>Signal Transduction Modulators<br>IKK-1 (IKKalpha) Inhibitors<br>Anti-inflammatory Drugs<br>Heme Oxygenase Activators<br>Glutathione Reductase<br>(NADPH) Activators<br>Apoptosis Inducers<br>PPARgamma Agonists<br>Angiogenesis Inhibitors<br>Nitric Oxide (NO) Production<br>Inhibitors | Interstitial Lung Diseases,<br>Renal Diseases Inflammatory<br>Bowel Disease,<br>Melanoma<br>Hypertension,<br>Pancreatic Cancer<br>Rheumatoid Arthritis,<br>Autoimmune Diseases<br>Solid Tumors |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | (−)-Gossypol<br>National Cancer Institute<br>University of Iowa<br>Ohio State University<br>National Institutes of Health University of Michigan<br>Ascentage Pharma<br>Ascenta | Phase II | Mcl-1 Inhibitors<br>Bcl-xl Inhibitors<br>Bcl-2 Inhibitors<br>Signal Transduction Modulators<br>Lipid Peroxidation Inhibitors<br>Growth Factor Modulators<br>Bcl-2-Related Protein A1 (BFL-1; BCL2A1) Inhibitors<br>Bcl-w Inhibitors<br>Apoptosis Inducers<br>11beta-Hydroxysteroid Dehydrogenase (11beta-HSD) Inhibitors<br>RNA-Binding Protein Musashi Homolog 1 (MSI1) Inhibitors | Small Cell Lung Cancer<br>Prostate Cancer<br>Lymphocytic Leukemia<br>Non-Small Cell Lung Cancer<br>Oncolytic Drugs<br>Chemopreventive Agents<br>Digestive/Gastrointestinal Cancer<br>Antipsoriatics<br>Glioblastoma Multiforme<br>Non-Hodgkin's Lymphoma<br>Head and Neck Cancer |
| | PNT-2258<br>ProNAi Therapeutics | Phase II | Bcl-2 Inhibitors<br>Signal Transduction Modulators<br>Apoptosis Inducers | Non-Hodgkin's Lymphoma<br>Solid Tumors |
| | Navitoclax<br>National Cancer Institute<br>AbbVie | Phase II | Bcl-xl Inhibitors<br>Bcl-2 Inhibitors<br>Signal Transduction Modulators<br>Bcl-2-Related Protein A1 (BFL-1; BCL2A1) Inhibitors<br>Bcl-w Inhibitors<br>Apoptosis Inducers | Lung Cancer<br>Lymphocytic Leukemia<br>Multiple Myeloma<br>Prostate Cancer Lymphoma<br>Solid Tumors<br>Liver Cancer<br>Antineoplastic Enhancing Agents |
| BIRC5 | Gataparsen<br>Isis Pharmaceuticals<br>Lilly | Phase II | Apoptosis Inducers<br>BIRC5 (Survivin) Expression Inhibitors | Prostate Cancer<br>Non-Small Cell Lung Cancer<br>Oncolytic Drugs<br>Myeloid Leukemia |
| | SVN53-67/M57-KLH<br>Roswell Park Cancer Institute | Phase II | Cancer Immuno | |
| CCND1 | Curcumin<br>Tel Aviv Sourasky Medical Center<br>Plantacor Central Drug Research<br>Institute Mahidol University<br>M. D. Anderson Cancer Center<br>Johns Hopkins University<br>Hadassah Medical Organization<br>Seer Pharmaceuticals<br>Chinese University of Hong Kong<br>University of Pennsylvania<br>University of California, Los Angeles | Phase II | Prostaglandin G/H Synthase 2 (PTGS2; COX-2) Inhibitors<br>CCND1 Expression Inhibitors<br>NF-kappaB (NFKB) Activation Inhibitors<br>HIV Integrase Inhibitors<br>Signal Transduction Modulators P-Glycoprotein (MDR-1; ABCB1) Inhibitors<br>Anti-inflammatory Drugs<br>AP-1 Inhibitors<br>Histone N-Acetyltransferase (HAT) Inhibitors<br>Glucose-6-phosphatase Inhibitors<br>Apoptosis Inducers<br>Antioxidants<br>Prostaglandin G/H Synthase 1 (PTGS1; COX-1) Inhibitors<br>DNA Methyltransferase 1 (DNMT1) Inhibitors<br>Tau Aggregation Inhibitors<br>EGFR Expression Inhibitors<br>Angiogenesis Inhibitors<br>Free Radical Scavengers<br>Lipoxygenase Inhibitors<br>FtsZ Inhibitors<br>Wnt Signaling Inhibitors | Multiple Myeloma<br>Myelodysplastic Syndrome<br>Antimalarials<br>Cystic Fibrosis<br>Premalignant Conditions<br>Chemopreventive Agents<br>Treatment of Mucositis<br>Alzheimer's Dementia,<br>Pancreatic Cancer<br>Antiarthritic Drugs<br>Antipsoriatics<br>Colorectal Cancer<br>Antibacterial Drugs<br>Ocular Genetic Disorders |
| CDK1 | Palbociclib (Prop INN; USAN), IBRANCE | Launched-2015 | CDK6/Cyclin D3 Inhibitors<br>CDK4/Cyclin D3 Inhibitors<br>CDK4 Inhibitors<br>CDK6 Inhibitors | Lymphocytic Leukemia<br>Multiple Myeloma<br>Non-Small Cell Lung Cancer<br>Melanoma<br>Breast Cancer<br>Myeloid Leukemia<br>Non-Hodgkin's Lymphoma |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Prazosin Hydrochloride<br>Pfizer<br>Centre for Addiction and Mental Health<br>Sanofi<br>Yale University National Institute on Aging | Launched-1974 | CDK1 Inhibitors Signal Transduction Modulators<br>alpha1-Adrenoceptor Antagonists<br>Apoptosis Inducers | Treatment of Alcohol Dependency<br>Mood Disorders,<br>Benign Prostatic Hyperplasia<br>Posttraumatic Stress Disorder<br>(PTSD)<br>Raynaud's Phenomenon,<br>Heart Failure<br>Smoking Cessation Aid |
| | Rigosertib sodium<br>Baxter<br>Nat Heart, Lung, and Blood Institute<br>TempleUniversity<br>Onconova<br>SymBio | Phase III | Phosphatidylinositol 3-Kinase (PI3K) Inhibitors<br>CDK1 Inhibitors<br>Signal Transduction Modulators<br>Apoptosis Inducers<br>Angiogenesis Inhibitors<br>Polo-like Kinase-1 (Plk-1) Inhibitors<br>Antimitotic Drugs | Lymphocytic Leukemia<br>Myelodysplastic Syndrome<br>Lymphoma<br>Ovarian Cancer<br>Pancreatic Cancer<br>Myeloid Leukemia<br>Head and Neck Cancer<br>Solid Tumors |
| | Dinaciclib<br>National Cancer Institute<br>Merck & Co.<br>Ligand | Phase III | Transduction Modulators<br>CDK1/Cyclin B Inhibitors<br>CDK5/p25 Inhibitors<br>Breast Cancer-Resistant Protein (BCRP; ABCG2) Inhibitors<br>CDK9/Cyclin T1 Inhibitors<br>Apoptosis Inducers<br>CDK2/Cyclin A Inhibitors | Lymphocytic Leukemia<br>Multiple Myeloma<br>Non-Small Cell Lung Cancer<br>Melanoma<br>Breast Cancer<br>Myeloid Leukemia<br>Non-Hodgkin's Lymphoma |
| | P-276-00<br>Piramal Life Sciences | Phase II/III | TNF-alpha Modulators<br>CDK4/Cyclin D1 Inhibitors<br>Signal Transduction Modulators<br>CDK1/Cyclin B Inhibitors<br>CDK9/Cyclin T1 Inhibitors<br>Apoptosis Inducers | Multiple Myeloma<br>Cervical Cancer<br>Melanoma<br>Breast Cancer<br>Mucositis<br>Pancreatic Cancer<br>Non-Hodgkin's Lymphoma<br>Head and Neck Cancer |
| | 7-Hydroxystaurosporine<br>National Cancer Institute<br>Kyowa Hakko Kirin<br>Keryx | Phase II | Checkpoint Kinase 1 (Chk1) Inhibitors<br>Checkpoint Kinase 2 (Chk2) Inhibitors<br>CDK1 Inhibitors Signal Transduction Modulators<br>Phosphatidylinositol 3-Kinase (PI3K) Inhibitors<br>Phosphoinositide Dependent Kinase (PDK) 1 Inhibitors<br>Na+/H+ Exchanger (NHE) Inhibitors<br>CDK4 Inhibitors<br>CDK2 Inhibitors<br>Apoptosis Inducers CDK6 Inhibitors<br>Protein Kinase C (PKC) Inhibitors | Lymphocytic Leukemia<br>Small Cell Lung Cancer<br>Lymphoma<br>Leukemia<br>Melanoma<br>Oncolytic Drugs<br>Ovarian Cancer<br>Myeloid Leukemia<br>Non-Hodgkin's Lymphoma |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Alvocidib Hydrochloride National Cancer Institute Sanofi Memorial Sloan-Kettering Cancer Center Tolero Pharmaceuticals Mayo Clinic | Phase II | Mcl-1 Inhibitors Bcl-2 Inhibitors CDK1 Inhibitors Signal Transduction Modulators CDK4 Inhibitors CDK9/Cyclin T1 Inhibitors CDK2 Inhibitors CDK7 Inhibitors Apoptosis Inducers CDK6 Inhibitors Survivin Inhibitors X-Chromosome-Linked Inhibitor of Apoptosis Protein (XIAP) Inhibitors | Prostate Cancer Lymphocytic Leukemia Multiple Myeloma Sarcoma Lung Cancer Leukemia Gastric Cancer Melanoma Oncolytic Drugs Breast Cancer Ovarian Cancer Cancer of Unspecified Body Location/System Pancreatic Cancer Colorectal Cancer Renal Cancer Myeloid Leukemia Hematological Cancer Liver Cancer Non-Hodgkin's Lymphoma Solid Tumors Head and Neck Cancer |
| | Roscovitine Cyclacel Institute of Cancer Research (ICR) CNRS | Phase II | CDK1 Inhibitors Signal Transduction Modulators CDK5 Inhibitors CDK2 Inhibitors | Oncolytic Drugs |
| | Seliciclib Cyclacel CNRS Institute of Cancer Research (ICR) | Phase II | CDK9 Inhibitors Signal Transduction Modulators CDK1 Inhibitors CDK5 Inhibitors CDK2 Inhibitors CDK7 Inhibitors Apoptosis Inducers | Lymphocytic Leukemia MultiplE Myeloma Cushing's Syndrome, Non-Small Cell Lung Cancer Lymphoma Cystic Fibrosis Oncolytic Drugs Breast Cancer Ovarian Cancer Rheumatoid Arthritis Nephritis Agents for Solid Tumors Head and Neck Cancer |
| | AT-7519 Astex Pharmaceuticals Multiple Myeloma Research Consortium Novartis Canadian Cancer Society Research Inst | Phase II | CDK9 Inhibitors Signal Transduction Modulators CDK1/Cyclin B Inhibitors CDK2/Cyclin A Inhibitors Apoptosis Inducers | Multiple Myeloma Leukemia Non-Hodgkin's Lymphoma Solid Tumors |
| | Milciclib Nerviano Medical Sciences TGen Research InstitutePfizer Tiziana Life Sciences Johns Hopkins University | Phase II | CDK1 Inhibitors Signal Transduction Modulators CDK4 Inhibitors CDK5 Inhibitors CDK2 Inhibitors High Affinity Nerve Growth Factor Receptor (TrKA) Inhibitors CDK2/Cyclin A Inhibitors | Respiratory/Thoracic Cancer Oncolytic Drugs Breast Cancer Liver Cancer Solid Tumors |
| | BAY-1000394 Bayer | | Aurora-A (ARK1) Kinase Inhibitors VEGFR-3 (FLT4) Inhibitors MAP3K9 (MLK1) Inhibitors CDK4/Cyclin D1 Inhibitors Signal Transduction Modulators CDK1/Cyclin B Inhibitors Jak3 Inhibitors CDK9/Cyclin T1 Inhibitors Jak2 Inhibitors AngiogenesisMInhibitors CDK2/Cyclin E Inhibitors CDK3/Cyclin E Inhibitors Antimitotic Drugs | Small Cell Lung Cancer Ovarian Cancer Solid Tumors |
| DTL | Datelliptium chloride BPI-Groupe Sanofi CNRS | Phase III | Alkaloids | |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| EGFR | Quercetin<br>Molsoft<br>Cincinnati<br>Children's Hospital Med Cent<br>Limerick BioPharma<br>Guizhou University | Launched | alpha-Glucosidase Inhibitors<br>MAO-A Inhibitors<br>Nav1.5 (Cardiac/SkMII)<br>Sodium Channel Blockers<br>NADDependent Protein<br>Deacetylase Sirtuin-(SIRT1)<br>Activators<br>Signal Transduction Modulators<br>Xanthine Oxidase Inhibitors<br>Cytokine Production Inhibitors<br>EGFR (HER1; erbB1) Inhibitors<br>Drugs Acting on Quorum<br>Sensing Signaling Antioxidants<br>Aldose Reductase Inhibitors<br>Protein Tyrosine Phosphatase<br>PTP-1B Inhibitors<br>Wnt Signaling Inhibitors<br>Free Radical Scavengers | Hemostatics<br>Antianemics<br>Non-Opioid Analgesics<br>Cardioprotectants<br>Oncolytic Drugs<br>Angina pectoris,<br>Antidiabetic Drugs<br>Antibacterial Drugs<br>Symptomatic Antidiabetic<br>Agents |
|  | Cetuximab<br>National Cancer Institute<br>Merck<br>Serono Universitaet zu Koeln<br>Vanderbilt University<br>Merck<br>KGaA<br>Lilly<br>Bristol-Myers Squibb<br>University College London<br>National Taiwan University<br>Universityof Michigan | Launched-2003 | Signal Transduction Modulators<br>P-Glycoprotein (MDR-1;<br>ABCB1) Inhibitors<br>Angiogenesis Inhibitors<br>Anti-EGFR | Respiratory/Thoracic Cancer<br>Prostate Cancer<br>Multiple Myeloma<br>Non-Small Cell Lung Cancer<br>Cervical Cancer<br>Neuropathic Pain,<br>Gastric Cancer<br>Bladder Cancer<br>Breast Cancer<br>Ovarian Cancer<br>Digestive/Gastrointestinal<br>Cancer<br>Pancreatic Cancer<br>Colorectal Cancer<br>Renal Cancer<br>Head and Neck Cancer<br>Liver Cancer |
|  | Gefitinib<br>National Cancer Institute<br>Stanford University<br>EORTC<br>AstraZeneca<br>M. D. Anderson Cancer Center<br>Dana-Farber Cancer Institute<br>Canadian Cancer Society<br>Research Inst<br>University of Nebraska<br>St Jude Children's Research<br>Hospital | Launched-2002 | Signal Transduction Modulators<br>EGFR (HER1; erbB1) Inhibitors | Small Cell Lung Cancer<br>Prostate Cancer<br>Sarcoma<br>Non-Small Cell Lung Cancer<br>Endocrine Cancer<br>Astrocytoma<br>Neurologic Cancer<br>Gastric Cancer<br>Bladder Cancer<br>Breast Cancer<br>Ovarian Cancer<br>Cancer of Unspecified Body<br>Location/System<br>Pancreatic Cancer<br>Colorectal Cancer<br>Glioblastoma Multiforme<br>Myeloid Leukemia<br>Renal Cancer<br>Squamous Cell Carcinoma<br>Head and Neck Cancer<br>Solid Tumors<br>Liver Cancer |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Erlotinib Hydrochloride<br>National Cancer Institute<br>Genentech<br>EORTC<br>Hopitaux Universitaires de Strasbourg<br>Roche<br>Pfizer<br>Chugai Pharmaceutical<br>M. D. Anderson Cancer Center<br>University of California, San Francisco<br>Mayo Clinic<br>Astellas Pharma<br>National Cancer Research Institute<br>University of California, Davis<br>Sanofi<br>Dana-Farber Cancer Institute<br>Schwarz Pharma<br>Canadian Cancer Society Research Inst | Launched-2004 | Signal Transduction Modulators EGFR (HER1; erbB1) Inhibitors | Prostate Cancer<br>Myelodysplastic Syndrome<br>Sarcoma<br>Non-Small Cell Lung Cancer<br>Premalignant Conditions<br>Gastrointestinal<br>Astrocytoma<br>Cervical Cancer<br>Neurologic Cancer<br>Gastric Cancer<br>Melanoma<br>Agents for Viral Hepatitis<br>Bladder Cancer<br>Brain Cancer<br>Breast Cancer<br>Ovarian Cancer<br>Digestive/Gastrointestinal Cancer<br>Pancreatic Cancer<br>Colorectal Cancer<br>Renal Cancer<br>Glioblastoma Multiforme<br>Myeloid Leukemia<br>Hematological Cancer<br>Head and Neck Cancer<br>Solid Tumors<br>Liver Cancer |
| | Panitumumab<br>Takeda National Cancer Institute<br>Amgen | Launched-2006 | Signal Transduction Modulators Anti-EGFR Human Monoclonal Antibodies | Prostate Cancer<br>Non-Small Cell Lung Cancer<br>Breast Cancer<br>Ovarian Cancer<br>Digestive/Gastrointestinal Cancer<br>Pancreatic Cancer<br>Colorectal Cancer<br>Renal Cancer<br>Head and Neck Cancer |
| | Nimotuzumab<br>BioTech Pharmaceutical<br>Kuhnil Pharmaceutical<br>CIMAB<br>InnoMab Te Arai<br>BioFarma<br>Oncoscience<br>Daiichi Sankyo<br>Gilead<br>Eurofarma Laboratorios<br>Innogene<br>Biocon | Launched-2006 | Signal Transduction Modulators Anti-EGFR | Prostate Cancer<br>Non-Small Cell Lung Cancer<br>Astrocytoma<br>Cervical Cancer<br>Neurologic Cancer<br>Gastric Cancer<br>Brain Cancer<br>Breast Cancer<br>Digestive/Gastrointestinal Cancer<br>Pancreatic Cancer<br>Colorectal Cancer<br>Glioblastoma Multiforme<br>Head and Neck Cancer<br>Solid Tumors<br>Liver Cancer |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Lapatinib ditosylate<br>National Cancer Institute<br>EORTC<br>Novartis<br>GlaxoSmithKline<br>M. D. Anderson Cancer Center<br>Concert Pharmaceuticals<br>Brown University<br>Cedars-Sinai Medical Center<br>Mayo Clinic | Launched-2007 | Signal Transduction Modulators<br>EGFR (HER1; erbB1) Inhibitors<br>HER2 (erbB2) Inhibitors | Prostate Cancer<br>Endocrine Cancer<br>Neurological Genetic<br>Disorders<br>Neurologic Cancer<br>Cervical Cancer<br>Lung Cancer<br>Gastric Cancer<br>Bladder Cancer<br>Breast Cancer<br>Ovarian Cancer<br>Digestive/Gastrointestinal Cancer<br>Cancer of Unspecified Body Location/System<br>Pancreatic Cancer<br>Colorectal Cancer<br>Renal Cancer<br>Glioblastoma Multiforme<br>Liver Cancer<br>Non-Hodgkin's Lymphoma<br>Head and Neck Cancer |
| | Bosutinib<br>Pfizer | Launched-2012 | Bcr-Abl (Bcr-Abl1) Kinase Inhibitors<br>Signal Transduction Modulators<br>Src Kinase Inhibitors<br>Signal Transducer and Activator of Transcription 5 (STAT5) Inhibitors<br>Apoptosis Inducers<br>Abl1 Kinase Inhibitors | Treatment of<br>Renal<br>Diseases<br>Non-Small Cell Lung Cancer<br>Leukemia<br>Ischemic Stroke<br>Breast Cancer<br>Pancreatic Cancer<br>Colorectal Cancer<br>Glioblastoma Multiforme<br>Myeloid Leukemia |
| | Vandetanib<br>National Cancer Institute<br>Genzyme<br>AstraZeneca<br>M. D. Anderson Cancer Center<br>Dana-Farber Cancer Institute<br>Cardiff University | Launched-2011 | VEGFR-2 (FLK-1/KDR) Inhibitors<br>VEGFR-3 (FLT4) Inhibitors<br>Signal Transduction Modulators<br>KIT (C-KIT) Inhibitors<br>RET Inhibitors<br>EGFR (HER1; erbB1) Inhibitors<br>Flt3 (FLK2/STK1) Inhibitors<br>Angiogenesis Inhibitors<br>VEGFR-1 (Flt-1) Inhibitors<br>Abl Kinase Inhibitors | Respiratory/Thoracic Cancer<br>Prostate Cancer<br>Non-Small Cell Lung Cancer<br>Endocrine Cancer<br>Neurological Genetic<br>Disorders Neurologic Cancer<br>Breast Cancer<br>Bladder Cancer<br>Digestive/Gastrointestinal Cancer<br>Pancreatic Cancer<br>Female Reproductive System Cancer<br>Colorectal Cancer<br>Renal Cancer<br>Glioblastoma Multiforme<br>Genitourinary Cancer<br>Cancer Associated Disorders, Treatment of<br>Head and Neck Cancer<br>Liver Cancer |
| | Afatinib<br>National Cancer Institute<br>Johannes Gutenberg-Universitaet<br>Mainz<br>Boehringer Ingelheim<br>Nippon<br>Boehringer Ingelheim | Launched-2013 | Signal Transduction Modulators<br>EGFR (HER1; erbB1) Inhibitors<br>HER4 (erbB4) Inhibitors<br>HER2 (erbB2)Inhibitors | Prostate Cancer<br>Non-Small Cell Lung Cancer<br>Neurologic Cancer<br>Gastric Cancer<br>Bladder Cancer<br>Breast Cancer<br>Digestive/Gastrointestinal Cancer<br>Pancreatic Cancer<br>Female Reproductive System Cancer<br>Colorectal Cancer<br>Glioblastoma Multiforme<br>Head and Neck Cancer |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Tivozanib<br>Kyowa Hakko<br>Kirin<br>AVEO Pharma<br>Astellas Pharma<br>Emory University<br>Pharmstandard<br>General<br>Hospital Corp.<br>Northwest University | Phase III | VEGFR-2 (FLK-1/KDR) Inhibitors<br>VEGFR-3 (FLT4) Inhibitors<br>Signal Transduction Modulators<br>VEGFR-1 (Flt-1) Inhibitors<br>Angiogenesis Inhibitors<br>Tyrosine Kinase Inhibitors | Sarcoma<br>Age-Related Macular Degeneration<br>Non-Small Cell Lung Cancer<br>Astrocytoma<br>Oncolytic Drugs<br>Breast Cancer<br>Ovarian Cancer<br>Female Reproductive System Cancer<br>Colorectal Cancer<br>Renal Cancer<br>Solid Tumors<br>Liver Cancer |
| | Neratinib<br>Pfizer<br>Dana-Farber Cancer Institute<br>Puma Biotechnology | Phase III | Signal Transduction Modulators<br>EGFR (HER1; erbB1) Inhibitors<br>HER4 (erbB4) Inhibitors<br>HER2 (erbB2) Inhibitors | Non-Small Cell<br>Lung Cancer<br>Breast Cancer<br>Solid Tumors |
| | Dovitinib lactate<br>Novartis<br>Samsung Medical Center | Phase III | VEGFR-2 (FLK-1/KDR) Inhibitors<br>PDGFRbeta Inhibitors<br>FGFR3 Inhibitors<br>Signal Transduction Modulators<br>EGFR (HER1; erbB1) Inhibitors<br>VEGFR-1 (Flt-1) Inhibitors<br>Angiogenesis Inhibitors<br>FGFR1 Inhibitors | Respiratory/Thoracic Cancer<br>Multiple Myeloma<br>Prostate Cancer<br>Non-Small Cell Lung Cancer<br>Endocrine Cancer<br>Neurological Genetic Disorders<br>Gastric Cancer<br>Melanoma<br>Breast Cancer<br>Bladder Cancer<br>Female Reproductive System Cancer<br>Pancreatic Cancer<br>Digestive/Gastrointestinal Cancer<br>Colorectal Cancer<br>Renal Cancer<br>Glioblastoma Multiforme<br>Myeloid Leukemia<br>Solid Tumors<br>Liver Cancer<br>Head and Neck Cancer |
| | Tesevatinib<br>Symphony Evolution<br>Kadmon<br>Exelixis | Phase III | VEGFR-2 (FLK-1/KDR) Inhibitors<br>VEGFR-3 (FLT4) Inhibitors<br>Signal Transduction Modulators<br>EGFR (HER1; erbB1) Inhibitors<br>Src Kinase Inhibitors<br>Angiogenesis Inhibitors<br>HER2 (erbB2) Inhibitors<br>EphB4 Inhibitors | Renal Diseases<br>Non-Small Cell<br>Lung Cancer<br>Breast Cancer |
| | Zalutumumab | Phase III | Transduction Modulators<br>Anti-EGFR | Non-Small Cell Lung Cancer<br>Colorectal Cancer<br>Head and Neck Cancer |
| | Necitumumab<br>MedImmune<br>Dyax<br>Merck KGaA<br>Lilly | Pre-Registered | Signal Transduction Modulators<br>Anti-EGFR | Non-Small Cell Lung Cancer<br>Colorectal Cancer<br>Solid Tumors |
| | Dacomitinib<br>SFJ Pharmaceuticals<br>Pfizer | Phase III | Signal Transduction Modulators<br>EGFR (HER1; erbB1) Inhibitors<br>HER4 (erbB4) Inhibitors<br>HER2 (erbB2) Inhibitors | Non-Small Cell Lung Cancer<br>Brain Cancer<br>Glioblastoma Multiforme<br>Head and Neck Cancer<br>Solid Tumors<br>Squamous Cell Carcinoma |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| | Tivantinib<br>National Cancer Institute<br>ArQule<br>Kyowa Hakko Kirin<br>Dana-Farber Cancer Institute<br>Daiichi Sankyo | Phase III | Signal Transduction Modulators<br>Apoptosis Inducers<br>HGFR (MET; c-Met) Inhibitors | Prostate Cancer<br>Non-Small Cell Lung Cancer<br>Gastric Cancer<br>Breast Cancer<br>Cancer of Unspecified Body Location/System<br>Pancreatic Cancer<br>Colorectal Cancer<br>Renal Cancer<br>Solid Tumors<br>Liver Cancer |
| | Icotinib Hydrochloride<br>Guangdong General Hospital<br>Beta Pharma (US) | Launched-2011 | Signal Transduction Modulators<br>EGFR (HER1; erbB1) Inhibitors | Non-Small Cell Lung Cancer<br>Brain Cancer<br>Pancreatic Cancer<br>Digestive/Gastrointestinal Cancer<br>Antipsoriatics<br>Head and Neck Cancer |
| | Cetuximab<br>Shanghai National Eng Res Cent AntibMed<br>Shanghai Biomabs Pharmaceuticals | Phase II/III | Signal Transduction Modulators<br>Anti-EGFR | Colorectal Cancer |
| | Osimertinib mesylate<br>AstraZeneca | Pre-Registered | Signal Transduction Modulators<br>EGFR (Thr790Met Mutant) Inhibitors | Non-Small Cell Lung Cancer<br>Solid Tumors |
| | Rociletinib Hydrobromide<br>Celgene<br>Clovis Oncology | Pre-Registered | Signal Transduction Modulators<br>EGFR (Thr790Met Mutant) Inhibitors<br>Apoptosis Inducers | Non-Small Cell Lung Cancer |
| | ASP-8273<br>Astellas Pharma | Phase III | Signal Transduction Modulators<br>EGFR (HER1; erbB1) Inhibitors<br>EGFR (Thr790Met Mutant) Inhibitors | Non-Small Cell Lung Cancer |
| ERBB3 | Elisidepsin<br>PharmaMar | Phase II | Signal Transduction Modulators<br>HER3 (erbB3) Inhibitors | Non-Small Cell Lung Cancer<br>Digestive/Gastrointestinal Cancer |
| | Sapitinib<br>AstraZeneca | Phase II | Signal Transduction Modulators<br>EGFR (HER1; erbB1) Inhibitors<br>HER3 (erbB3) Inhibitors<br>HER2 (erbB2) Inhibitors | Non-Small Cell Lung Cancer<br>Gastric Cancer<br>Breast Cancer<br>Colorectal Cancer<br>Solid Tumors |
| | A5-linker-ML3.9 bispecific scFv<br>Merrimack<br>Fox Chase Cancer Center | Phase II | Signal Transduction Modulators<br>Anti-HER2/neu/ErbB2<br>Anti-Receptor Tyrosine-Protein Kinase ErbB-3 (HER3) | Gastric Cancer<br>Breast Cancer<br>Digestive/Gastrointestinal Cancer<br>Solid Tumors |
| | Seribantumab<br>Merrimack | Phase II | Signal Transduction Modulators<br>Anti-Receptor Tyrosine-Protein Kinase ErbB-3 (HER3) | Non-Small Cell Lung Cancer<br>Breast Cancer<br>Oncolytic Drugs<br>Ovarian Cancer<br>Female Reproductive System Cancer<br>Solid Tumors |
| | Patritumab<br>U3 Pharma<br>Amgen<br>Daiichi Sankyo | Phase III | Signal Transduction Modulators<br>Anti-Receptor Tyrosine-Protein Kinase ErbB-3 (HER3) | Non-Small Cell Lung Cancer<br>Oncolytic Drugs<br>Breast Cancer<br>Head and Neck Cancer |
| | MM-141<br>Merrimack | Phase II | Signal Transduction Modulators<br>Anti-CD221(IGF-1R)<br>Anti-Receptor Tyrosine-Protein Kinase ErbB-3 (HER3) | Pancreatic Cancer<br>Solid Tumors |
| | Duligotuzumab<br>Genentech | Phase II | Signal Transduction Modulators<br>Anti-EGFR Anti-Receptor Tyrosine-Protein Kinase ErbB-3 (HER3) | Colorectal Cancer<br>Solid Tumors<br>Head and Neck Cancer |
| ERBB4 | Canertinib Dihydrochloride<br>Pfizer | Phase II | Transduction Modulators<br>EGFR (HER1; erbB1) Inhibitors<br>HER4 (erbB4) Inhibitors<br>HER2 (erbB2) Inhibitors | Non-Small Cell Lung Cancer<br>Breast Cancer |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
|  | Afatinib<br>National Cancer Institute<br>Johannes Gutenberg-Universitaet Mainz<br>Boehringer Ingelheim<br>Nippon<br>Boehringer Ingelheim | Launched-2013 | Signal Transduction Modulators<br>EGFR (HER1; erbB1) Inhibitors<br>HER4 (erbB4) Inhibitors<br>HER2 (erbB2) Inhibitors | Prostate Cancer<br>Non-Small Cell Lung Cancer<br>Neurologic Cancer<br>Gastric Cancer<br>Bladder Cancer<br>Breast Cancer<br>Digestive/Gastrointestinal Cancer<br>Pancreatic Cancer<br>Female Reproductive System Cancer<br>Colorectal Cancer<br>Glioblastoma Multiforme<br>Head and Neck Cancer |
|  | Neratinib<br>Pfizer<br>Dana-Farber Cancer Institute<br>Puma Biotechnology | Phase III | Signal Transduction Modulators<br>EGFR (HER1; erbB1) Inhibitors<br>HER4 (erbB4) Inhibitors<br>HER2 (erbB2) Inhibitors | Non-Small Cell Lung Cancer<br>Breast Cancer<br>Solid Tumors |
|  | Dacomitinib<br>SFJ Pharmaceuticals<br>Pfizer | Phase III | Transduction Modulators<br>EGFR (HER1; erbB1) Inhibitors<br>HER4 (erbB4) Inhibitors<br>HER2 (erbB2) Inhibitors | Non-Small Cell Lung Cancer<br>Brain Cancer<br>Glioblastoma Multiforme<br>Head and Neck Cancer<br>Solid Tumors<br>Squamous Cell Carcinoma |
|  | BMS-690514<br>Bristol-Myers Squibb | Phase II | VEGFR-3 (FLT4) Inhibitors<br>VEGFR-2 (FLK-1/KDR) Inhibitors<br>Signal Transduction Modulators<br>HER4 (erbB4) Inhibitors<br>EGFR (HER1; erbB1) Inhibitors<br>VEGFR-1 (Flt-1) Inhibitors<br>Angiogenesis Inhibitors<br>HER2 (erbB2) Inhibitors | Non-Small Cell Lung Cancer<br>Breast Cancer<br>Solid Tumors |
|  | Poziotinib<br>Spectrum Pharmaceuticals<br>Luye Pharma<br>Hanmi | Phase II | Signal Transduction Modulators<br>EGFR (HER1; erbB1) Inhibitors<br>HER4 (erbB4) Inhibitors<br>HER2 (erbB2) Inhibitors | Non-Small Cell Lung Cancer<br>Gastric Cancer<br>Breast Cancer<br>Head and Neck Cancer<br>Solid Tumors |
|  | Tarloxotinib bromide<br>Proacta<br>University of Auckland<br>Yakult Honsha<br>Threshold Pharmaceuticals | Phase II | Signal Transduction Modulators<br>EGFR (HER1; erbB1) Inhibitors<br>HER4 (erbB4) Inhibitors<br>HER2 (erbB2) Inhibitors | Non-Small Cell Lung Cancer<br>Skin Cancer<br>Head and Neck Cancer |
| FGF18 | Sprifermin | Phase II |  | Cartilage Disorders,<br>Treatment of Osteoarthritis<br>Treatment of Antiarthritic |
| GSK3B | Cycloheximide<br>University of Hawaii<br>University of Minnesota<br>Pfizer<br>Universiti Putra Malaysia | Launched | Signal Transduction Modulators<br>Glycogen Synthase Kinase 3 beta (GSK-3beta; tau Protein Kinase I) Inhibitors | Oncolytic Drugs<br>Antifungal Agents |
|  | LY-2090314<br>H. Lee Moffitt Center<br>Lilly | Phase I/II | Signal Transduction Modulators<br>Glycogen Synthase Kinase 3 beta(GSK-3beta; tau Protein Kinase I) Inhibitors | Leukemia<br>Oncolytic Drugs<br>Pancreatic Cancer<br>Type 2 Diabetes |
| MDM2 | AMG-232<br>Amgen | Phase I/II | MDM2 (hdm2) Inhibitors | Melanoma<br>Myeloid Leukemia<br>Solid Tumors |
|  | ALRN-6924<br>Roche<br>Aileron Therapeutics | Phase I/II | MDM4 (MDMX) Inhibitors<br>MDM2 (hdm2) Inhibitors | Oncolytic Drugs<br>Hematological Cancer<br>Solid Tumors |
|  | HDM-201<br>Novartis | Phase I/II | MDM2 (hdm2) Inhibitors | Sarcoma<br>Hematological Cancer<br>Solid Tumors |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| MMP9 | Zoledronic acid Monohydrate<br>Novartis<br>Merrion<br>University of Alabama at Birmingham<br>University of California, San Francisco<br>Axsome Therapeutics<br>Universiteit Leiden<br>Thar Pharmaceuticals<br>Asahi Kasei | Launched-2000 | Drugs Targeting Tumor-Associated Macrophages<br>Farnesyl Pyrophosphate Synthase Inhibitors<br>MMP9 Expression Inhibitors<br>Angiogenesis Inhibitors | Bone Cancer<br>Prostate Cancer<br>Treatment of Paget's Disease<br>Neurologic Cancer<br>Bone Resorption Inhibitors<br>Premalignant Conditions<br>Neuropathic Pain,<br>Oncolytic Drugs<br>Breast Cancer<br>Rheumatoid Arthritis<br>Osteoporosis<br>Sickle Cell Anemia<br>Hypercalcemia<br>Solid Tumors<br>Bone Diseases |
|  | Teriflunomide<br>Sanofi<br>Sugen<br>Genzyme | Launched-2012 | MMP9 Expression Inhibitors<br>MMP-9 (Gelatinase B) Inhibitors<br>Dihydroorotate Dehydrogenase (DHODH) Inhibitors<br>MMP-2 (Gelatinase A) Inhibitors | Disease-Modifying Anti-Rheumatic Drugs<br>Immunosuppressants<br>Multiple Sclerosis |
| NAT1 | Mesalazine<br>Aptalis Shire Mochida<br>Giuliani<br>Warner<br>Chilcott<br>Abbott<br>Astellas Pharma<br>Sanofi<br>Gentium<br>Falk<br>Pharma<br>Tillotts<br>SOFAR<br>Merckle<br>Recordati<br>Kyorin<br>Kyowa<br>Hakko Kirin<br>Cosmo<br>Salix<br>Zeria<br>Ajinomoto<br>Meda<br>Karolinska Institutet<br>Ferring | Launched-1984 | Protein Phosphatase 2A (PP-2A) Inhibitors<br>Arylamine N-acetyltransferase 1 (NAT1) Inhibitors<br>Signal Transduction Modulators<br>beta-Catenin Inhibitors | Inflammatory Bowel Disease,<br>Gastrointestinal Disorders<br>(Not Specified)<br>Irritable Bowel Syndrome, |
| PLK1 | Rigosertib sodium<br>Baxter<br>Nat Heart, Lung, and Blood Institute<br>Temple University<br>Onconova<br>SymBio | Phase III | Phosphatidylinositol 3-Kinase (PI3K) Inhibitors<br>CDK1 Inhibitors<br>Signal Transduction Modulators<br>Apoptosis Inducers<br>Angiogenesis Inhibitors<br>Polo-like Kinase-1 (Plk-1) Inhibitors<br>Antimitotic Drugs | Lymphocytic Leukemia<br>Myelodysplastic Syndrome<br>Lymphoma<br>Ovarian Cancer<br>Pancreatic Cancer<br>Myeloid Leukemia<br>Head and Neck Cancer<br>Solid Tumors |
|  | Volasertib<br>Boehringer Ingelheim | Phase III | Signal Transduction Modulators<br>Polo-like Kinase-1 (Plk-1) Inhibitors<br>Antimitotic Drugs | Non-Small Cell Lung Cancer<br>Bladder Cancer<br>Ovarian Cancer<br>Oncolytic Drugs<br>Female Reproductive System Cancer<br>Myeloid Leukemia |
|  | PLK1-SNALP<br>Arbutus Biopharma<br>Alnylam Pharmaceuticals | Phase II | PLK1 Expression Inhibitors | Lymphoma<br>Endocrine Cancer<br>Solid Tumors<br>Liver Cancer |

TABLE 11-continued

Summary of Late-Phase Development Compounds to Genes and Pathways Identified in the 95-Gene Signature of Residual Risk.

| Gene Target | Drug/Compound Name and Organization | Phase Development | Mode of Action | Treatment conditions |
|---|---|---|---|---|
| RRM2 | LOR-2040<br>National Cancer Institute<br>Aptose Biosciences | Phase II | RRM2 Expression Inhibitors | Prostate Cancer<br>Myelodysplastic Syndrome<br>Non-Small Cell Lung Cancer<br>Lymphoma<br>Leukemia<br>Bladder Cancer<br>Breast Cancer<br>Colorectal Cancer<br>Renal Cancer<br>Myeloid Leukemia |
| TGFb | Fresolimumab<br>National Cancer Institute<br>Icahn School of Medicine at Mount Sinai<br>Genzyme<br>MedImmune<br>Sanford-Burnham Medical Research Inst<br>University of Pennsylvania<br>Boston University | Phase II | Anti-TGFbeta2<br>Signal Transduction Modulators<br>Anti-TGFbeta<br>Anti-TGFbeta3 | Interstitial Lung Diseases,<br>Renal Diseases<br>Respiratory/Thoracic Cancer<br>Non-Small Cell Lung Cancer<br>Scleroderma<br>Neurologic Cancer<br>Melanoma<br>Renal Cancer<br>Solid Tumors<br>Hematopoiesis Disorders |

Compound search conducted using Thomson Reuters Integrity[SM]

REFERENCES

1. Abe, O., Abe, R., Enomoto, K., Kikuchi, K., Koyama, H., Masuda, H. et al. Effects of chemotherapy and hormonal therapy for early breast cancer on recurrence and 15-year survival: an overview of the randomised trials. *Lancet* 365, 1687-1717 (2005).
2. Dowsett, M., Cuzick, J., Ingle, J., Coates, A., Forbes, J., Bliss, J. et al. Meta-Analysis of Breast Cancer Outcomes in Adjuvant Trials of Aromatase Inhibitors Versus Tamoxifen. *Journal of Clinical Oncology* 28, 509-518 (2010).
3. Colleoni, M., Sun, Z., Price, K. N., Karlsson, P., Forbes, J. F., Thurlimann, B. et al. Annual Hazard Rates of Recurrence for Breast Cancer During 24 Years of Follow-Up: Results From the International Breast Cancer Study Group Trials I to V. *J. Clin. Oncol.* 34, 927-935 (2016).
4. Bartlett, J., Canney, P., Campbell, A., Cameron, D., Donovan, J., Dunn, J. et al. Selecting breast cancer patients for chemotherapy: the opening of the UK OPTIMA trial. *Clin Oncol (R. Coll. Radiol.)* 25, 109-116 (2013).
5. Paik, S., Shak, S., Tang, G., Kim, C., Baker, J., Cronin, M. et al. A multigene assay to predict recurrence of tamoxifen-treated, node-negative breast cancer. *N. Engl. J. Med.* 351, 2817-2826 (2004).
6. Paik, S., Tang, G., Shak, S., Kim, C., Baker, J., Kim, W. et al. Gene expression and benefit of chemotherapy in women with node-negative, estrogen receptor-positive breast cancer. *J. Clin. Oncol.* 24, 3726-3734 (2006).
7. Chia, S. K., Bramwell, V. H., Tu, D., Shepherd, L. E., Jiang, S., Vickery, T. et al. A 50-gene intrinsic subtype classifier for prognosis and prediction of benefit from adjuvant tamoxifen. *Clin. Cancer Res.* 18, 4465-4472 (2012).
8. Nielsen, T. O., Parker, J. S., Leung, S., Voduc, D., Ebbert, M., Vickery, T. et al. A comparison of PAM50 intrinsic subtyping with immunohistochemistry and clinical prognostic factors in tamoxifen-treated estrogen receptor-positive breast cancer. *Clin. Cancer Res.* 16, 5222-5232 (2010).
9. Perou, C. M., Sorlie, T., Eisen, M. B., van de Rijn, M., Jeffrey, S. S., Rees, C. A. et al. Molecular portraits of human breast tumours. *Nature* 406, 747-752 (2000).
10. Cardoso, F., Van't Veer, L., Rutgers, E., Loi, S., Mook, S., & Piccart-Gebhart, M. J. Clinical application of the 70-gene profile: the MINDACT trial. *J. Clin. Oncol.* 26, 729-735 (2008).
11. van de Vijver, M. J., He, Y. D., van't Veer, L. J., Dai, H., Hart, A. A., Voskuil, D. W. et al. A gene-expression signature as a predictor of survival in breast cancer. *N. Engl. J. Med.* 347, 1999-2009 (2002).
12. Ma, X. J., Salunga, R., Dahiya, S., Wang, W., Carney, E., Durbecq, V. et al. A five-gene molecular grade index and HOXB13:IL17BR are complementary prognostic factors in early stage breast cancer. *Clin. Cancer Res.* 14, 2601-2608 (2008).
13. Whitfield, M. L., Sherlock, G., Saldanha, A. J., Murray, J. I., Ball, C. A., Alexander, K. E. et al. Identification of genes periodically expressed in the human cell cycle and their expression in tumors. *Mol. Biol. Cell* 13, 1977-2000 (2002).
14. Muller, B. M., Keil, E., Lehmann, A., Winzer, K. J., Richter-Ehrenstein, C., Prinzler, J. et al. The EndoPredict Gene-Expression Assay in Clinical Practice—Performance and Impact on Clinical Decisions. *PLoS. One.* 8, e68252 (2013).
15. Afentakis, M., Dowsett, M., Sestak, I., Salter, J., Howell, T., Buzdar, A. et al. Immunohistochemical BAG1 expression improves the estimation of residual risk by IHC4 in postmenopausal patients treated with anastrazole or tamoxifen: a TransATAC study. *Breast Cancer Res. Treat.* 140, 253-262 (2013).
16. Cuzick, J., Dowsett, M., Pineda, S., Wale, C., Salter, J., Quinn, E. et al. Prognostic Value of a Combined Estrogen Receptor, Progesterone Receptor, Ki-67, and Human Epidermal Growth Factor Receptor 2 Immunohistochemical Score and Comparison With the Genomic Health Recurrence Score in Early Breast Cancer. *Journal of Clinical Oncology* 29, 4273-4278 (2011).
17. Bartlett, J. M., Bayani, J., Marshall, A., Dunn, J. A., Campbell, A., Cunningham, C. et al. Comparing Breast Cancer Multiparameter Tests in the OPTIMA Prelim Trial: No Test Is More Equal Than the Others. *J. Natl. Cancer Inst.* 108, (2016).
18. Prat, A., Parker, J. S., Fan, C., Cheang, M. C., Miller, L. D., Bergh, J. et al. Concordance among gene expression-based predictors for ER-positive breast cancer treated with adjuvant tamoxifen. *Ann. Oncol.* 23, 2866-2873 (2012).
19. van de Velde, C. J., Rea, D., Seynaeve, C., Putter, H., Hasenburg, A., Vannetzel, J. M. et al. Adjuvant tamoxifen and exemestane in early breast cancer (TEAM): a randomised phase 3 trial. *Lancet* 377, 321-331 (2011).
20. Clemens, M. R., Gladkov, O. A., Gartner, E., Vladimirov, V., Crown, J., Steinberg, J. et al. Phase II, multi-center, open-label, randomized study of YM155 plus docetaxel as first-line treatment in patients with HER2-negative metastatic breast cancer. *Breast Cancer Res. Treat.* 149, 171-179 (2015).
21. Schoffski, P. Polo-like kinase (PLK) inhibitors in pre-clinical and early clinical development in oncology. *Oncologist.* 14, 559-570 (2009).
22. Schoffski, P., Blay, J. Y., De, G. J., Brain, E., Machiels, J. P., Soria, J. C. et al. Multicentric parallel phase II trial of the polo-like kinase 1 inhibitor BI 2536 in patients with advanced head and neck cancer, breast cancer, ovarian cancer, soft tissue sarcoma and melanoma. The first protocol of the European Organization for Research and Treatment of Cancer (EORTC) Network Of Core Institutes (NOCI). *Eur. J. Cancer* 46, 2206-2215 (2010).
23. Finn, R. S., Crown, J. P., Lang, I., Boer, K., Bondarenko, I. M., Kulyk, S. O. et al. The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study. *Lancet Oncol.* 16, 25-35 (2015).
24. Finn, R. S., Dering, J., Conklin, D., Kalous, O., Cohen, D. J., Desai, A. J. et al. PD 0332991, a selective cyclin D kinase 4/6 inhibitor, preferentially inhibits proliferation of luminal estrogen receptor-positive human breast cancer cell lines in vitro. *Breast Cancer Res.* 11, R77 (2009).
25. Piccart, M., Hortobagyi, G. N., Campone, M., Pritchard, K. I., Lebrun, F., Ito, Y. et al. Everolimus plus exemestane for hormone-receptor-positive, human epidermal growth factor receptor-2-negative advanced breast cancer: overall survival results from BOLERO-2dagger. *Ann. Oncol.* 25, 2357-2362 (2014).
26. Yardley, D. A., Noguchi, S., Pritchard, K. I., Burris, H. A., III, Baselga, J., Gnant, M. et al. Everolimus plus exemestane in postmenopausal patients with HR(+) breast cancer: BOLERO-2 final progression-free survival analysis. *Adv. Ther.* 30, 870-884 (2013).
27. Hosford, S. R. & Miller, T. W. Clinical potential of novel therapeutic targets in breast cancer: CDK4/6, Src, JAK/STAT, PARP, HDAC, and PI3K/AKT/mTOR pathways. *Pharmgenomics. Pers. Med.* 7, 203-215 (2014).
28. Bartlett, J. M., Brookes, C. L., Robson, T., van de Velde, C. J., Billingham, L. J., Campbell, F. M. et al. Estrogen receptor and progesterone receptor as predictive biomarkers of response to endocrine therapy: a prospectively powered pathology study in the Tamoxifen and Exemestane Adjuvant Multinational trial. *J. Clin. Oncol.* 29, 1531-1538 (2011).
29. Bartlett, J. M., Brookes, C. L., Piper, T., van de Velde, C. J., Stocken, D., Lyttle, N. et al. Do type 1 receptor tyrosine kinases inform treatment choice? A prospectively planned analysis of the TEAM trial. *Br. J. Cancer* 109, 2453-2461 (2013).
30. Hammond, M. E., Hayes, D. F., & Wolff, A. C. Clinical Notice for American Society of Clinical Oncology-College of American Pathologists guideline recommendations on ER/PgR and HER2 testing in breast cancer. *J. Clin. Oncol.* 29, e458 (2011).
31. Wolff, A. C., Hammond, M. E., Schwartz, J. N., Hagerty, K. L., Allred, D. C., Cote, R. J. et al. American Society of Clinical Oncology/College of American Pathologists guideline recommendations for human epidermal growth factor receptor 2 testing in breast cancer. *J. Clin. Oncol.* 25, 118-145 (2007).
32. Wolff, A. C., Hammond, M. E., Hicks, D. G., Dowsett, M., McShane, L. M., Allison, K. H. et al. Recommendations for human epidermal growth factor receptor 2 testing in breast cancer: American Society of Clinical Oncology/College of American Pathologists clinical practice guideline update. *J. Clin. Oncol.* 31, 3997-4013 (2013).
33. Waggott, D., Chu, K., Yin, S., Wouters, B. G., Liu, F. F., & Boutros, P. C. NanoStringNorm: an extensible R package for the pre-processing of NanoString mRNA and miRNA data. *Bioinformatics.* 28, 1546-1548 (2012).
34. Toussaint, J., Sieuwerts, A. M., Haibe-Kains, B., Desmedt, C., Rouas, G., Harris, A. L. et al. Improvement of the clinical applicability of the Genomic Grade Index through a qRT-PCR test performed on frozen and formalin-fixed paraffin-embedded tissues. *BMC. Genomics* 10, 424 (2009).
35. Barton, S., Zabaglo, L., A'Hern, R., Turner, N., Ferguson, T., O'Neill, S. et al. Assessment of the contribution of the IHC4+C score to decision making in clinical practice in early breast cancer. *Br. J. Cancer* 106, 1760-1765 (2012).
36. Cuzick, J., Dowsett, M., Pineda, S., Wale, C., Salter, J., Quinn, E. et al. Prognostic value of a combined estrogen receptor, progesterone receptor, Ki-67, and human epidermal growth factor receptor 2 immunohistochemical score and comparison with the Genomic Health recurrence score in early breast cancer. *J. Clin. Oncol.* 29, 4273-4278 (2011).
37. Schemper, M. & Smith, T. L. A note on quantifying follow-up in studies of failure time. *Control Clin. Trials* 17, 343-346 (1996).
38. Starmans, M. H., Pintilie, M., John, T., Der, S. D., Shepherd, F. A., Jurisica, I. et al. Exploiting the noise: improving biomarkers with ensembles of data analysis methodologies. *Genome Med.* 4, 84 (2012).
39. Waggott, D., Chu, K., Yin, S., Wouters, B. G., Liu, F. F., & Boutros, P. C. NanoStringNorm: an extensible R package for the pre-processing of NanoString mRNA and miRNA data. *Bioinformatics.* 28, 1546-1548 (2012).
40. Breitling, R., Armengaud, P., Amtmann, A., & Herzyk, P. Rank products: a simple, yet powerful, new method to detect differentially regulated genes in replicated microarray experiments. *FEBS Lett.* 573, 83-92 (2004).
41. Barton, S., Zabaglo, L., A'Hern, R., Turner, N., Ferguson, T., O'Neill, S. et al. Assessment of the contribution of the IHC4+C score to decision making in clinical practice in early breast cancer. *Br. J. Cancer* 106, 1760-1765 (2012).
42. Cuzick, J., Dowsett, M., Pineda, S., Wale, C., Salter, J., Quinn, E. et al. Prognostic value of a combined estrogen receptor, progesterone receptor, Ki-67, and human epidermal growth factor receptor 2 immunohistochemical score and comparison with the Genomic Health recurrence score in early breast cancer. *J. Clin. Oncol.* 29, 4273-4278 (2011).
43. Paik, S., Shak, S., Tang, G., Kim, C., Baker, J., Cronin, M. et al. A multigene assay to predict recurrence of tamoxifen-treated, node-negative breast cancer. *N. Engl. J. Med.* 351, 2817-2826 (2004).
44. Parker, J. S., Mullins, M., Cheang, M. C., Leung, S., Voduc, D., Vickery, T. et al. Supervised risk predictor of breast cancer based on intrinsic subtypes. *J. Clin. Oncol.* 27, 1160-1167 (2009).
45. Chia, S. K., Bramwell, V. H., Tu, D., Shepherd, L. E., Jiang, S., Vickery, T. et al. A 50-gene intrinsic subtype classifier for prognosis and prediction of benefit from adjuvant tamoxifen. *Clin. Cancer Res.* 18, 4465-4472 (2012).
46. Nielsen, T. O., Parker, J. S., Leung, S., Voduc, D., Ebbert, M., Vickery, T. et al. A comparison of PAM50 intrinsic subtyping with immunohistochemistry and clinical prognostic factors in tamoxifen-treated estrogen receptor-positive breast cancer. *Clin. Cancer Res.* 16, 5222-5232 (2010).
47. Perou, C. M., Sorlie, T., Eisen, M. B., van de Rijn, M., Jeffrey, S. S., Rees, C. A. et al. Molecular portraits of human breast tumours. *Nature* 406, 747-752 (2000).
48. van de Vijver, M. J., He, Y. D., van't Veer, L. J., Dai, H., Hart, A. A., Voskuil, D. W. et al. A gene-expression signature as a predictor of survival in breast cancer. *N. Engl. J. Med.* 347, 1999-2009 (2002).
49. Toussaint, J., Sieuwerts, A. M., Haibe-Kains, B., Desmedt, C., Rouas, G., Harris, A. L. et al. Improvement of the clinical applicability of the Genomic Grade Index through a qRT-PCR test performed on frozen and formalin-fixed paraffin-embedded tissues. *BMC. Genomics* 10, 424 (2009).
50. Sparano, J. A. TAILORx: trial assigning individualized options for treatment (Rx). *Clin. Breast Cancer* 7, 347-350 (2006).
51. Sparano, J. A., Gray, R. J., Makower, D. F., Pritchard, K. I., Albain, K. S., Hayes, D. F. et al. Prospective Validation of a 21-Gene Expression Assay in Breast Cancer. *N. Engl. J. Med.* (2015).

What is claimed is:

1. A method of treating a human subject with breast cancer, the method comprising:
   treating the subject with only endocrine therapy if the subject had been found to have a relatively low residual risk if treated with endocrine-only therapy compared to a control cohort of subjects; or treating the subject with combined endocrine therapy and chemotherapy if the subject had been found to have a relatively high residual risk if treated with endocrine-only therapy compared to a control cohort of subjects, wherein residual risk is assessed according to the following method:
   a) providing a tumor sample of the breast cancer;
   b) determining the expression level of at least the 40 following biomarker genes in the tumor sample:
      ACTR3B, ANLN, ASPM, AURKA, BAG1, BCL2, BIRC5, BUB1B, CCNB1, CCNB2, CCND1, CCNE1, CCNE2, CDC20, CDC6, CDCA7, CDH3, CDK1, CENPA, CENPF, CEP55, CMC2, CX3CR1, CXXC5, DHX58, DIAPH3, DTL, EBF4, ECT2, EGFR, EGLN1, ERBB3, ERBB4, ESM1, ESPL1, EXO1, FGF18, FOXC1, FRY, and GMPS; and
   c) determining the residual risk associated with endocrine-only therapy for treatment of the breast cancer to provide a prognosis for endocrine-only treatment;
   wherein determining the residual risk comprises determining a module dysregulation score (MDS) comprising the sum of weights of the expression levels of the group of the at least 40 genes multiplied to a scaled mRNA abundance,
   wherein a high MDS score relative to a median score of the at least 40 genes in the control cohort is associated with higher residual risk and/or worse survival, and
   wherein a low MDS score relative to a median score of the at least 40 genes in the control cohort is associated lower residual risk and/or better survival.

2. The method according to claim 1, further comprising determining the expression level of one or more of the following biomarker genes: GNAZ, GSK3B, GSTM3, JHDM1D, KIF2C, KPNA2, KRT14, KRT8, LETMD1, LIN9, LPCATI, MAD2L1, MAPT, MCM10, MCM2, MCM6, MDM2, MELK, MKI67, MMP11, MMP9, MS4A7, MYBL2, NAT1, NDC80, NEK2, NUF2, NUSAP1, ORC6, PGR, PHGDH, PITRM1, PLK1, PRC1, PTTG1, QSOX2, RACGAP1, RFC4, RRM2, RUNDC1, SCUBE2, SERFIA, SFRP1, SLC7A5, SPEF1, STK32B, STMN1, TGFB3, TP53, TRMT2A, TYMS, UBE2C, UBE2T, WISP1, and ZNF385B.

3. The method of claim 1, wherein determining a residual risk of a subject to be treated with an endocrine therapy further comprises comparing a clinical indicator of the subject to a plurality of reference clinical indicators, wherein the clinical indicator comprises at least one of age, tumor grade, pathological tumor size or nodal status and fitting these clinical indicators on the MDS.

4. The method of claim 1, wherein the breast cancer is hormone receptor positive (ER+).

5. The method of claim 1, wherein the residual risk represents distant relapse-free survival.

6. The method according to claim 2, comprising determining the expression level of at least 75 of the biomarker genes,
   wherein the module dysregulation score (MDS) comprises the sum of weights of the expression levels of the group of the at least 75 genes multiplied to a scaled mRNA abundance,
   wherein a high MDS score relative to a median score of the at least 75 genes in the control cohort is associated with higher residual risk and/or worse survival, and
   wherein a low MDS score relative to a median score of the at least 75 genes in the control cohort is associated lower residual risk and/or better survival.

7. The method according to claim 2, comprising determining the expression level of at least 90 of the biomarker genes,
   wherein the module dysregulation score (MDS) comprises the sum of weights of the expression levels of the group of the at least 90 genes multiplied to a scaled mRNA abundance,
   wherein a high MDS score relative to a median score of the at least 90 genes in the control cohort is associated with higher residual risk and/or worse survival, and
   wherein a low MDS score relative to a median score of the at least 90 genes in the control cohort is associated lower residual risk and/or better survival.

8. The method according to claim 3, wherein the clinical indicators are fitted on the MDS using a multivariate Cox proportional hazards model.

9. The method according to claim 1, consisting of the 95 genes of ACTR3B, ANLN, ASPM, AURKA, BAGI, BCL2, BIRC5, BUB1B, CCNB1, CCNB2, CCND1, CCNE1, CCNE2, CDC20, CDC6, CDCA7, CDH3, CDK1, CENPA, CENPF, CEP55, CMC2, CX3CR1, CXXC5, DHX58, DIAPH3, DTL, EBF4, ECT2, EGFR, EGLN1, ERBB3, ERBB4, ESM1, ESPL1, EXO1, FGF18, FOXC1, FRY, GMPS, GNAZ, GSK3B, GSTM3, JHDM1D, KIF2C, KPNA2, KRT14, KRT8, LETMD1, LIN9, LPCAT1, MAD2L1, MAPT, MCM10, MCM2, MCM6, MDM2, MELK, MKI67, MMP11, MMP9, MS4A7, MYBL2, NAT1, NDC80, NEK2, NUF2, NUSAP1, ORC6, PGR, PHGDH, PITRM1, PLK1, PRC1, PTTG1, QSOX2, RACGAP1, RFC4, RRM2, RUNDC1, SCUBE2, SERF1A, SFRP1, SLC7AS, SPEF1, STK32B, STMN1, TGFB3, TP53, TRMT2A, TYMS, UBE2C, UBE2T, WISP1, and ZNF385B; and wherein the module dysregulation score (MDS) comprises the sum of weights of the expression levels of the group is multiplied to a scaled mRNA abundance, wherein a high MDS score relative to a median score of the 95 genes in the control cohort is associated with higher residual risk and/or worse survival, and wherein a low MDS score relative to a median score of the 95 genes in the control cohort is associated lower residual risk and/or better survival.

\* \* \* \* \*